(12) United States Patent
Ingber et al.

(10) Patent No.: US 10,087,422 B2
(45) Date of Patent: Oct. 2, 2018

(54) ORGAN CHIPS AND USES THEREOF

(71) Applicant: PRESIDENT AND FELLOWS OF HARVARD COLLEGE, Cambridge, MA (US)

(72) Inventors: Donald E. Ingber, Boston, MA (US); Kevin Kit Parker, Waltham, MA (US); Geraldine A. Hamilton, Cambridge, MA (US); Anthony Bahinski, Wilmington, DE (US)

(73) Assignee: President and Fellows of Harvard College, Cambridge, MA (US)

( * ) Notice: Subject to any disclaimer, the term of this patent is extended or adjusted under 35 U.S.C. 154(b) by 704 days.

(21) Appl. No.: 14/363,105

(22) PCT Filed: Dec. 10, 2012

(86) PCT No.: PCT/US2012/068766
§ 371 (c)(1),
(2) Date: Jun. 5, 2014

(87) PCT Pub. No.: WO2013/086502
PCT Pub. Date: Jun. 13, 2013

(65) Prior Publication Data
US 2014/0342445 A1     Nov. 20, 2014

Related U.S. Application Data

(60) Provisional application No. 61/569,029, filed on Dec. 9, 2011.

(51) Int. Cl.
*C12N 5/071*     (2010.01)
*C12M 1/00*     (2006.01)
(Continued)

(52) U.S. Cl.
CPC ........... *C12N 5/0697* (2013.01); *C12M 23/16* (2013.01); *C12M 23/34* (2013.01); *C12M 25/02* (2013.01); *C12M 35/04* (2013.01); *C12M 35/08* (2013.01)

(58) Field of Classification Search
CPC ...... C12M 23/16; C12M 23/34; C12M 25/02; C12M 35/08; C12M 35/04; C12N 5/0697
See application file for complete search history.

(56) References Cited

U.S. PATENT DOCUMENTS 5,827,729 A * 10/1998 Naughton ............... A61F 2/022
                                              210/500.21
8,968,543 B2     3/2015    Stelzle
(Continued)

FOREIGN PATENT DOCUMENTS

| WO | 2006/047758 A1 | 5/2006 |
| WO | 2008/051265 A2 | 5/2008 |
| WO | 2010009307 A2 | 1/2010 |

OTHER PUBLICATIONS

Bale, SS et al. "A novel low-volume two-chamber microfabricated platform for evaluation drug metabolism and toxicity." Technology (Singap World Sci.) Apr. 21, 2015 (17 pages).
(Continued)

*Primary Examiner* — Gautam Prakash
*Assistant Examiner* — Lydia E Edwards
(74) *Attorney, Agent, or Firm* — Nixon Peabody LLP

(57) ABSTRACT

Disclosed herein are organ chips that can be individually used or integrated together to form different microphysiological systems, e.g., for use in cell culturing, drug screening, toxicity assays, personalized therapeutic treatment, scaffolding in tissue repair and/or replacement, and/or pharmacokinetic or pharmacodynamics studies.

7 Claims, 28 Drawing Sheets

(51) Int. Cl.
*C12M 3/06* (2006.01)
*C12M 1/12* (2006.01)
*C12M 1/42* (2006.01)

(56) References Cited

U.S. PATENT DOCUMENTS

| | | | |
|---|---|---|---|
| 2002/0072116 A1* | 6/2002 | Bhatia | C12M 25/14 435/366 |
| 2008/0220516 A1 | 9/2008 | Eddington | |
| 2010/0267136 A1 | 10/2010 | Vacanti et al. | |
| 2011/0053207 A1* | 3/2011 | Hoganson | A61L 27/18 435/29 |
| 2011/0250585 A1* | 10/2011 | Ingber | C12N 5/0696 435/5 |
| 2013/0309677 A1 | 11/2013 | Blackman | |
| 2014/0342445 A1 | 11/2014 | Ingber | |

OTHER PUBLICATIONS

International Search Report and Written Opinion for International Application No. PCT/US16/64661, dated Dec. 2, 2016 (14 pages).
Rennert, K. et al. "A microfluidically perfused three dimensional human liver model." Biomaterials, vol. 71, p. 119-131. Aug. 25, 2015 (13 pages).

* cited by examiner

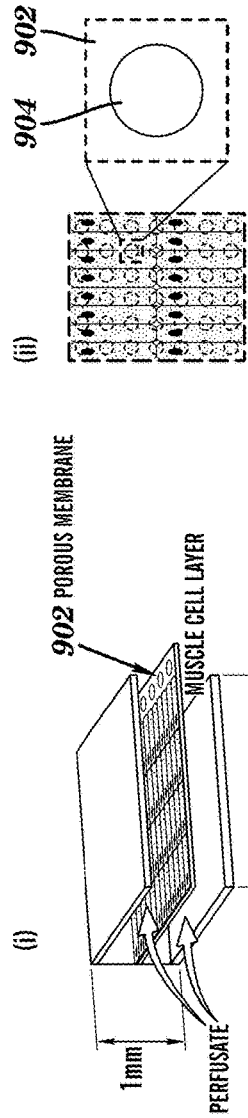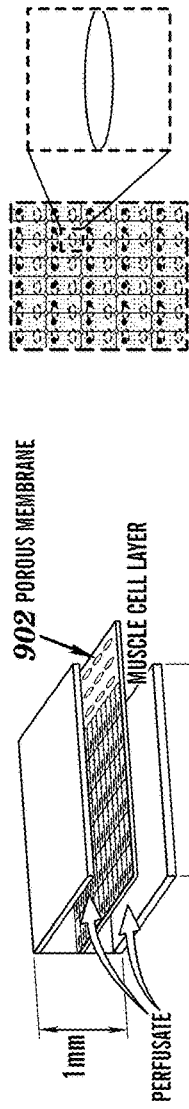
FIG. 9A
FIG. 9B

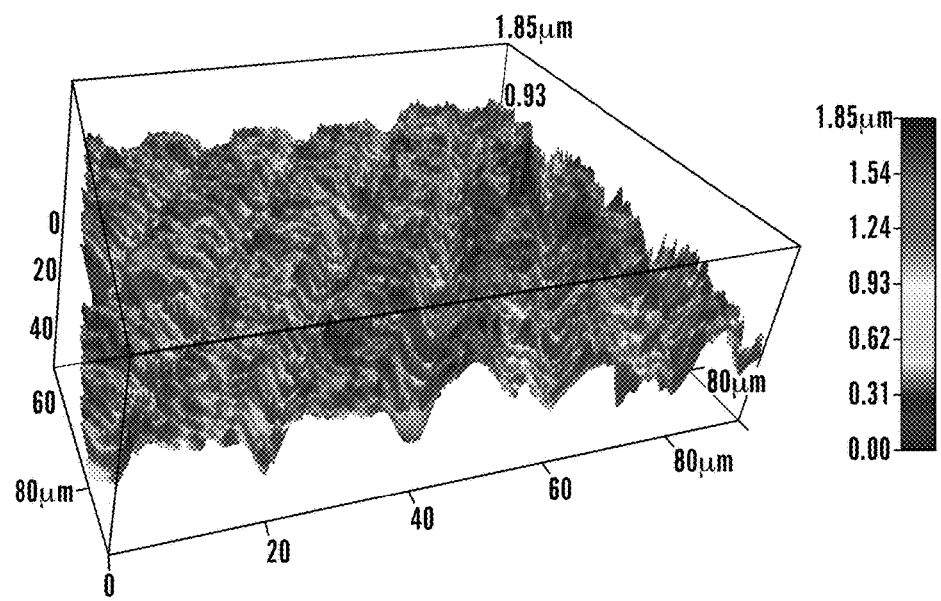
*FIG. 15A*
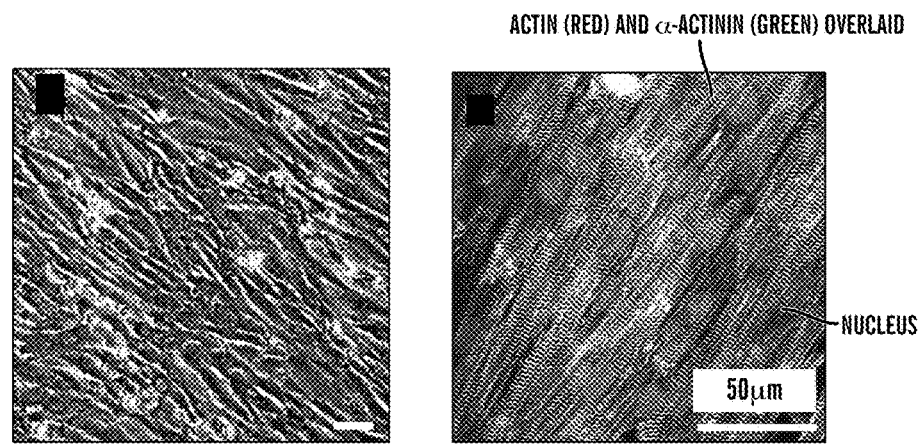
*FIG. 15B*   *FIG. 15C*

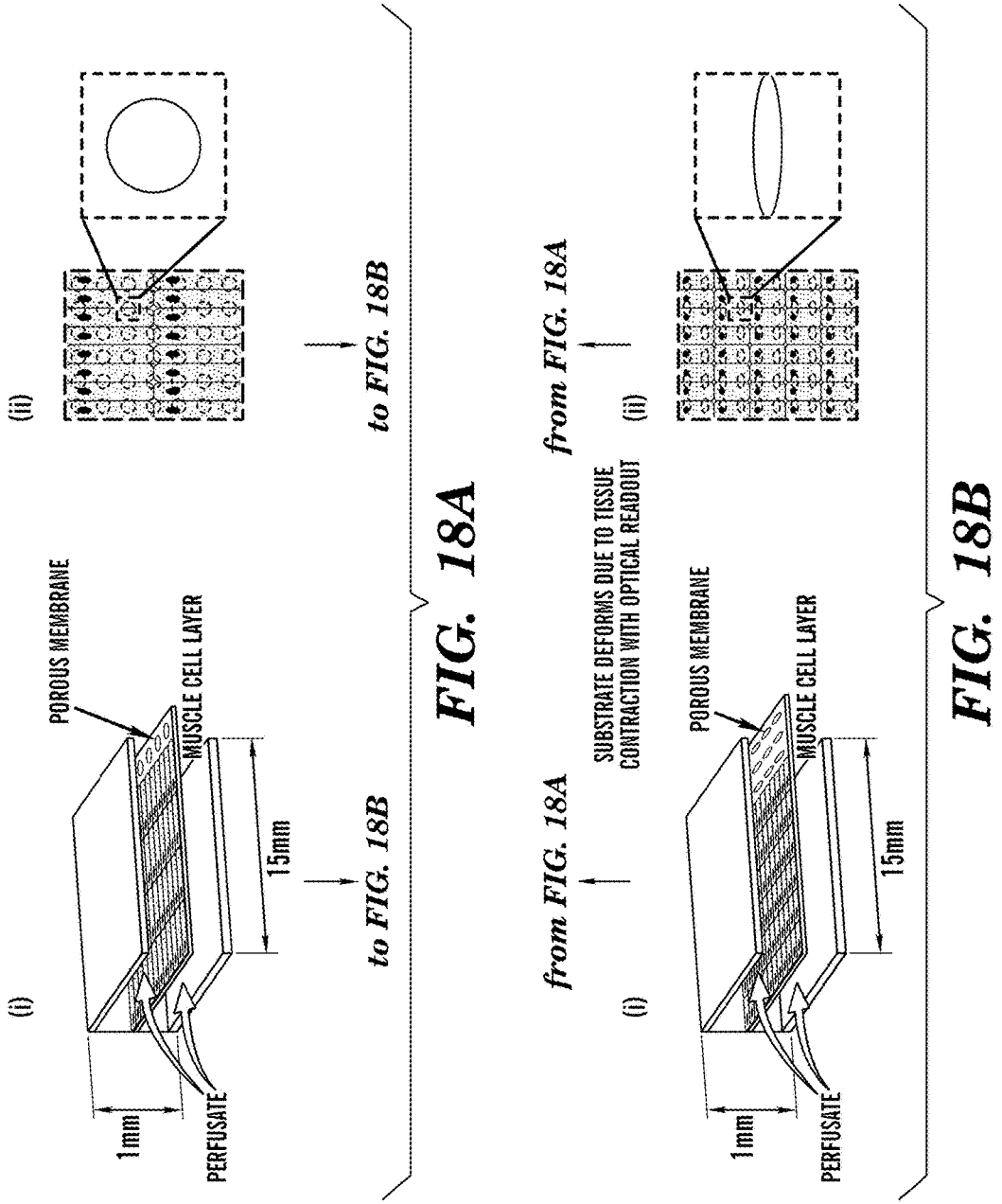

ORGAN CHIPS AND USES THEREOF

CROSS REFERENCE TO RELATED APPLICATIONS

This Application is a 35 U.S.C. § 371 National Phase Entry Application of International Application No. PCT/US2012/068766 filed Dec. 10, 2012, which designates the U.S., and which claims the benefit under 35 U.S.C § 119(e) of U.S. Provisional Application No. 61/569,029 filed Dec. 9, 2011, the contents of each of which are incorporated herein by reference in their entireties.

GOVERNMENT SUPPORT

This invention was made with government support under U01 NS073474-01 from the National Institutes of Health and Food and Drug Administration, and W911NF-12-2-0036 from the Defense Advanced Research Projects Agency. The government has certain rights in the invention.

TECHNICAL FIELD OF THE DISCLOSURE

The inventions provided herein relate to organ chips and applications thereof, e.g., analysis of drug efficacy, toxicity, and/or pharmacodynamics using one or a plurality of the organ chips.

BACKGROUND

Pharmacokinetics is the study of the action of pharmaceuticals and other biologically active compounds from the time they are introduced into the body until they are eliminated. For example, the sequence of events for an oral drug can include absorption through the various mucosal surfaces, distribution via the blood stream to various tissues, biotransformation in the liver and other tissues, action at the target site, and elimination of drug or metabolites in urine or bile. Pharmacokinetics provides a rational means of approaching the metabolism of a compound in a biological system.

One of the fundamental challenges being encountered in drug, environmental, nutritional, consumer product safety, and/or toxicology studies includes the extrapolation of metabolic data and risk assessment from in vitro cell culture assays to animals. Although some conclusions can be drawn with the application of appropriate pharmacokinetic principles, there are still substantial limitations. One concern is that current screening assays utilize cells under conditions that do not replicate their function in their natural setting. The circulatory flow, interaction with other tissues, and other parameters associated with a physiological response are not found in standard tissue culture formats. While in vivo animal models can be used to perform pharmacokinetics (PK)/pharmacodynamics (PD) study, it significantly can increase the cost of the research and the screening throughput is low. Accordingly, there is a strong need in the art for developing alternatives to the use of animal studies, e.g., in vitro models that can better replicate physiological conditions for cells to function in a similar manner as they are present in vivo. Such models can be used, e.g., for PK/PD studies, drug screening, engineered scaffolds for tissue/organ repair or replacement, and/or development of a disease model of interest.

SUMMARY

One aspect provided herein relates to microengineered organ chips or organ-on-a-chip devices. Organ chips (also known as "organ-on-a-chip device") are microfluidic devices that are configured to mimic at least one physiological function and/or response of organs of interest, e.g., from a mammal (e.g., a human), other animal or organism, an insect, or a plant. For example, organ chips or organ-on-a-chip devices can be microfluidic devices that comprise at least one type of living cells, e.g., at least one type of tissue cells, cultured therein and are designed to recapitulate the three-dimensional (3D) tissue-tissue interfaces, mechanically active microenvironments, electrical stimulation, chemical conditions and/or complex organ-level functions. Examples of the organ chips described herein, can include but are not limited to, lung chips to mimic breathing lungs, heart chips to mimic beating hearts, liver chips to mimic metabolic livers, kidney chips to mimic filtering kidney, gut chips to mimic peristalsing guts, lung airway smooth muscle chips to mimic reactive airways, skeletal muscle chips to mimic contracting skeletal muscles, skin chips to mimic skin barriers, brain chips to mimic blood-brain barriers, testis chips to mimic reproductive/endocrine testes and bone marrow chips to mimic self-renewing bone marrow.

In some embodiments, an organ chip or organ-on-a-chip device can be configured to represent a functional microenvironment of an organ (e.g., a functional unit or section of an organ, and/or a tissue-capillary interface). By way of example only, a lung-mimicking chip (or lung-on-a-chip) does not necessarily need to mimic the structure of a whole lung. Instead, the lung-on-chip can be configured to mimic the interaction of capillary cells and air sac cells in an alveolus (air sac) under a mechanical stimulation (e.g., breathing). In such embodiments, the two different cell types (e.g., capillary cells and air sac cells) can be cultured on opposing sides of a flexible porous membrane disposed in a channel of a microfluidic device. The flexible porous membrane can expand and contract to mimic the movement of an alveolar wall during lung breathing, by controlling the pressure gradient induced in the microfluidic device.

In some embodiments, living human cells can be cultured in organ chips described herein to mimic at least one physiological function and/or response of the corresponding human organs. Thus, in one embodiment, microengineered human organ chips are also provided herein.

A plurality of (e.g., 2 or more) organ chips representing various organs can be assembled or connected (e.g., fluidically connected) together to form an in vitro microphysiological system that mimics at least one physiological function and/or response of one or more systems in vivo, e.g., including, but not limited to, a circulatory system, a respiratory system, an excretory system, a nervous system, a gastrointestinal system, or any combinations thereof. Accordingly, another aspect provided herein relates to an in vitro microphysiological system that comprises at least two organ chips described herein or more, e.g., at least three organ chips, at least four organ chips or more. In some embodiments, the in vitro microphysiological system can be used to model or study mammalian (e.g., human) organs and physiological systems and effects of active agents on such organs and physiological systems. In some embodiments, the in vitro microphysiological system can be used to model or study organs and physiological systems of other animals (e.g., non-mammals), insects and/or plants, as well as effects of active agents on such organs and physiological systems.

Kits comprising a plurality of organ chips, for example, 2, 3, 4, 5, 6, 7, 8, 9, 10, or more organ chips are also provided herein. In some embodiments, the organ chips in the kit can be all the same, i.e., corresponding to the same organ. In some embodiments, at least some of the organ chips in the kit can represent a different organ. For example, a kit directed to a circulatory system can comprise at least one heart chip and at least one bone-marrow chip. In an alternative embodiment, a kit directed to a gastrointestinal system can comprise at least one liver chip and at least one gut chip. Depending on the microphysiological system of interest, the kits can comprise a plurality of distinct organ chips that are involved in the microphysiological system.

In some embodiments, the organ chips can each be individually packaged, e.g., for sterility purposes. In some embodiments, the kits can further comprise at least one agent, e.g., an appropriate culture medium for each different organ chip. In some embodiments, the kits can further comprise an instruction manual, e.g., instructions on connecting various organ chips together to form an integrated network.

The organ chips, microphysiological systems and/or kits described herein can be used for various applications where simulation of a physiological condition is desirable, e.g., drug screening, PK/PD studies, engineered scaffolds for tissue/organ repair or replacement, and/or development of a disease model of interest. In some embodiments, the cells cultured in the organ chips can be collected from a subject, e.g., for personalized therapeutic treatment. For example, subject-specific cells can be cultured in an organ chip or a microphysiological system simulated for a disease or disorder that the subject is diagnosed of, or suspected of having, and subjected to various kinds and/or dosages of drugs to determine an optimal treatment regimen for the subject.

BRIEF DESCRIPTION OF THE DRAWINGS

FIG. 2A is a schematic representation showing an exemplary configuration of a lung-on-a-chip. FIG. 2B is a schematic representation showing movement (e.g., stretching) of a flexible porous membrane under application of vacuum to side chambers of the lung-on-a-chip.

FIGS. 9A-9B is a set of schematic diagrams showing an alternative technology to monitor cellular contraction. FIG. 9A shows that cell monolayers are adhered to a deformable, perforated membrane within a microfluidic device (i & ii). FIG. 9B shows that as the muscle cell layer contracts, the substrate deforms, such that the morphology of the holes within the substrate is altered (i & ii). Hence, the morphology of the holes within the substrate can be monitored optically to determine the state of cellular contraction, with undeformed holes representing the relaxed state (FIG. 9A, ii) and deformed holes representing the contracted state (FIG. 9B, ii). The eccentricity of the holes can be evaluated with specifically-programmed algorithms, e.g., software (e.g., DBG software) originally designed to quantify nuclear eccentricity.

FIG. 10A is a schematic representation showing manufacture of an organ chip with two different kinds of muscle (striated and smooth). FIG. 10B is a set of data showing MTF deformation (i, v, ix), CM diastole (ii, vi, x), CM peak systole (iii, vii, xi), and CM stress (iv, viii, xii), before and after exposure to drugs (e.g., ET-1, and ROCK inhibitor) during the contractility assay. FIGS. 10C and 10D are data graphs showing the contractility of the VSM is considerably slower than the CM and the stress histories are depicted uniquely for each one.

FIG. 11A is a schematic representation showing a portion of a human gut chip that mimics normal villus architecture of the intestine. FIGS. 11B-11D shows that a gut chip can mimic normal villus architecture of the intestine, in part by leveraging the lung-on-a-chip (or lung chip) mechanically activated, multi-layered microfluidic architecture (FIG. 11B) to rhythmically distort the epithelium as normally occurs during peristalsis (FIGS. 11C-11D). FIG. 11E is an image showing perfusion of cells in the device. FIG. 11F is an image showing perfusion of cells in the device can maintain cell viability for weeks and result in formation of villi that take the height of the Interstitial Channel.

FIGS. 15A-15C are data showing anisotropic cardiac tissue formation on micromolded alginate substrates. FIG. 15A is data showing that the micromolding technique replicates faithfully the original pattern. FIG. 15B is a phase contrast image of representative tissues. FIG. 15C is an immunofluorescence composite image of muscular thin films: actin is red, nuclei are blue and α-actinin is green. Scale bar equals 50 µm. In some embodiments, alginate micromolded surfaces can be used to align and culture skeletal muscle cells (e.g., myotubes) in a 3-D like environment, instead of a 2-D flat substrate.

FIG. 16A is a schematic diagram showing an airway on a chip, in one embodiment, can comprise healthy bronchial tissue, cultured in liquid media (i), e.g., with a capability of drug perfusion (ii). The cell monolayer can exhibit a linear arrangement of cells, adhered to the top surface of a PDMS muscular thin film. Incubation in culture media (no drug or test agent) can yield relaxed bronchial thin films (iii), while incubation with drugs can yield contracted bronchial thin films (iv). The contractility can be measured for grading the drug response in the tissue. FIG. 16B is a schematic representation of exemplary dimensions of an airway chip containing multiple bronchial thin films (i), with an optional capability to add a layer of epithelial columnar cells (ii). This cell layer can be adhered to a porous membrane that separates the bronchial from epithelial cells, and be exposed to air flow, aerosols or a combination thereof.

FIG. 17A is a schematic representation of an airway on a chip with two chambers. Chamber 1 can contain healthy bronchial tissue, while an asthmatic phenotype can be contained in Chamber 2. The asthmatic phenotype can comprise cultures from human diseased cells or cells that are induced artificially (e.g., by toxic agents, temperature) to display at least one phenotype of diseased cells Chambers 1 and 2 can be cultured in liquid media (i) with an optional capability of drug perfusion (ii). Media and/or drugs can be kept separate between Chamber 1 and Chamber 2 by the closing of a valve (pictured in the legend, with a single pole, single throw (SPST) and Normal Open/Normal Close (NO/NC) valve). Monolayers of healthy and asthmatic cells can exhibit an anisotropic organization and can be adhered to the top surface of PDMS muscular thin films. Incubation in culture media can yield relaxed thin films (iii), while incubation with drugs can yield contracted thin films (iv). The contractility can be measured for grading the response of the different tissue types to the drugs. FIG. 17B is a schematic representation of exemplary dimensions of an airway chip containing multiple bronchial thin films (i), with an optional capability to add a layer of epithelial columnar cells (ii). This epithelial cell layer can be adhered to a porous membrane that separates the bronchial muscle from the epithelium, and be exposed to air flow, aerosols, or a combination thereof.

FIGS. 18A-18B are schematic diagrams showing an alternative technology to monitor cellular contraction. FIG. 18A shows that cell monolayers can be adhered to a "swiss cheese"—like substrate or a deformable, perforated membrane, situated within a microfluidic device (i & ii). FIG. 18B shows that as the muscle cell layer contracts, the substrate deforms, such that the morphology of the holes within the substrate is altered (i & ii). The morphology of the holes within the substrate can be monitored optically to determine the state of the cellular contraction, with undeformed holes representing the relaxed state (FIG. 18A, ii) and deformed holes representing the contracted state (FIG. 18B, ii). The eccentricity of the holes can be evaluated with a specifically-programmed algorithm, e.g., software (e.g., DBG software) originally designed to quantify nuclear eccentricity.

FIG. 19A is a schematic diagram showing exemplary manufacture of an organ chip comprising human bronchial smooth muscle thin films. FIG. 19B show data comparing the phenotypes and/or behavior of control cells and diseased cells (induced with asthma) in the organ chip. (i) and (ii) show actin staining of healthy engineered tissue and the chemically induced asthma model, respectively. Differences in actin alignment within the tissue constructs, as indicated by the orientational order parameter (iii) indicates significant remodeling of the contractile apparatus. Drug experiments (iv for healthy and v for asthma model) indicate differences in the contractile response to acetylcholine (AcH) and to a Rho kinase inhibitor (HA 1077). (vi) is a plot graph showing percentages of cell contraction and relaxation for control (healthy) and asthma models.

DETAILED DESCRIPTION OF THE INVENTION

Figure 1:
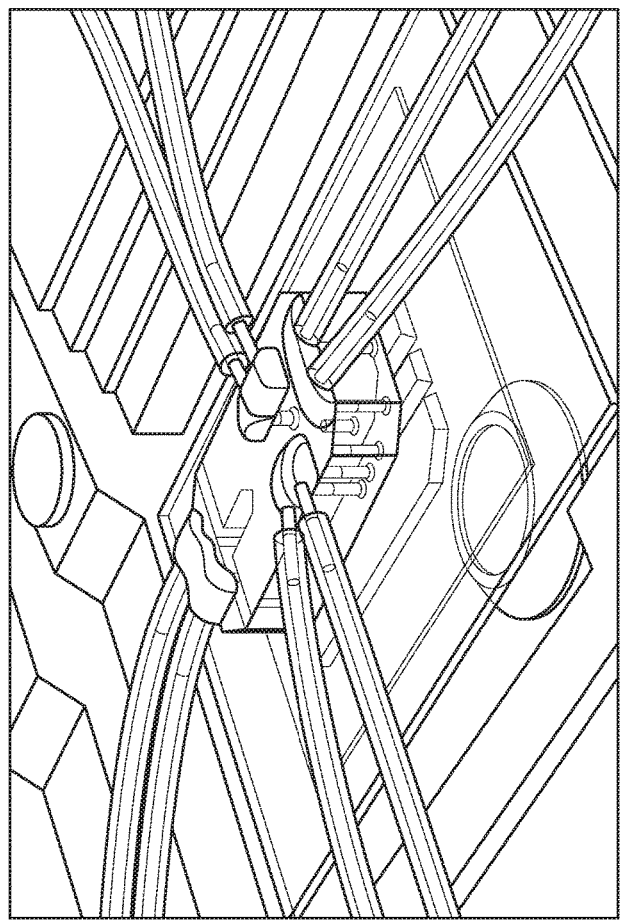
FIG. 1 is an image showing one embodiment of a lung-on-a-chip described herein, inside which the breathing of a lung is stimulated. In this embodiment, the lung-on-a-chip comprises ports for nutrient delivery, waste disposal, and/or creation of a pressure gradient to mimic breathing.

There is a need in developing alternative models to in vivo animal models for various applications, e.g., in analysis of drug efficacy, toxicity, and/or pharmacodynamics, or in studies of diseases or disorders. To this end, the inventors have developed various designs and configurations of "organ chips" (also used interchangeably herein with the term "organ-on-a-chip devices"), which can be configured as microfluidic devices to mimic at least one physiological function and/or response of different organs, and can be used to create in vitro microphysiological systems. For example, organ chips or organ-on-a-chip devices can be microfluidic devices that comprise at least one type of living cells (e.g., mammalian cells such as human cells) cultured therein and are designed to recapitulate the three-dimensional (3D) tissue-tissue interfaces, mechanically active microenvironments, electrical stimulation, chemical conditions and/or complex organ-level functions. Examples of the organ chips described herein, include, but are not limited to, lung chips to mimic breathing lung, heart chips to mimic beating heart, liver chips to mimic metabolic liver, kidney chips to mimic filtering kidney, gut chips to mimic peristalsing gut, lung airway smooth muscle chips to mimic reactive airway, skeletal muscle chips to mimic contracting skeletal muscle, skin chips to mimic skin barrier, brain chips to mimic blood-brain barrier, testis chips to mimic reproductive/endocrine testis, bone marrow chips to mimic self-renewing bone marrow, and any combinations thereof.

In some embodiments, an organ chip or organ-on-a-chip device described herein can be configured to represent a functional microenvironment of an organ (e.g., a functional unit or section of an organ, and/or a tissue-capillary interface), e.g., but not limited to, an alveolar-capillary interface of a lung, a blood-brain-barrier of a brain, or a skin barrier of a skin. By way of example only, a lung-mimicking chip (or lung-on-a-chip), which is further described below, does not necessarily need to mimic the structure of a whole lung. Instead, the lung-on-chip can be configured to mimic the interaction of capillary cells and air sac cells in an alveolus (air sac) under a mechanical stimulation (e.g., breathing). In such embodiments, the two different cell types (e.g., capillary cells and air sac cells) can be cultured on opposing sides of a flexible porous membrane disposed in a channel of a microfluidic device. The flexible porous membrane can expand and contract to mimic the movement of an alveolar wall during lung breathing, by controlling the pressure gradient induced in the microfluidic device.

The organ chips can be used, individually or connected together (e.g., fluidically connected), for various applications where simulation of a physiological condition is desirable, e.g., drug screening, pharmacokinetics (PK)/pharmacodynamics (PD) studies, engineered scaffolds for tissue/organ repair or replacement, development of a disease model, and/or personalized therapeutic treatment.

As used herein, the term "fluidically connected" refers to two or more organ chips connected in an appropriate manner such that a fluid or a least a portion of a fluid (e.g., any flowable material or medium, e.g., but not limited to, liquid, gas, suspension, aerosols, cell culture medium, and/or biological fluid) can directly or indirectly pass or flow from one organ chip to another organ chip. In some embodiments, two or more organ chips can be fluidically connected together, for example, using one or more fluid-transfer connecting means (e.g., adaptors, tubing, splitters, valves, pumps and/or channels) between the two or more organ chips. For example, two or more organ chips can be fluidically connected by connecting an outlet of one organ chip to an inlet of another organ chip using tubing, a conduit, a channel, piping or any combinations thereof. In some embodiments, two or more organ chips can be fluidically connected by, e.g., at least one pumping device and/or at least one valve device. In some embodiments, the pumping device and/or valve device can be configured for microfluidic applications, e.g., the membrane-based fluid-flow control devices as described in U.S. Provisional Application No. 61/735,206 filed Dec. 10, 2012, the content of which is incorporated herein by reference in its entirety.

In other embodiments, two or more organ chips can be fluidically connected together when one or more other connecting means (e.g., devices, systems, and/or modules that can perform an additional function other than fluid transfer, e.g., but not limited to, filtration, signal detection, and/or imaging) are present between the two or more organ chips. In these embodiments, by way of example only, two or more organ chips can be fluidically connected, when the two or more organ chips are indirectly connected, e.g., through a biosensor, a filter, and/or an analytical instrument (e.g., via tubing), such that a fluid exiting the previous organ chip can be detoured to first flow through the biosensor, filter and/or analytical instrument, e.g., for detection, analysis and/or filtration of the fluid, before it enters the next organ chip. In these embodiments, at least a portion of the fluid can pass or flow from one organ chip to another organ chip. In some embodiments, two or more organ chips can be fluidically connected by, e.g., at least one bubble trap, e.g., the bubble trap can be a membrane-based bubble trap as described in U.S. Provisional Application No. 61/696,997, filed Sep. 5, 2012, and U.S. Provisional Application No. 61/735,215 titled "Cartridge Manifold and Membrane Based-Microfluidic Bubble Trap," filed on Dec. 10, 2012, the contents of both of which are incorporated herein by reference in their entireties. Alternatively, two or more organ chips can be connected such that a fluid can pass or flow directly from one organ chip to another organ chip without any intervening components. In such an embodiment, the two or more organ chips can be designed and/or integrated on the same chip such that the outlet of one organ chip and the inlet of another organ chip share the same port.

In some embodiments, one or more organ chips (e.g., heart chips) described herein can be adapted to fluidically connected upstream and/or downstream to at least one or more different organ chips (e.g., but not limited to lung chips or liver chips) to form an in vitro microphysiological system, which can be used to determine biological effects (e.g., but not limited to, toxicity, and/or immune response) of active agents on more than one organs. Examples of active agents include, but are not limited to, cells (including, e.g., but not limited to, bacteria and/or virus), proteins, peptides, antigens, antibodies or portions thereof, enzymes, nucleic acids, siRNA, shRNA, aptamers, small molecules, antibiotics, therapeutic agents, molecular toxins, nanomaterials, particulates, aerosols, environmental contaminants or pollutants (e.g., but not limited to, microorganisms, organic/inorganic contaminants present in food and/or water, and/or air pollutants), and any combinations thereof. In some embodiments, the in vitro microphysiological system can be used to evaluate active agents that are effective in treating a disease or disorder in an organ, but might be toxic to other organ systems. For example, a drug, e.g., Ventolin, known to treat or prevent bronchospasm in subjects with reversible obstructive airway disease can be toxic to or adversely affect heart function. Thus, integration of two or more organ chips to form an in vitro microphysiological system can allow for testing or screening of drugs that are effective in treatment of a certain disease or disorder with minimal side effects or undesirable effects on other organs.

Accordingly, in another aspect, provided herein are integrated network or functional in vitro microphysiological systems, each of which mimics at least one physiological function and/or response of one or more systems in vivo, e.g., of a mammal (e.g., a human), other animal, insect and/or plant. In some embodiments, the in vitro microphysiological systems described herein can mimic at least one physiological function and/or response of one or more systems in vivo, e.g., of a mammal (e.g., a human), including, e.g., but not limited to, a circulatory system, a respiratory system, an excretory system, a nervous system, a gastrointestinal system, or any combinations thereof. The in vitro microphysiological systems described herein are generally formed by connecting (e.g., fluidically connecting) together at least two organ chips representing different organs described herein. Different combinations of organ chips can be used in the system for different applications. In some embodiments, a plurality of organ chips (e.g., at least 1, at least 2, at least 3, at least 4, at least 5 or more organ chips) can be fluidically connected, e.g., via a tubing, to each other to form a microphysiological system, e.g., a circulatory system (comprising a heart chip with vascular endothelium and a bone marrow chip), a respiratory system (comprising a lung chip, and an airway smooth muscle chip), an immune system (comprising a bone marrow chip with other immune cells, e.g., macrophages); a musculoskeletal system (comprising a skeletal muscle chip), an excretory system (comprising a lung chip, a gut chip, and a kidney chip), an urinary system (comprising a bladder chip and a kidney chip), a nervous system (comprising a brain chip with astrocytes and neuronal networks), a reproductive system (comprising testis chip), an endocrine system (comprising a testis chip), a gastrointestinal system (comprising a liver chip, and a gut chip), an integumentary system (comprising a skin chip), and a urinary system (comprising a kidney chip).

Depending on various target applications, e.g., for use as a disease model or for pharmacokinetics study of a drug, different combinations of organ chips can be selected. For example, in one embodiment, Lung Chips, Heart Chips and Liver Chips can be selected to form an in vitro microphysiological system, e.g., for determination of clinically relevant pharmacokinetics (PK)/pharmacodynamics (PD) as well as efficacy and toxicity (e.g., cardiotoxicity, which is the cause of more than 30% of all drug failures).

In some embodiments, the in vitro microphysiological system can further comprise a bone marrow chip fluidically connected to the at least two different organ chips. In one embodiment, the bone marrow chip described in the International Appl. No. PCT/US12/40188, the content of which is incorporated herein by reference in its entirety, can be utilized in the in vitro microphysiological system described herein.

In some embodiments, the in vitro microphysiological system can further comprise a spleen chip fluidically connected to the at least two different organ chips. In one embodiment, the spleen chip described in the International Appl. No. WO 2012/135834, the content of which is incorporated here by reference in its entirety, can be utilized in the in vitro microphysiological system described herein.

In some embodiments, the in vitro microphysiological systems comprising a combination (e.g., at least 2 or more) of different organ chips can be disposed in a housing and/or the universal cartridges that can hold one or more organ chips as described in the U.S. Provisional Appl. Nos. 61/569,004 filed Dec. 9, 2011 and 61/696,997 filed Sep. 5, 2012, the contents of which are incorporated herein by reference in their entireties. For example, a housing to enclose various combinations of organ chips therein can provide functionalities, e.g., but not limited to temperature control, nutrient replenishment, pressure adjustment, imaging, sample analysis, and/or any combinations thereof.

An organ chip can also include a microfluidic device which can mimic at least one physiological function of at least one living organ from a mammal (e.g., human), other animal, insect or plant. In some embodiments, an organ chip can be a microfluidic device which can mimic at least one physiological function of one mammalian (e.g., human) organ. In some embodiments, an organ chip can be a microfluidic device which can mimic physiological function of at least one (including 1, 2, 3, 4, 5, 6, 7 or more) mammalian (e.g., human) organs. In some embodiments where the organ chips mimic physiological functions of more than one mammalian (e.g., human) organs, the organ chips can comprise individual sub-units, each of which can mimic physiological function of one specific mammalian (e.g., human) organ.

In some embodiments, the in vitro microphysiological system can comprise at least two different organ chips (e.g., each organ chip representing a different organ) and at least one or more connecting means (e.g., at least two or more connecting means) between the at least two different organ chips. The at least two different organ chips can be selected from one or both of the following design and/or configuration: (i) a first organ chip can comprise: a body comprising a central channel therein, and an least partially porous and at least partially flexible first membrane positioned within the central channel and along a plane, wherein the first membrane is configured to separate the central channel to form two sub-channels, wherein one side of the first membrane is seeded with vascular endothelial cells, and the other side of the first membrane is seeded with at least one type of organ-specific parenchymal cells; and (ii) a second organ chip can comprise: a body comprising a first chamber enclosing a plurality of muscular thin films adapted to measure contraction of muscle cells, and a second chamber comprising a layer of muscle cells on the bottom surface of the second chamber, wherein the bottom surface is embedded with an array of microelectrodes for recording of action potentials, and wherein the top surface of the second chamber is placed with at least a pair of electrodes for providing electric field stimulation to the muscle cells.

In some embodiments, the at least two different organ chips can comprise at least two or more (e.g., 2, 3, 4, 5, or more) said first organ chips described herein. In one embodiment, the at least to different organ chips can comprise a lung chip described herein and a gut chip described herein. In one embodiment, the at least to different organ chips can comprise a lung chip described herein and a liver chip described herein.

In some embodiments, the at least two different organ chips can comprise at least two or more (e.g., 2, 3, 4, 5, or more) said second organ chips described herein.

In some embodiments, the at least two different organ chips can comprise at least one (e.g., 1, 2, 3, 4, 5 or more) said first organ chips described herein and at least one (e.g., 1, 2, 3, 4, 5, or more) said second organ chips described herein.

The design and/or configuration of the first and second organ chips described herein generally provide the basis for development and construction of various organ chips, e.g., but not limited to, lung chips, liver chips, gut chips, kidney chips, heart chips, skin chips, brain chips, testis chips, skeletal muscle chips, lung airway smooth muscle chips ("airway chips"), and any combinations thereof. The application and modifications of these two basic organ chip designs to create various organ chips are illustrated and described in the section below "Examples of organ chips or organ-on-a-chip devices." As described below, in some embodiments, the organ chips can be designed to have a common shape and have positioned inlets and outlets for delivery of fluids to the Microvascular and Interstitial fluid channels lined by microvascular endothelium and organ-specific parenchymal cells (e.g., but not limited to, alveolar epithelium, heart muscle, hepatocytes), respectively.

Organ chips generally comprise a base substrate and at least one channel disposed therein. The number and dimension of channels in an organ chip can vary depending on the design, dimension and/or function of the organ chip. In some embodiments, an organ chip can comprise a plurality of channels (e.g., at least two, at least three, at least four, at least five, at least six, at least seven, at least eight, at least nine, at least ten or more channels). One of skill in the art will readily be able to design and determine optimum number and/or dimension of channels required to achieve a certain application. For example, if assessment of reproducibility and/or comparison of at least two experimental conditions are desirable, an organ chip can be constructed to comprise at least two, at least three, at least four, at least five identical channels. This can provide for a number of readouts per chip, e.g., allowing assessment of reproducibility and/or for validation and implementation of the technology. For example, each channel can run a different condition (e.g., culturing normal (healthy) cells vs. diseased cells in different channels, or applying different dosages of the same drug to different channels, or applying different drugs at the same dosage to different channels). In some embodiments, an organ chip can comprise at least two parallel (e.g., 2, 3, 4, 5, 6, 7, 8, 9, 10, or more) channels. In one embodiment, an organ chip comprises four parallel channels, e.g., four identical parallel channels. Without wishing to be bound by theory, this configuration can provide quadruplicate readouts per chip.

The dimensions of the channels in the organ chips can each independently vary, e.g., depending on the channel function (e.g., as a conduit for fluid transfer or as a chamber for cell culture, e.g., for subsequent monitoring of cellular response), flow conditions, tissue microenvironment to be simulated, and/or methods for detecting cellular response. Thus, the cross-sectional dimensions of the channels can vary from about 10 µm to about 1 cm, or from about 100 µm to about 0.5 cm.

In some embodiments, at least a portion of the channels disposed in the organ chips can comprise cells. In these embodiments, the channels can each be independently lined by one layer or multilayers of organ-specific parenchymal cell types (or differentiated cells) and/or vascular endothelium (a layer of vascular endothelial cells) in relevant tissue microenvironment (e.g., mechanochemical microenvironments), with or without intervening connective tissue cells (e.g., fibroblasts, smooth muscle cells, mast cells) or immune cells (e.g., neutrophils, macrophages).

The organ chips can be sized to a specific need, e.g., for high throughput drug screening, or scaffolding, e.g., for tissue repair and/or replacement. In some embodiments, the organ chips can be implantable, and thus they can be sized to suit a target implantation site.

In some embodiments, the organ chips can be fabricated from any biocompatible materials. Examples of biocompatible materials include, but are not limited to, glass, silicons, polyurethanes or derivatives thereof, rubber, molded plastic, polymethylmethacrylate (PMMA), polycarbonate, polytetrafluoroethylene (TEFLON™), polyvinylchloride (PVC), polydimethylsiloxane (PDMS), and polysulfone. In one embodiment, organ chips can be fabricated from PDMS (poly-dimethylsiloxane). In some embodiments, the organ chips can be disposable. In some embodiments, the organ chips can be fabricated from one or more materials that allow sterilization (e.g., by UV, high temperature and/or pressure, ethylene oxide, or ethanol) after use.

In some embodiments, at least one channel of the organ chips can comprise one or more membranes, e.g., at least 1, at least 2, at least 3 or more membranes to separate the channel into sub-channels. The membrane can be rigid or at least partially flexible. The term "flexible" as used herein refers to a membrane that can be stretched and/or contracted by at least about 3%, at least about 5%, at least about 10%, at least about 15%, at least about 20%, at least about 25%, at least about 50%, at least about 60% or more, of its original length, without causing any macroscopic breaking, when a pressure is applied. In some embodiments, a flexible membrane can fully or partially restore to its original length after the pressure is released.

In some embodiments, the membrane can be non-porous or at least partially porous. In some embodiments, the pore size of the membrane can be large enough to allow cells pass through it. In some embodiments, the pore size of the membrane can be too small for cells to pass through, but large enough for nutrient or fluid molecules to pass through or permeate.

In some embodiments, the membrane can be non-coated or coated with extracellular matrix molecules (ECM) to facilitate cell adhesion (e.g., but not limited to, fibronectin, collagen, Matrigel, laminin, vitronectin, and/or any combinations thereof), other proteins such as growth factors or ligands (e.g., to facilitate cell growth and/or cell signaling). In some embodiments, the surface of the membrane can be modified and/or activated, e.g., with any art-recognized polymer surface modification techniques such that bioactive molecules, e.g., ECM molecules, carbohydrates, proteins such as growth factors or ligands, can be covalently or non-covalently attached to or coated on it. Examples of polymer surface modification such as wet chemical, organosilanization, ionized gas treatments, and UV irradiation can be used to modify the membrane to permit covalent conjugation of bioactive molecules to the modified surfaces, such as usage of hydrophilic, bifunctional, and/or branched spacer molecules. See, e.g., Goddard and Hotchkiss "Polymer surface modification for the attachment of bioactive compounds" Progress in Polymer Science, Volume 32, Issue 7, July 2007, Pages 698-725, for examples of polymer surface modification techniques.

The material for the membrane can be selected for at least one of the following properties, but are not limited to: the material is (i) biocompatible, (ii) complies with IS 10993-5 (in vitro cytotoxicity tests for medical devices), (iii) has low absorption of hydrophobic dye/drug and other chemical compounds, (iv) is cell adhesive, (v) is optically clear, is highly flexible, moldable, bondable, (vi) has low autofluorescence, (vii) does not swell in water, or (viii) has any combinations of the aforementioned properties. In one embodiment, the membrane material can include polyurethane (e.g., Clear flex 50 polyurethane). In another embodiment, the membrane material can include PDMS.

In some embodiments, the membrane can be seeded with or without cells. In some embodiments where cells are seeded on the membrane, cells can be seeded on one side or both sides of the membrane. In some embodiments, both sides of the membrane can be seeded with the same cells. In other embodiments, both sides of the membrane can be seeded with different cells, as described below, e.g., to create a Microvascular channel (comprising vascular endothelial cells) and an Interstitial channel (comprising organ-specific parenchymal cells). In some embodiments, the membrane can be seeded with at least one layer of cells, including, at least 2 layers of cells or more. Each layer of cells can be the same or different.

In some embodiments, at least one channel or sub-channel of the organ chip can be filled with a gel or a hydrogel, e.g., but not limited to, collagen gel, matrigel gel, fibrin gel, or any combinations thereof. The gel can be seeded with or without cells.

In some embodiments, at least one channel or sub-channel of the organ chip can contain a tissue, e.g., a biopsy collected from a subject.

In some embodiments, the inner surface(s) of the channel(s) (or channel walls) and/or membrane(s) that are in contact with a fluid (e.g. a liquid or a gas) can be modified for reducing non-specific binding of a species in the fluid to the inner surface(s) of the channel(s). For example, at least one surface of the channel(s) and/or membrane(s) in contact with the fluid can be coated with a surfactant, e.g., PLURONIC® 127, or a blocking protein such as bovine serum albumin, for reducing cell or protein adhesion thereto. Additional surfactant that can be used to reduce the adhesive force between the surface of the channel and non-specific binding of a species in a fluid sample can include, but are not limited to, hydrophilic (especially amphipathic) polymers and polymeric surface-acting agents; non-ionic agents such as polyhydric alcohol-type surfactants, e.g., fatty acid esters of glycerol, pentaerythritol, sorbitol, sorbitan, and more hydrophilic agents made by their alkoxylation, including polysorbates (TWEEN®); polyethylene glycol-type surfactants such as PLURONIC surfactants (e.g., poloxamers), polyethylene glycol (PEG), methoxypolyethylene glycol (MPEG), polyacrylic acid, polyglycosides, soluble polysaccharides, dextrins, microdextrins, gums, and agar; ionic agents, including anionic surfactants such as salts of carboxylic acids (soaps), sulfuric acids, sulfuric esters of higher alcohols; cationic surfactants such as salts of alkylamine type, quaternary ammonium salts, or amphoteric surfactants such as amino acid type surfactants and betaine type surfactants. A skilled artisan will readily be able to determine appropriate methods and/or reagents for use to reduce non-specific binding of a species in a fluid to the channel wall(s) and/or membranes, based on the substrate material of the microfluidic devices and/or types of species to be blocked.

In some embodiments, there can be at least one micro-post, including 1, 2, 3, 4, 5, 6, 7, 8, 9, 10 or more micro-posts within one or more channels. The dimension and/or arrangement of the micro-posts can be determined by a user. For example, the micro-posts can be used to separate cell debris from a flowing fluid to prevent clogging the downstream channel. In some embodiments, the micro-posts can be coated with an agent (e.g., antibodies) that permits capture of specific cells.

In some embodiments, the organ chips can comprise a plurality of ports. For example, the organ chips can comprise at least one inlet port for introducing culture medium, nutrients or test agents such as drugs into the organ chips, and at least one outlet port for a fluid to exit. In some embodiments, at least one port can be connected to a pump or a syringe, e.g., via a tubing, to facilitate the fluid transfer through the channel and/or to apply a pressure to the channel. In some embodiments, at least one port can be connected to at least one electrical component, e.g., an electrode for ECG measurement. In some embodiments, at least one port can be connected to a nebulizer, e.g., to generate aerosolized liquid for aerosol delivery. In some embodiments, at least one port can be connected to or interfaced with a processor, which stores and/or analyzes the signal from a biosensor incorporated therein. The processor can transfer the data to computer memory (either hard disk or RAM) from where it can be used by a software program to further analyze, print and/or display the results. In some embodiments, the organ chips can have control ports, e.g., for application of mechanical deformation (e.g., side chambers to apply cyclic vacuum, as in the Lung Chip described herein and in the International Application No.: WO 2010/009307, the contents of which are incorporated herein by reference in their entireties) and/or electrical connections (e.g., for electrophysiological analysis of muscle and nerve conduction).

In some embodiments of any types of organ chips and/or in vitro microphysiological systems described herein, any fluid control elements can be incorporated into the organ chips and/or in vitro microphysiological systems to modulate the fluid flow. For example, bubble traps can be integrated into each organ chip and/or in vitro microphysiological systems to minimize the effects of any bubbles that may form in the pumps, valves, or tubing. In some embodiments, microsensors or biosensors can also be integrated into the organ chips and/or in vitro microphysiological systems for controlling the culture conditions and/or monitoring the response of cells to the culture conditions. Any art-recognized biosensors, e.g., thin enzyme electrodes (Ref. 5) and/or microphysiometers (Ref. 6) can be used in any embodiments of the organ chips and/or in vitro microphysiological systems described herein.

In some embodiments of any types of organ chips described herein, organ chips can be oxygenated either through a porous material used in the construction of the organ chips (e.g., PDMS) or using on-cartridge or systemic gas exchange membranes.

An organ chip can be produced with or without aerosol delivery capabilities. In some embodiments, an organ chip can be adapted to deliver an aerosol, e.g., comprising an active agent described herein, to cells cultured in the channels. Detailed information about various designs and configurations of microfluidic devices for aerosol delivery can be found, e.g., in the International Application No. WO 2012/154834, the contents of which are incorporated herein by reference in their entireties.

As an organ chip is developed to mimic the respective function of an organ, the design of each organ chip can be different according to their respective physiological properties and/or functions. For example, the organ chips can differ in, e.g., but not limited to, cell populations (e.g., cell types and/or initial cell seeding density), internal design, microarchitecture, dimensions, fluidic control, mechanical and electrical control and read-outs depending on the organ type (e.g., Lung Chip versus Heart Chip).

In some embodiments, the organ chips can be designed to have a common shape and have positioned inlets and outlets for delivery of fluids to the Microvascular channels lined by microvascular endothelium and Interstitial fluid channels lined by organ-specific parenchymal cells (e.g., but not limited to, alveolar epithelium, heart muscle, hepatocytes). See, e.g., the section "Examples of organ chips or organ-on-a-chip devices" for exemplary design of various organ chips based in part on the two basic organ chips (e.g., Lung chips and Heart chips) described herein.

Without limitations, different kinds of organ chips described herein can comprise additional cell types, e.g., but not limited to, immune cells, stromal cells, smooth muscle cells, neurons, lymphatic cells, adipose cells, and/or microbiome in gut, based on the goals of the application. By way of example only, if inflammatory response is desired to be studied in a gut or liver model, immune cells can be incorporated into the gut or liver chip accordingly.

Functional assessment of organ chips: The viability and/or function of various organ chips can be generally assessed, e.g., morphologically with optical imaging. In some embodiments, any other art-recognized characterization techniques can be used to determine the function of various organ chips. For example, the alveolar-capillary interface function of the Lung Chip can be measured, e.g., by quantifying permeability barrier function (e.g., using TEER and molecular exclusion), measuring surfactant production, and/or demonstrating physiological relevant responses to cytokines (e.g., ICAM1 expression in response to TNFα). See e.g., Huh D. et al., 2010. Heart muscle function can be characterized, e.g., using force-frequency curves, measuring increases in peak contraction stress as a function of increasing field stimulation frequency, and/or analyzing electrocardiogram results during the same protocol to ensure that the tissues are functioning electrically. See Grosberg A. et al. 2011. Functionality of the Liver Chip can be assessed, e.g., via multiple well established assays including albumin secretion, transporter expression and/or function (efflux and uptake transporters), and/or CYP450 expression. Specific CYP450 enzyme can be determined, e.g., by incubation with FDA approved probe substrates REF1, and specific metabolite formation for each CYP450 isoform can be measured and validated, e.g., using LC/MS. Response of hepatocytes to prototypical CYP450 inducers (e.g., Rifampacin for CYP3A4) can be assessed.

Based on the functional assessments, one of skill in the art can adjust the condition of the organ chips, e.g., by modulating the flow rate of fluid (fluid shear stress), nutrient level, mechanical stimulation, electrical stimulation, cell seeding density on the membranes, cell types, ECM composition on the membrane, dimension and/or shapes of the channels, oxygen gradient and any combinations thereof, to modulate the functional outcome of the organ chips, or the in vitro microphysiological system.

Parenchymal Cells and Vascular Endothelial Cells

Parenchymal cells are selected to suit for specific organ chips. Parenchymal cells are generally the distinct cells of an organ contained in and supported by the connective tissue framework. The parenchymal cells typically perform a function that is unique to the particular organ. In some embodiments, the term "parenchymal" can exclude cells that are common to many organs and tissues such as fibroblasts and endothelial cells within blood vessels.

For example, in a liver organ, the parenchymal cells can include hepatocytes, Kupffer cells, epithelial cells that line the biliary tract and bile ductules, and any combinations thereof. The major constituent of the liver parenchyma are polyhedral hepatocytes (also known as hepatic cells) that presents at least one side to an hepatic sinusoid and opposed sides to a bile canaliculus. Liver cells that are not parenchymal cells include cells within the blood vessels such as the endothelial cells or fibroblast cells.

In striated muscle, the parenchymal cells can include myoblasts, satellite cells, myotubules, myofibers, and any combinations thereof.

In cardiac muscle, the parenchymal cells can include the myocardium also known as cardiac muscle fibers or cardiac muscle cells, the cells of the impulse connecting system such as those that constitute the sinoatrial node, atrioventricular node, atrioventricular bundle, and any combinations thereof.

In a pancreas, the parenchymal cells can include cells within the acini such as zymogenic cells, centoacinar cells, basal or basket cells, cells within the islets of Langerhans such as alpha and beta cells, and any combinations thereof.

In spleen, thymus, lymph nodes and bone marrow, the parenchymal cells can include reticular cells, blood cells (or precursors to blood cells) such as lymphocytes, monocytes, plasma cells, macrophages, and any combinations thereof.

In the kidney, parenchymal cells can include cells of collecting tubules, the proximal and distal tubular cells, and any combinations thereof.

In the prostate, the parenchyma can include epithelial cells.

In glandular tissues and organs, the parenchymal cells can include cells that produce hormones. In the parathyroid glands, the parenchymal cells can include the principal cells (chief cells), oxyphilic cells, and a combination thereof. In the thyroid gland, the parenchymal cells can include follicular epithelial cells, parafollicular cells, and a combination thereof. In the adrenal glands, the parenchymal cells can include the epithelial cells within the adrenal cortex and the polyhedral cells within the adrenal medulla.

In the parenchyma of the gastrointestinal tract such as the esophagus, stomach, and intestines, the parenchymal cells can include epithelial cells, glandular cells, basal cells, goblet cells, and any combinations thereof.

In the parenchyma of lung, the parenchymal cells can include the epithelial cells, mucus cells, goblet cells, alveolar cells, and any combinations thereof.

In the skin, the parenchymal cells can include the epithelial cells of the epidermis, melanocytes, cells of the sweat glands, cells of the hair root, and any combinations thereof.

Cell Sources: The cells (e.g., parenchymal cells and/or vascular endothelial cells) used in the organ chips can be isolated from a tissue or a fluid of subject using any methods known in the art, or differentiated from stems cells, e.g., embryonic stem cells, or iPSC cells, or directly differentiated from somatic cells. In some embodiments, stem cells can be cultured inside the organ chips and be induced to differentiate to organ-specific cells. Alternatively, the cells used in the organ chips can be obtained from commercial sources, e.g., Cellular Dynamics International, Axiogenesis, Gigacyte, Biopredic, InVitrogen, Lonza, Clonetics, CDI, and Millipore, etc.).

In some embodiments, the cells used in the organ chips can be differentiated from the "established" cell lines that commonly exhibit poor differentiated properties (e.g., A549, CaCo2, HT29, etc.). These "established" cell lines can exhibit high levels of differentiation if presented with the relevant physical microenvironment (e.g., air-liquid interface and cyclic strain in lung, flow and cyclic strain in gut, etc.), e.g., in some embodiments of the organ chips.

In some embodiments, the cells used in the organ chips can be genetically engineered for various purposes, e.g., to express a fluorescent protein, or to modulate an expression of a gene, or to be sensitive to an external stimulus, e.g., light, pH, temperature and/or any combinations thereof.

Examples of Organ Chips or Organ-on-a-chip Devices

An in vitro microphysiological system can comprise at least two different organ chips using one or both of the first and second organ chip designs described herein. The first organ chip design is based a microfluidic device comprising: a body comprising a central channel therein, and an least partially porous and at least partially flexible first membrane positioned within the central channel and along a plane, wherein the first membrane is configured to separate the central channel to form two sub-channels, wherein one side of the first membrane is seeded with vascular endothelial cells, and the other side of the first membrane is seeded with at least one type of organ-specific parenchymal cells.

In some embodiments, the first organ chip can further comprise at least a channel wall positioned adjacent to the two sub-channels, wherein the first membrane can be mounted to the channel wall; and an operating channel adjacent to the two sub-channels on an opposing side of the channel wall, wherein a pressure differential applied between the operating channel and the two sub-channels can cause the channel wall to flex in a desired direction to expand or contract along the plane within the two sub-channels.

The second organ chip design is based on a microfluidic device comprising: a body comprising a first chamber enclosing a plurality of muscular thin films adapted to measure contraction of muscle cells, and a second chamber comprising a layer of muscle cells on the bottom surface of the second chamber, wherein the bottom surface is embedded with an array of microelectrodes for recording of action potentials, and wherein the top surface of the second chamber is placed with at least a pair of electrodes for providing electric field stimulation to the muscle cells.

In some embodiments, the second organ chip can further comprise an at least partially porous second membrane positioned within the first chamber to form a top chamber and a bottom chamber, wherein the bottom chamber can comprise the plurality of muscular thin films on its bottom surface, and wherein the surface of the second membrane in contact with the top chamber can be seeded with a layer of epithelial cells.

The design of the first organ chip described herein can provide a basis for development of organ chips to mimic tissue-tissue interfaces, and/or mechanically-active microenvironment. For example, lung chips, liver chips, gut chips, kidney chips, skin chips, brain chips, testis chips, and any combinations thereof, can be constructed based on the first organ chip design with any appropriate modifications.

The design of the second organ chip described herein can provide the basis for development of organ chips where cell contraction, and/or electric field stimulation of the cells are intended. For example, heart chips, skeletal muscle chips, lung airway smooth muscle chips, brain chips, and any combinations thereof can be constructed based on the second organ chip design with any appropriate modifications.

In some embodiments, an organ chip, e.g., a brain chip can employ either or both designs of the first and second organ chips, with any appropriate modifications.

The following examples of organ chips are intended to illustrate applications and/or adaptations of the first organ chip design and/or second organ chip design to construct various organ chips, and should not be construed to be limiting. Any modifications to the organ chips described herein that are within one of skill in the art are also encompassed by the scope described herein.

Lung chips or lung-on-a-chip: The methods, multi-channeled architecture and ability of a Lung Chip (FIG. 1 and FIGS. 2A-2B) to mimic, at least in part, the normal physiology (e.g., normal breathing) of a lung are based on the first organ chip design and has been previously described in Huh D. et al. "Reconstituting organ-level lung function on a chip" Science (2010) 328: 1662, and in the International Application No. WO 2010/009307, the contents of which are incorporated herein by reference in their entireties.

Figure 2B:
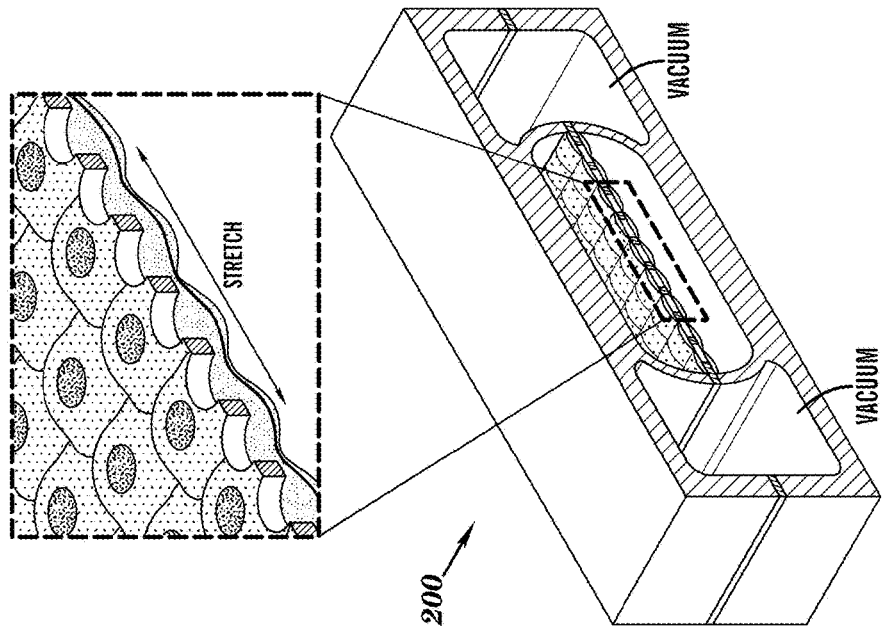
FIGS. 2A-2B are schematic representations of a lung-on-a chip in accordance with one embodiment described herein.
Figure 2A:
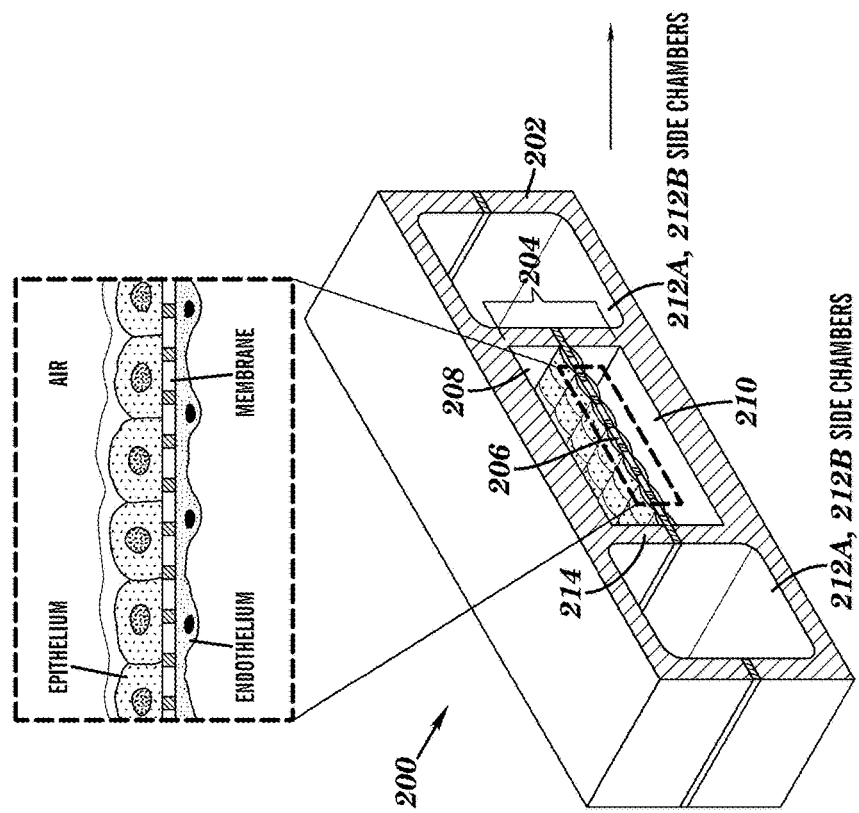

For example, FIGS. 2A-2B shows diagrammatic views of a lung-on-a-chip in accordance with one embodiment described herein. The lung chip can comprise a body 202 having a central microchannel 204 therein; and an at least partially porous and at least partially flexible membrane 206 positioned within the central microchannel 204 and along a plane. The membrane 206 is configured to separate the central microchannel 204 to form a first central microchannel 208 and a second central microchannel 210, wherein a first fluid is applied through the first central microchannel 208 and a second fluid is applied through the second central microchannel 210. There is at least one operating channel (212A, 212B) separated from the first 208 and second 210 central microchannels by a first microchannel wall 214. The membrane 206 is mounted to the first microchannel wall 214, and when a pressure is applied to the operating channel (212A and/or 212B), it can cause the membrane to expand or contract along the plane within the first 208 and the second 210 central microchannels.

In some embodiments, one side of the membrane 206 can be seeded with alveolar epithelial cells to mimic an epithelial layer while another side of the membrane 206 can be seeded with lung microvascular endothelial cells to mimic capillary vessels. Accordingly, lung chips, in some embodiments can be used to mimic an alveolar-capillary unit, which plays a vital role in the maintenance of normal physiological function of the lung as well as in the pathogenesis and progression of various pulmonary diseases.

In such embodiments, a gaseous fluid, e.g., air and/or aerosol, can flow through the first central microchannel 208 in which the alveolar epithelial cells are resided, while a liquid fluid, e.g., culture medium, buffered solution and/or blood, can flow through the second central microchannel 210 (Microvascular channel) in which the microvascular endothelial cells are resided.

Figure 3A:
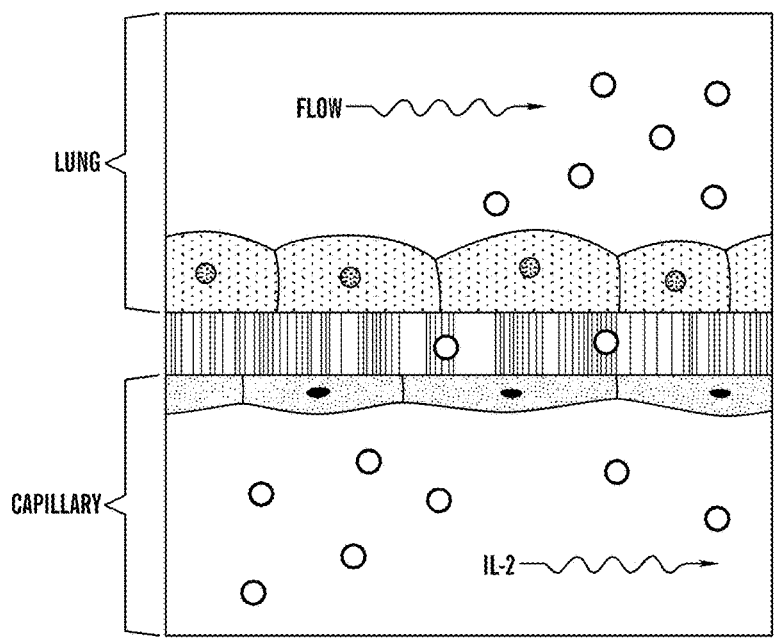
FIGS. 3A-3C shows that human lung-on-a-chip can be used to predict IL-2 chemotherapy toxicity (vascular leakage) responses based on mimicry of the lung's dynamic mechanically-active (breathing) microenvironment.
Figure 3C:
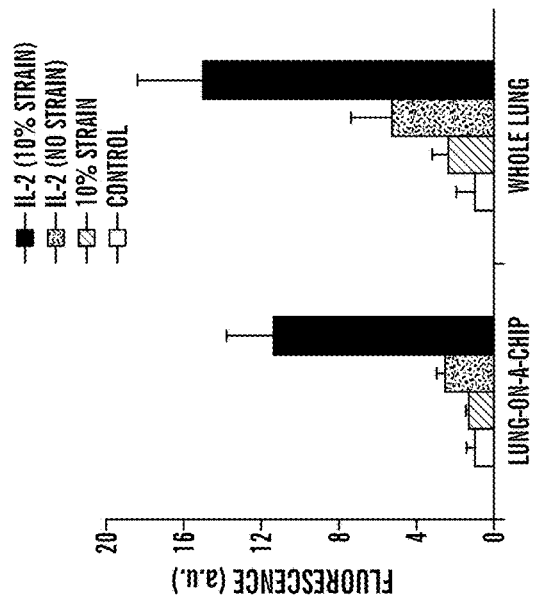
Figure 3B:
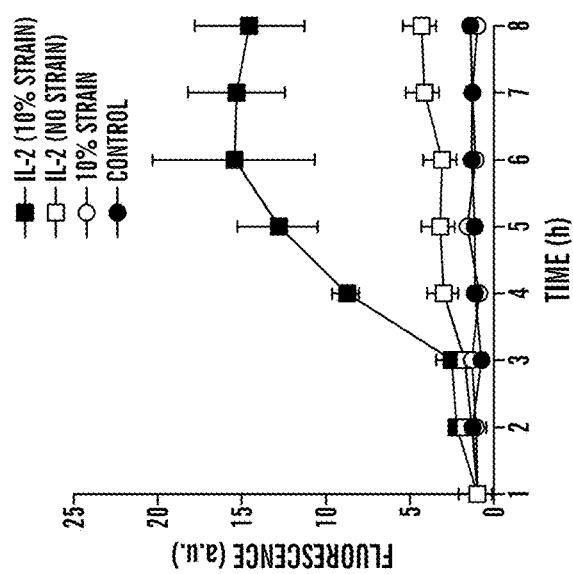

The lung chips can be used to evaluate lung response to an active agent, e.g., but not limited to, immune response to microbial infection and/or inflammatory responses to nanoparticulate toxins. For example, the active agent (e.g., cells including, e.g., but not limited to, bacteria and/or virus, proteins, peptides, antigens, antibodies or portions thereof, enzymes, nucleic acids, siRNA, shRNA, aptamers, small molecules, antibiotics, drugs or therapeutic agents, molecular toxins, nanomaterials or particulates, aerosols, environmental contaminants or pollutants (e.g., but not limited to, microorganisms, organic/inorganic contaminants present in food and/or water, and/or air pollutants), and any combinations thereof) can be added in a liquid fluid flowing through the second central microchannel 210, e.g., to mimic blood carrying the active agent (e.g., cells including, e.g., but not limited to, bacteria and/or virus, proteins, peptides, antigens, antibodies or portions thereof, enzymes, nucleic acids, siRNA, shRNA, aptamers, small molecules, antibiotics, drugs or therapeutic agents, molecular toxins, nanomaterials or particulates, aerosols, environmental contaminants or pollutants (e.g., but not limited to, microorganisms, organic/ inorganic contaminants present in food and/or water, and/or air pollutants), and any combinations thereof). The inventors have demonstrated, in one embodiment, that the lung chips that mimic the lung's dynamic mechanically-active (breathing) microenvironment (e.g., using the device described in the International Application No. WO 2010/009307 in which one embodiment has side channels to allow modulation of pressure to cause cyclic movement of the flexible porous membrane on which the cells are seeded) can effectively predict lung toxicity responses to the chemotherapeutic cytokine, e.g., IL-2, which has a dose-limiting toxicity due to vascular leakage leading to pulmonary edema in humans. Using the lung-on-a-chip with a detectable marker, e.g., fluorescent-insulin as a marker of vascular permeability (fluid shifts), the IL-2 produces a small but significant increase in pulmonary vascular leakage into the air channel of the lung chip under static conditions. However, with physiological breathing motions akin to normal breathing motions (10% cyclic strain), this response is increased by more than 3-fold (and it was accompanied by blood clot formation as seen in humans), and the critical physiological importance of providing this correct mechanical microenvironment was demonstrated in studies in a mouse ex vivo ventilation-perfusion model that demonstrated a similar dependency of pulmonary edema induction by IL2 on breathing motions (FIG. 3). Using the lung chips, various kinds of drugs or candidate agents can be tested to determine what would be the effective treatment. In fact, the IL2-induced pulmonary toxicity in the lung chip can be pharmaceutically suppressed in vitro. These results provide proof-of-principle for organ chips lined by human cells (e.g., organ-specific parenchymal cells) as a means to predict clinically relevant toxicity responses in humans.

In some embodiments, the microchannel intended for a gaseous flow, e.g., the first central microchannel 208 allowing air to flow through, can be configured to permit delivery of aerosolized micro-droplets (e.g., aerosolized drugs, and/or nanoparticles or particulates). Detailed information about various designs and configurations of microfluidic devices for aerosol delivery can be found, e.g., in the International Application No. WO 2012/154834, the content of which is incorporated herein by reference in its entirety, and can be adopted in the lung chips to deliver aerosolized microdroplets, e.g., to study toxicities of nanoparticles in lungs. Similar findings in relation to the toxicities of nanoparticles has been observed using the lung chips, indicating that some clinically organ toxicities cannot be mimicked in vitro without providing the correct mechanical microenvironment, which is generally lacking from traditional in vitro model systems.

Heart chips: The methods, architecture and ability of a Heart Chip (e.g., FIG. 8) to mimic, at least in part, the normal physiology (e.g., cell contraction) of a heart are based on the second organ chip design described herein. Heart Chips are described, for example, in U.S. Provisional Patent Application Ser. No. 61/569,028, filed on Dec. 9, 2011, U.S. Provisional Patent Application Ser. No. 61/697,121, filed on Sep. 5, 2012, and PCT patent application titled "Muscle Chips and Methods of Use Thereof," filed on Dec. 10, 2012 and which claims priority to the US provisional application nos. 61/569,028, filed on Dec. 9, 2011, U.S. Provisional Patent Application Ser. No. 61/697,121, the entire contents of all of which are incorporated herein by reference in their entireties.

In order to fabricate heart chips to mimic tissue organization, in some embodiments, functional heart tissues can be fabricated first and then multiplexed in a microfluidic device. For example, functional heart tissues can be fabricated by culturing ventricular cardiomyocytes (e.g., neonatal rat ventricular cardiomyocytes) on elastomeric polymer thin films micropatterned with cell adhesion proteins (e.g., extracellular matrix proteins) to promote spatially ordered, two-dimensional myogenesis and create "muscular thin films" (MTFs) as described previously, e.g., in Grosberg A. et al. "Ensembles of engineered cardiac tissues for physiological and pharmacological study: Heart on a chip" Lab on a chip (2011) 11: 4165, as well as the International Application Nos. WO 2008/045506, WO 2010/011407 and WO2010/042856, the contents of which are incorporated herein by reference in their entireties. These heart tissue constructs are electrically functional and actively contractile, generating stresses comparable to those produced by whole papillary muscle.

Figure 4A:
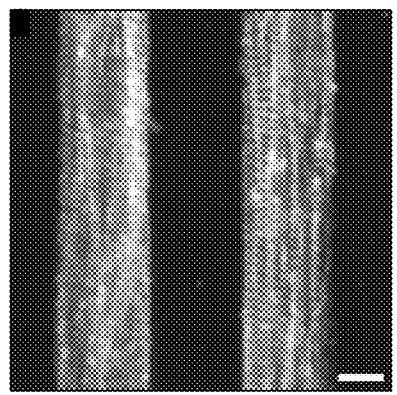
FIGS. 4A-4D is a set of images showing that a contractile heart (muscle) chip mimics tissue organization (FIG. 4A) in a multiplexed array of "muscular thin films" (MTFs) within a microfluidic device (FIGS. 4B and 4C), which can be used to quantitate contractile stress in real-time (FIG. 4D).
Figure 4B:
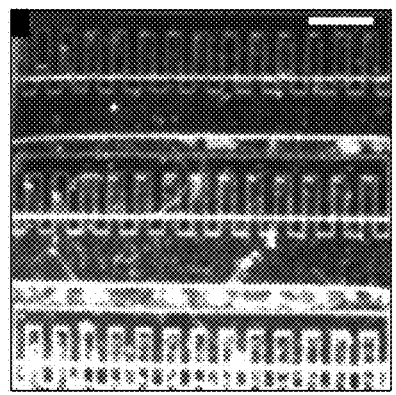
Figure 4C:
Figure 4D:
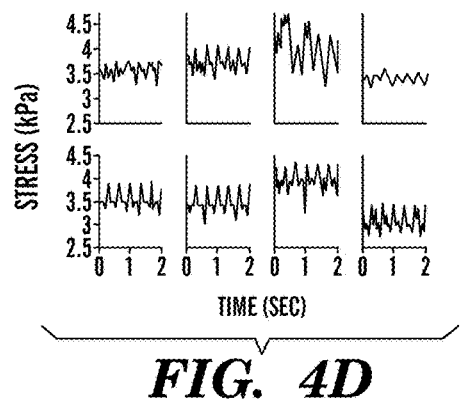
Figure 5:
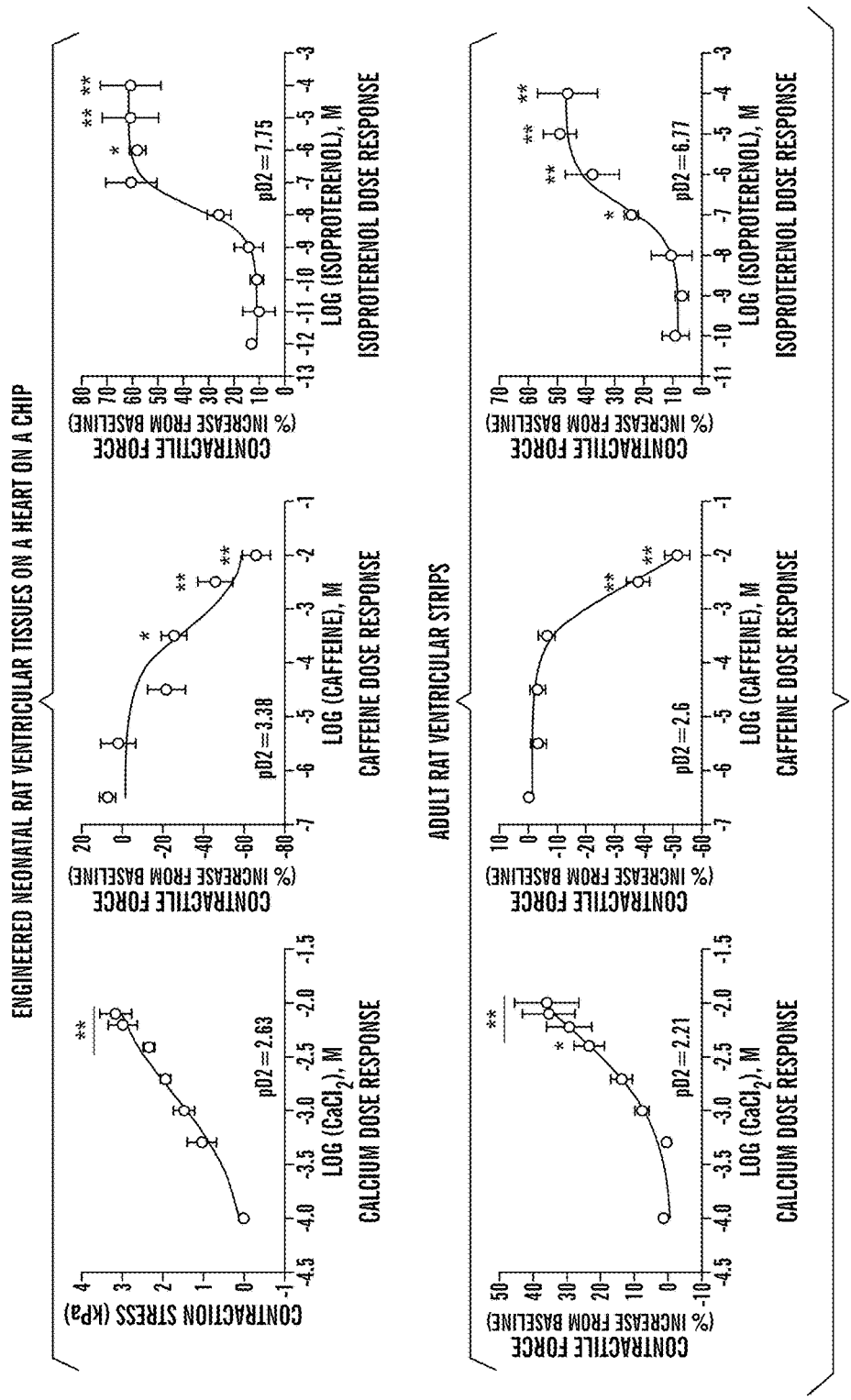
FIG. 5 is a set of line graphs showing that "muscular thin films" MTFs mimic whole heart tissue drug responses. Top row shows the dose response of engineered neonatal rat ventricular tissues in the form of muscular thin films on the heart chip, treated with calcium (left), caffeine (middle), and isoproterenol (right). The bottom row shows the corresponding responses of adult rat ventricular strips.
Figure 6:
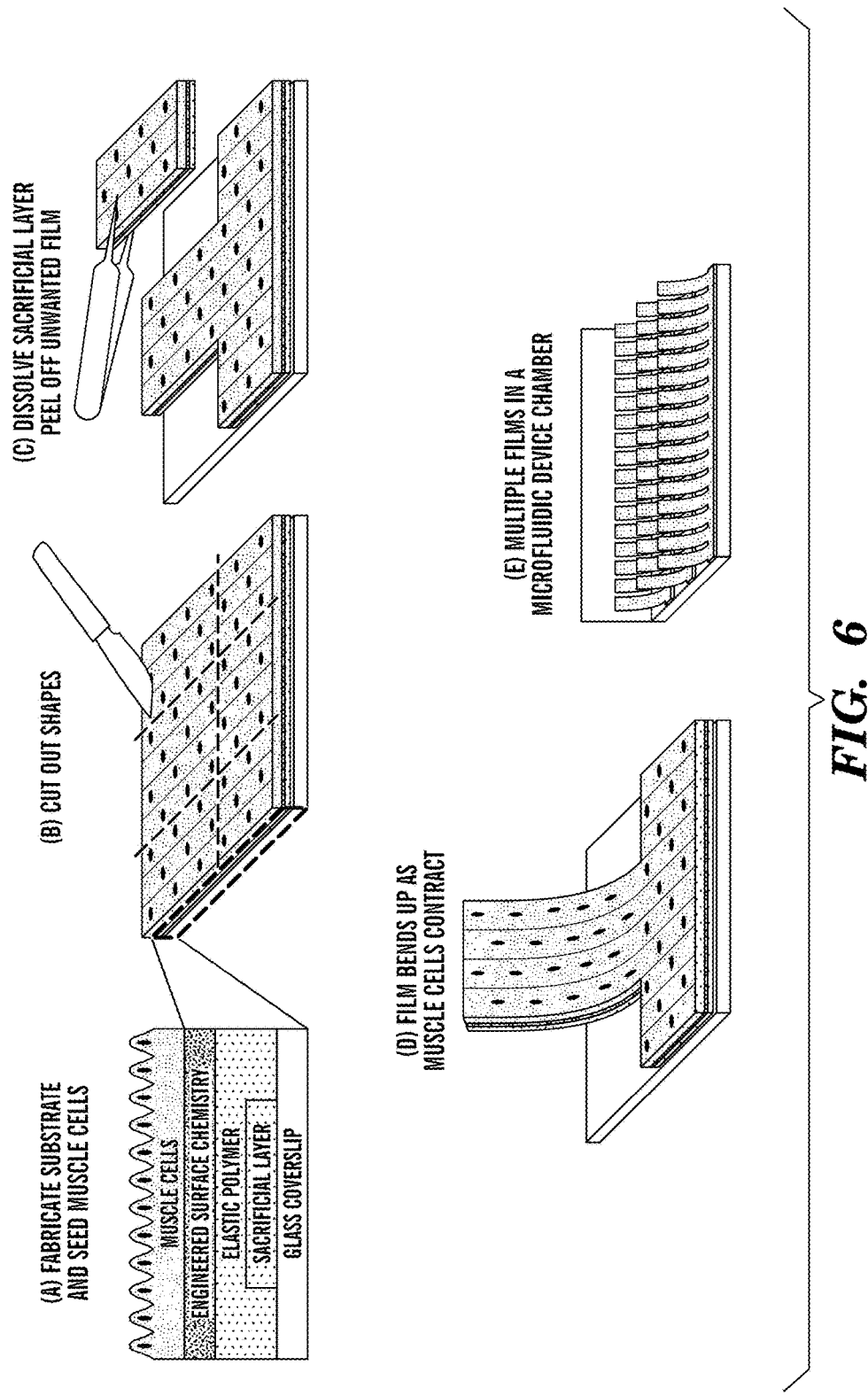
FIG. 6 is a schematic representation showing a series of exemplary assembly steps for one embodiment of a muscular thin film contractility assay based on a PDMS thin film.
Figure 7:
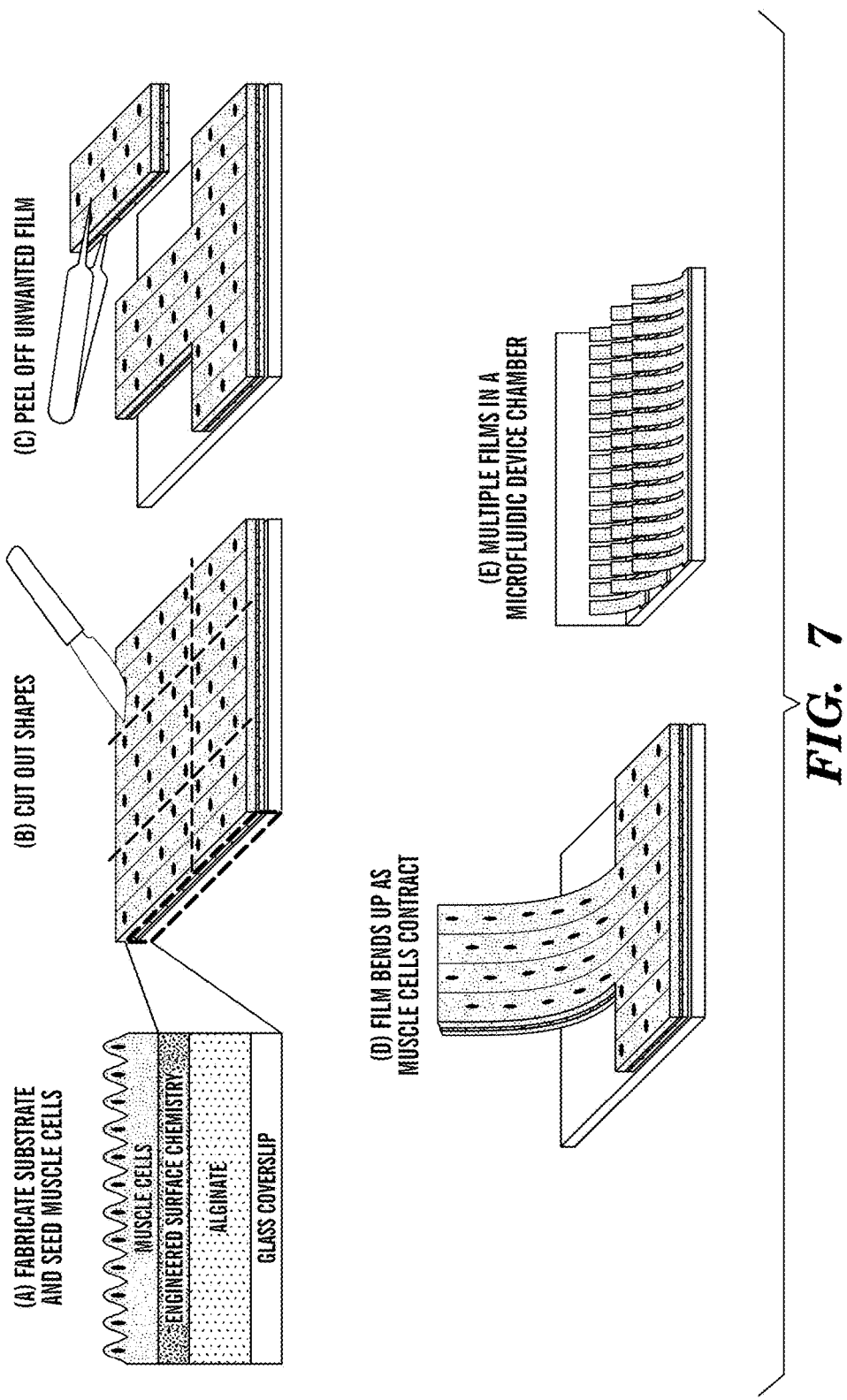
FIG. 7 is a schematic representation showing a series of exemplary assembly steps for one embodiment of a muscular thin film contractility assay based on a patterned alginate thin film.

As used herein, the terms "muscular thin film" and "MTF" are used interchangeably herein and refer to a two-dimensional biopolymer substrate comprising heart muscle cells such as ventricular cardiomyocytes or progenitor cells, which can cause the substrate to bend and form a three-dimensional (3D) structure when the cells contract, e.g., as shown in FIG. 6 or FIG. 7. The MTFs (e.g., at least about 2, at least about 3, at least about 4, at least about 5, at least about 6, at least about 7, at least about 8, at least about 9, at least about 10, at least about 20, at least about 30, at least about 40, at least about 50 or more MTFs) can then be multiplexed, e.g., in an array, within a microfluidic chip (FIGS. 4B-4C). The MTFs can be used to measure effects on heart cell contractile function in vitro during electrical and pharmacological stimulation (Grosberg et al., 2011, FIG. 5).

In another embodiment, multi-layered heart chips can be constructed. For example, a multi-layered heart chip can comprise a body having a 'Microvascular Channel' lined by endothelium (e.g., human endothelial cells) adherent to a porous membrane that separates the Microvascular Channel from the MTF-lined 'Interstitial Channel', such as similar to the configuration of the lung chip as shown in FIG. 2, but without side chambers. The inventors have demonstrated that microengineered MTFs effectively mimic pharmacological responses of adult rat papillary muscle strips (FIG. 5), which are commonly used to screen cardiac tissue responses to drugs by the pharmaceutical industry.

Figure 8:
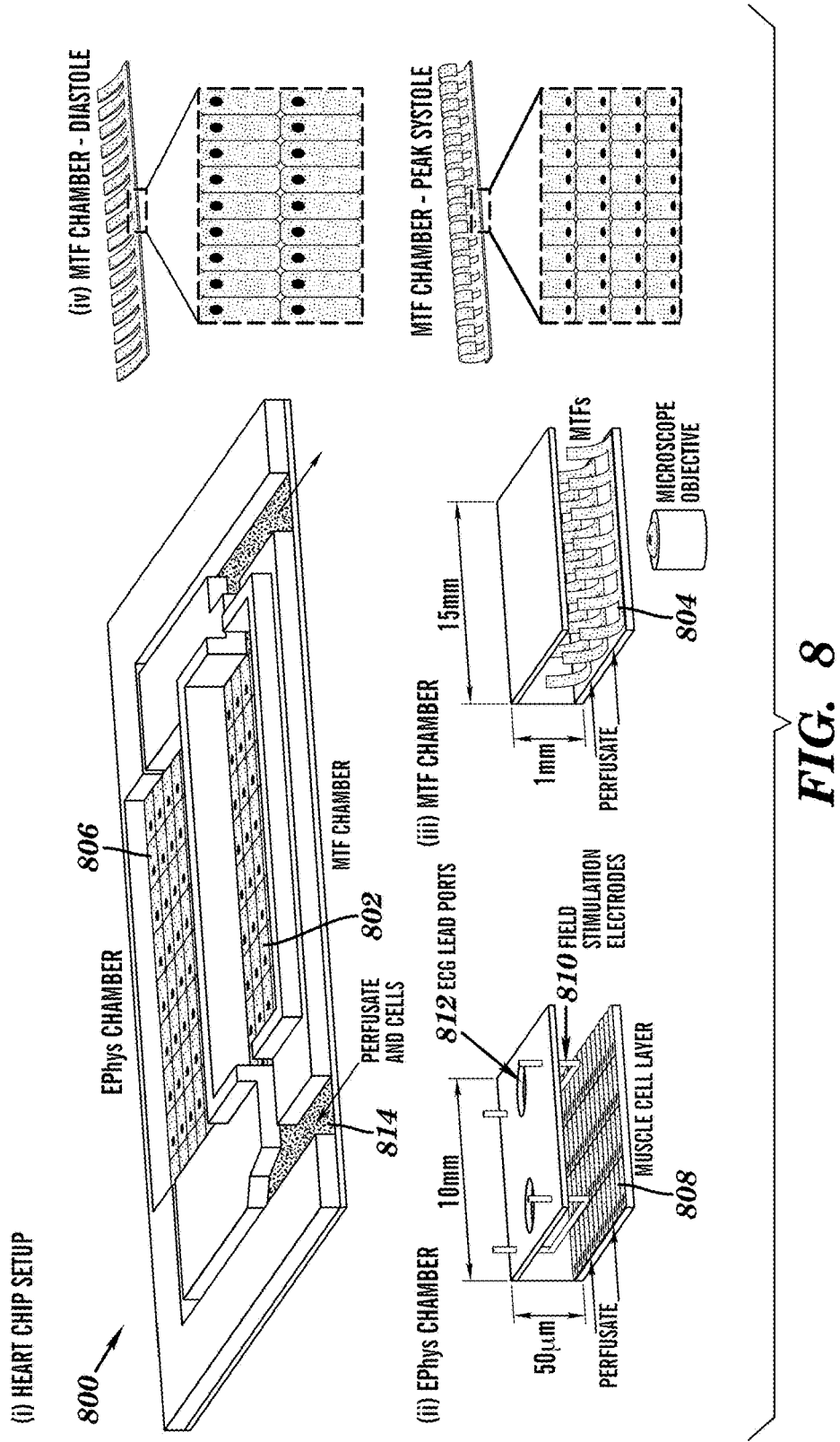
FIG. 8 is a schematic diagram showing exemplary features of a heart chip according to one embodiment described herein. (i) depicts a dual-chamber system with a single medium stream that feeds 2 chambers: an electrophysiological (EPhys) chamber and a MTF chamber; (ii) shows that the EPhys chamber can allow electrophysiological recordings on a monolayer of cardiac muscle in a low volume chamber with micro-electrodes embedded in the bottom of the chamber; (iii) illustrates that a larger chamber situated next to the EPhys chamber can allow high throughput contractility measurements using an array of muscular thin films; (iv) shows that the MTF chamber consists of an anisotropic layer of cardiac myocytes cultured on laser-cut horizontal MTFs whose radius of curvature can be measured optically.
Figure 10A:
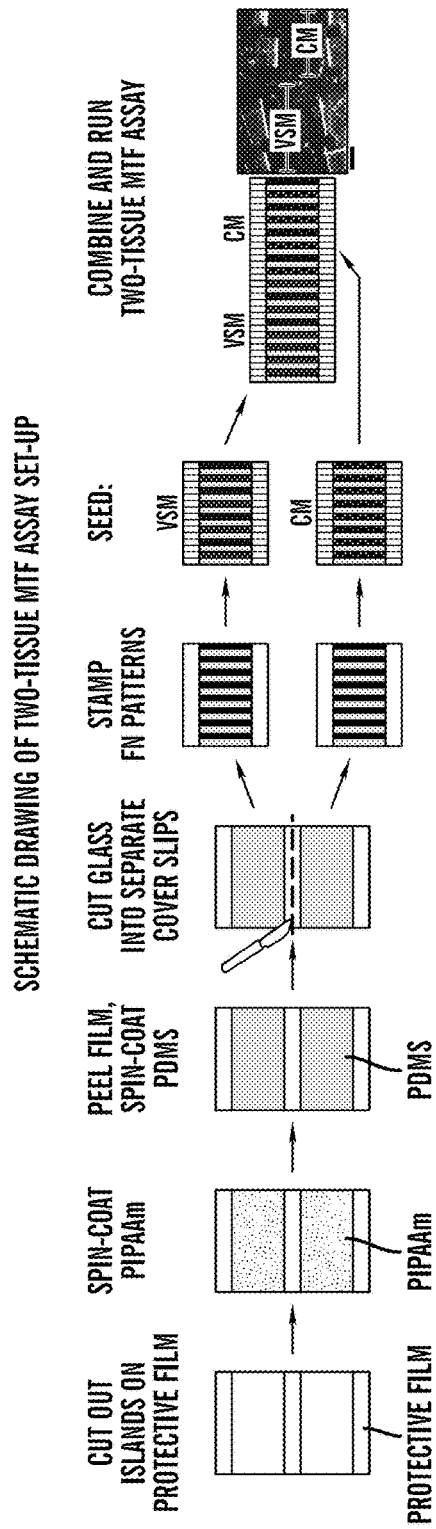
FIGS. 10A-10D is a set of data showing physiological responses of human vascular smooth muscle (VSM) and engineered rat cardiac muscle (CM) on the same chip to drugs determined by a MTF assay.
Figure 10B:
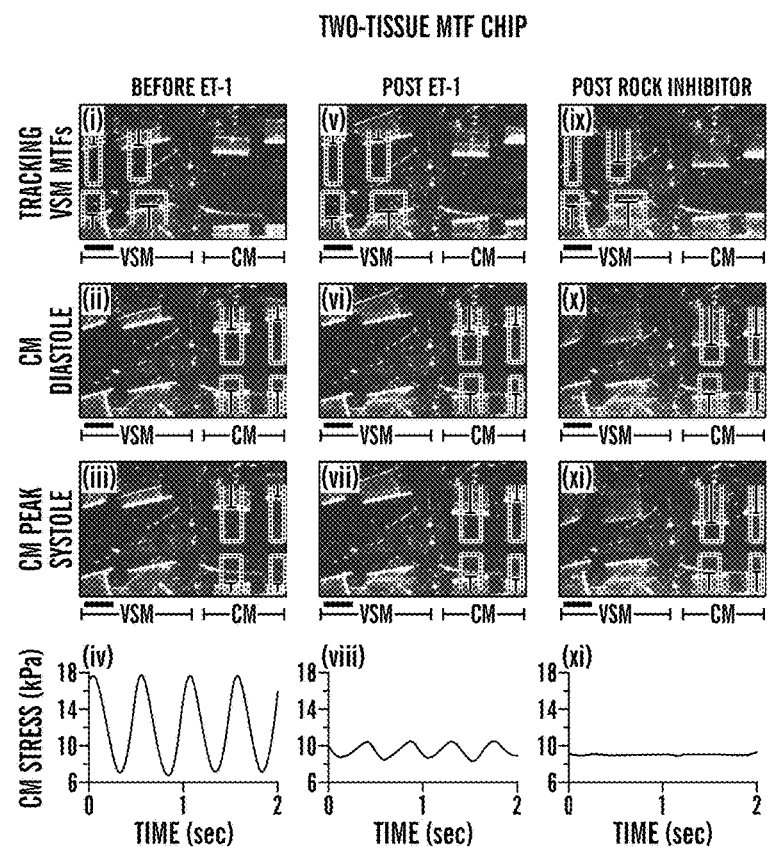
Figure 10C:
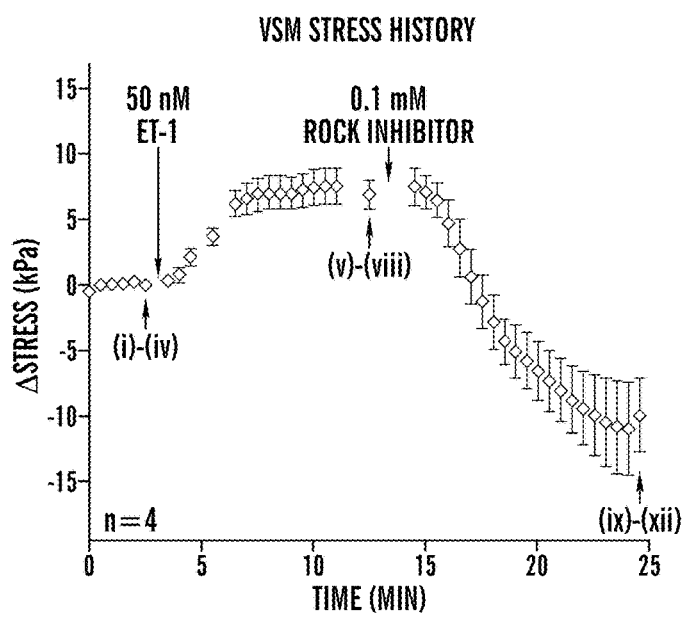
Figure 10D:
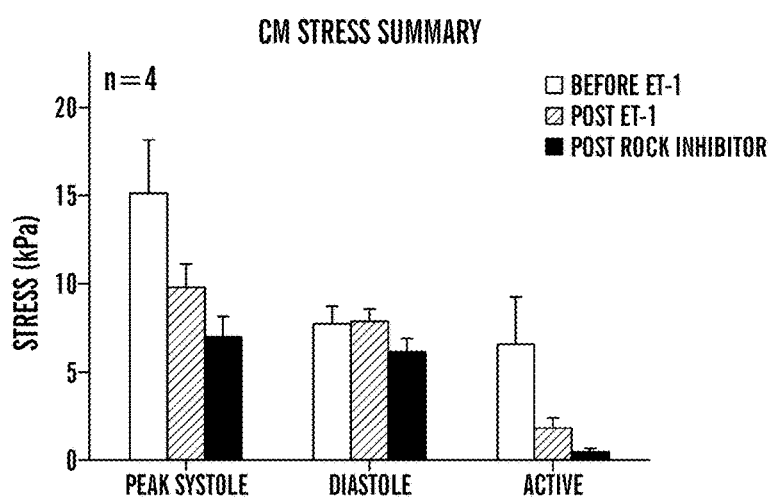

In some embodiments, the heart chips can be modified for various analyses. For example, as shown in FIG. 8, the heart chips 800 can have at least one set of MTF (804)-lined Interstitial Channels (including at least 2 sets, at least 3 sets, at least 4 sets, at least 5 sets or more) to form a MTF Chamber 802, e.g., for optical imaging and contractility analysis of cells exposed to a culture medium with or without an active agent described herein, e.g., by optical measurements of radius of curvatures or projected length of MTFs using microscopy. By way of example only, a curled or contracted MTF can have a smaller projected length than a relaxed MTF, e.g., as shown in FIG. 8 (iv).

To create a MTF chamber, by way of example only, a laser engraving process, e.g., as shown in FIG. 6, can be utilized to cut PDMS thin films of cardiomyocytes cultured as described above; followed by microcontact-printing ECM proteins and enclosing the assembly in a microfluidic chamber. Alternatively, the thin films of cardiomyocytes can be produced with alginate (FIG. 7). To operate a MTF chamber, muscle cells can be cultured on the thin films and the contractile stresses can be assessed by optically monitoring the extent of curvature of the muscular thin films as noted above (FIG. 8). An alternative strategy for measuring contractility is depicted in FIG. 9, where instead of making MTFs, the muscle cells can be grown on a wrinkling substrate 902, e.g., a polyurethane membrane, such that as the muscle cells contract, the substrate deforms. In this embodiment, the wrinkling substrate can further comprise a plurality of holes 904 (e.g., a swiss cheese-like polyurethane membrane) to facilitate optical detection of the substrate deformation due to muscle cell contraction. For example, the holes within the substrate can remain as a circle when the muscle cells are relaxed, but the circle becomes deformed, e.g., becoming an oval, or an ellipse, due to muscle cell contraction.

The dimensions of the MTF chamber can be suited for a user's need. For example, the length of the MTF chamber can vary from about 5 mm to about 100 mm, or from about 10 mm to about 50 mm, or from about 10 mm to about 25 mm. In one embodiment, the length of the MTF chamber can be about 15 mm. The height of the MTF chamber can be adjusted, e.g., based on the size of MTFs. For example, the height of the MTF chamber is designed to be sufficient to permit the MTFs to freely bend or curl up without any spatial constraint. In some embodiments, the height of the MTF chamber can be about 0.5 mm to about 5 mm, or about 0.5 mm to about 3 mm. In one embodiment, the height of the MTF chamber can be about 1 mm.

In some embodiments, the heart chips, e.g., the Interstitial Channels can further comprise any heart-specific parenchymal cells, e.g., but not limited to cardiomyocytes and/or vascular smooth muscle cells, to further mimic the physiological environment and/or function of the heart. In some embodiments, a heart chip can be a microfluidic device in which mature cardiomyocytes (e.g., human cardiomyocytes) are cultured on a 2D polymer substrate (e.g., PDMS substrates or micromolded alginate substrates) to form MTFs. In some embodiments, the heart chips can have both vascular smooth muscle and cardiac muscle cultured on the same chip (see FIG. 10), e.g., to form to different kinds of muscles, e.g., smooth muscles vs. striated muscles.

The cardiomyocytes can be isolated from a tissue of a subject or obtained from a commercial source, or by differentiating stems cells to cardiomyocytes, e.g., induced pluripotent stem cell-derived cardiomyocytes. Cardiomyocytes (e.g., human cardiomyocytes) can be obtained from a commercial source, e.g., from Axiogenesis, CDI, Vistagen, Coriell, Reprocell. The culture conditions can be optimized for each source of cardiac myocytes, e.g., ES- or iPS-derived cardiac myocytes, neonatal rat or mouse myocytes. The human cardiomyocytes can be obtained or derived from different origins (e.g., ventricular, atrial, etc.). In some embodiments, the cardiomyocytes of different origins can be co-cultured. In some embodiments, the cardiomyocytes can be engineered to be photosensitive (e.g., cardiomyocytes expressing a photosensitive membrane transport mechanism that is responsive to light of a particular wavelength). See, e.g., the International Appl. No. WO 2012/006320, the content of which is incorporated herein by reference in its entirety, for information about fabrication of photosensitive cardiac rhythm modulation systems, which can be integrated into the heart chips described herein.

To fabricate an in vitro myocardial construct that recapitulates the structural complexity of the human heart chambers, in one embodiment, aligned or anisotropic monolayers of muscle cells (e.g., a monolayer of cardiomyocytes with a laminar organization) can be cultured on microcontact printed biocompatible substrates (e.g., PDMS substrates, microcontact printed polyurethane membranes and micromolded alginate substrates) within a microfluidic device, e.g., being integrated into a MTF chamber for contractility measurements and/or a low volume Electrophysiological Chamber (or an Electrophysiological Chamber) as described below.

In some embodiments, the heart chips 800 can further have at least one another set of Interstitial Channels (including at least 2 sets, at least 3 sets, at least 4 sets, at least 5 sets or more) lined with a heart muscle cell layer under which are embedded with at least one or a plurality (e.g., an array) of microelectrodes (e.g., platinum microelectrodes) 808 (microelectrodes are placed underneath the cells), while the side of the channel opposing the heart muscle cell layer is placed with at least one or more (e.g., at least two or more) electric field stimulation electrodes 810 to form an "Electrophysiological Chamber" 806 (see, e.g., FIG. 8). In such embodiments, the Electrophysiological Chamber 806 can further comprise an electrocardiography (ECG) lead port 812 for connection with an ECG lead (or a lead electrocardiogram) to measure and/or monitor electrical pacing and/or analysis of changes in cardiac electrical potential.

To fabricate an Electrophysiological (EPhys) Chamber 806, an anisotropic muscle cell monolayer can be cultured in a low volume chamber. Then, the muscle cells can be electrically field stimulated using the electrodes 810 on the top, and action potentials can be recorded using the microelectrode array 808 on the bottom, where the microelectrode array is placed underneath the muscle cells cultured on the bottom surface. The electrode readouts can be calibrated with the action potential characteristics of the cardiomyocyte monolayer.

The dimensions of the Electrophysiological Chamber can be suited for a user's need. For example, the length of the Electrophysiological Chamber can vary from about 5 mm to about 100 mm, or from about 8 mm to about 50 mm, or from about 10 mm to about 25 mm. In one embodiment, the length of the Electrophysiological Chamber can be about 10 mm. The height of the MTF chamber can be adjusted, e.g., based on the size of field stimulation electrodes. For example, the height of the MTF chamber is designed to be sufficient to permit the MTFs to freely bend or curl up without any spatial constraint. In some embodiments, the height of the MTF chamber can be about 0.5 mm to about 5 mm, or about 0.5 mm to about 3 mm. In one embodiment, the height of the MTF chamber can be about 1 mm.

The electrophysiological chamber 806 can be placed anywhere relative to the MTF chamber 802. In some embodiments, the electrophysiological chamber 806 can be placed in parallel to the MTF chamber 802. In some embodiments, the MTF chamber can be larger than the Electrophysiological Chamber to permit high throughput contractility measurements.

While the Electrophysiological 806 and MTF 802 Chambers can each be independently fed by a separate culture medium stream, in some embodiments, both the Interstitial Channels in the MTF and Electrophysiological Chambers can be fed by a single medium stream 814. In some embodiments, the culture medium can be introduced directly through the Interstitial Channels in the Electrophysiological and MTF chambers and/or introduced through an underlying endothelium-lined Microvascular Channels, e.g., in a configuration similar to the lung chips (see, for example, FIG. 2). The presence of the endothelium and its basement membrane lining the microvascular channel on the opposite side of the membrane, plus the ability to perfuse different media compositions through the Interstitial versus Microvascular Channels can allow different experimental conditions for various applications.

In some embodiments, the heart chips can comprise a MTF chamber and an EPhys chamber situated next to each other, for example, as shown in FIG. 8.

In some embodiments, the heart chip can be adapted to fluidically connected upstream and/or downstream to at least one or more organ chips (e.g., but not limited to lung chips or liver chips).

Prediction/determination and validation of pharmacological effects: The heart chips described herein can be used to determine pharmacological effects on heart-specific cells cultured therein. For example, the heart-specific cells can be exposed to an active agent (e.g., cells including, e.g., but not limited to, bacteria and/or virus, proteins, peptides, antigens, antibodies or portions thereof, enzymes, nucleic acids, siRNA, shRNA, aptamers, small molecules, antibiotics, drugs or therapeutic agents, molecular toxins, nanomaterials or particulates, aerosols, environmental contaminants or pollutants (e.g., but not limited to, microorganisms, organic/inorganic contaminants present in food and/or water, and/or air pollutants), and any combinations thereof) by adding the active agent in a culture medium flowing through the Interstitial Channels and/or Microvascular Channels. In some embodiments where the heart chip comprises an Electrophysiological Chamber, electrophysiological information can be collected within the chip, which can be in turn modeled with a user-defined algorithm to estimate an ECG. The ECG can then be correlated with reference data (e.g., current in vitro and outputs, or control outputs, e.g., outputs of cells not exposed to the active agent). In one embodiment, the radius of curvature of the contracting MTFs within the chip can be modeled to estimate the stresses exerted by the cells. The MTF contractility measurements can then be correlated with reference data (e.g., current in vitro and clinical outputs, or control outputs, e.g., outputs of cells not exposed to the active agent).

To validate the heart chips for assessment of pharmacological effects, known drugs within the system can be used, such that the response of the heart chips can be correlated with clinical response to the known drugs. In some embodiments, the cardiac myocytes inside the heart chips can be exposed to drugs that are known to be cardio-safe (e.g., ibuprofen and fexofenadine), e.g., to show that they have no toxic effects on engineered myocardial tissue constructs. In some embodiments, the cardiac myocytes inside the heart chips can be exposed to drugs that are cardiotoxic (e.g., doxorubicin, trastuzumab, terfenadine). For example, doxorubicin (anthracycline family of chemotherapeutics) generally displays cardiotoxic effects primarily by inducing dilated cardiomyopathy, predominately affect the ventricles with some left atrial involvement. Trastuzumab is a monoclonal antibody to HER2 receptor used for the treatment of (HER2+) breast cancers, has been shown to decrease left ventricular ejection fraction. Terfenadine is antihistamine formerly used to treat allergic conditions that was found to be cardiotoxic because it binds hERG channels and causes long QT syndrome. Sorafenib and sunitinib are tyrosine kinase inhibitors used as chemotherapeutic agents that cause poorly characterized cardiotoxic effects that usually manifest as decreased left ventricular ejection fraction and increased cardiac enzymes.

Exemplary applications of heart chips: Although various drug toxicities can affect myocytes with distinct mechanisms, most of the drugs can adversely affect cardiac contractility and ultimately the ability of the heart to pump blood. Therefore, by measuring the contractility and/or electrophysiological output of the heart chip, one can quantitatively measure the impact of various active agents on heart performance. Further, the chambers of the heart are imperative to its function, as the ventricles of the heart are tasked with overcoming pulmonary and system vascular resistance and after load. For example, drugs such as doxorubicin and trastuzumab (as noted above) generally demonstrate ventricular toxicity; thus, some embodiments of the heart chips described herein can be used to mimic the contractile action of these chambers (e.g., ventricular chambers) in vitro. In some embodiments, the heart chip can be a microfluidic device that can measure electrophysiology and/or contractile performance of engineered myocardial tissues. In some embodiments, the heart chip can be a microfluidic device that can measure electrophysiology and/or contractile performance of myocardial tissues derived or obtained from a subject, e.g., to determine an appropriate treatment regimen for the specific subject.

In some embodiments, the heart chips can be used as disease models, e.g., to assess different physiological effects of pharmaceutical or active agents. Examples of the effects that can be assessed using the heart chips can include, without limitations, (1) metabolic: for example, antibody-based medications such as Trastuzumab, which is generally used to treat HER2+ breast cancer, are known to affect ATP production in myocytes through adverse effects on mitochondria (Ref. 7); (2) structural: for example, anti-proliferative agents such as doxorubicin, which is used for a wide variety of malignancies, can adversely affect myocyte growth and mass maintenance (Ref. 8); and (3) ion channel (arrhythmia-inducing): for example, hERG channel binding of many drugs (e.g. albuterol) can generally increase action potential duration, leaving the heart susceptible to arrhythmia (long QT syndrome) and effects on other ion channels (Na, Ca), with concurrent effects on PR prolongation, conduction abnormalities and arrhythmias. While there are in vitro models exist for hERG channel binding assays (Ref. 9), there is a lack of in vitro assays for evaluating drugs exerting metabolic and/or structural effects that can deliver quantitative data relating to cardiac function. Accordingly, a robust in vitro system that can recapitulate the heart can provide a platform to screen a large number of compounds for toxicity, a feat not possible with current in vivo animal models or existing in vitro models.

Since tissue architecture can be controlled within heart chips, which can in turn affect contractile efficiency, various disease states can be created accordingly. Drug toxicity (e.g., Trastuzumab or Doxorubicin) can affect the ability of cardiac myocyte contractility. Thus, in one embodiment, drug toxicity can be determined by measuring contractility of cardiac myocytes within the heart chips. For example, contractility can be read out via optical tracking of MTF deformation/optical tracking of membrane deformation as described above. Optionally, electrophysiological recordings can be taken via a lead ECG. In some embodiments, biomarkers of muscle damage such as creatine kinase and troponin can also be measured. For example, the level of biomarkers can be measured in the culture medium upon exposure to the cells.

In some embodiments, the heart chips can be used for PK/PD modeling (including prediction of pharmacological effects).

Generally, the design of other organ chips can be developed based on the basic designs of the Lung or Heart chips as described herein. For example, without being construed to be limiting, Gut chips, Kidney chips, Liver chips, Skin chips and Testis chips can be developed, e.g., based on the basic design of the Lung chips, while Skeletal Muscle chips, Airways Smooth Muscle chips can be developed, e.g., based on the design of the Heart chips. Depending on different organs, each organ chip can then be incorporated with respective tissue-specific parenchymal cell (e.g., human parenchymal cell) layers within the Interstitial Channel (as described earlier) exposed to their physiological microenvironment (e.g., alveolar epithelium and skin epidermis exposed to air, gut epithelium facing a fluid filled lumen, etc.) on one surface of the ECM-coated porous membrane, with organ-specific vascular endothelium (e.g., human vascular endothelium) on the opposite side lining the Microvascular Channel. Organ-specific differences in the mechanical microenvironment can also be mimicked by altering control and/or process parameters, e.g., but not limited to, flow rates, fluid shear stresses, cyclic mechanical strain, ECM composition, and/or compartment dimensions.

Liver chips: In some embodiments, a mammalian liver chip (e.g., a human liver chip) can be developed and/or modified, e.g., from the basic Lung Chip multichannel design described herein (e.g., as shown in FIG. 2) as well as in Huh D. et al., 2010 and/or in the International Application No. WO 2010/009307, the contents of which are incorporated herein by reference in its entirety. For example, commercially available human hepatocytes (e.g., from Invitrogen) or patient-specific hepatocytes (isolated from a tissue) can be placed on one side of the ECM (e.g., but not limited to, laminin, type IV collagen or Matrigel)-coated membrane, and human microvascular endothelial cells on the other side. Without wishing to be bound by theory, the porous membrane, basement membrane and cell-cell junctions of the endothelium can facilitate physiologically relevant mass transport while protecting hepatocytes from fluid shear stress and serum components in the Microvascular Channel.

In some embodiments, the liver chips can further comprise other parenchymal cells, such as Kupffer cells (resident macrophages of the liver) under the endothelium in the Liver Chip.

Without wishing to be bound by theory, oxygen gradients are essential determinants of normal liver physiology and function, as well as key contributors to acute and chronic hepatoxicity. Accordingly, in some embodiments, oxygen gradients found in vivo can be incorporated in the liver chips. By way of example only, oxygen gradients can be generated in a liver chip, e.g., by using a gas-permeable membrane material, e.g., PDMS which is permeable to gases) and flowing oxygen at different concentrations through the two side channels separated by the membrane. Other art-recognized microengineering methods, for example, as described in Adler M. et al. Lab Chip 2010; 10(3): 388-389 and Chen Y-A et al., Lab Chip 2011; 11: 3626-3633, can also be used to develop oxygen gradients within the organ chips.

In some embodiments, bile canalicular networks in predetermined patterns (e.g., by art-recognized micropatterning techniques) can be integrated into liver chips, such that they can be coupled with microscale sampling ports in the liver chips. Such configuration can be used to determine intrinsic biliary clearance. This approach can be used to facilitate analysis of interplay between drug transporters and drug metabolizing enzymes, which is a key determinant of drug PK properties and toxicity profiles in humans.

Figure 11A:
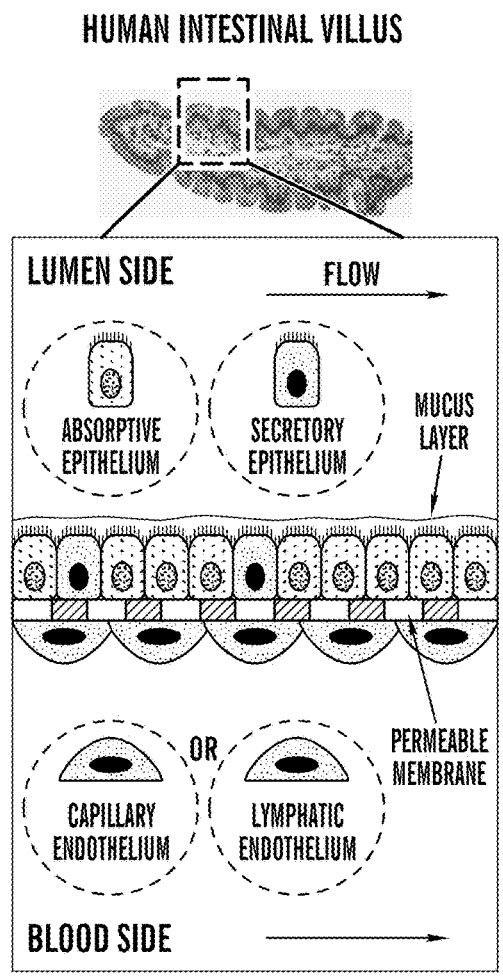
FIGS. 11A-11F are images showing a human gut chip according to one embodiment described herein.
Figure 11B:
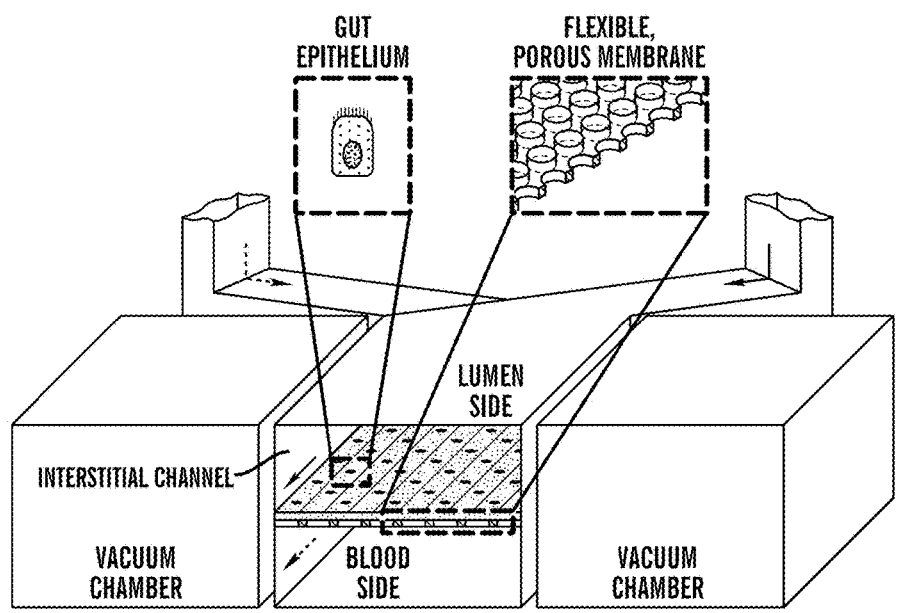
Figures 11C, 11D:
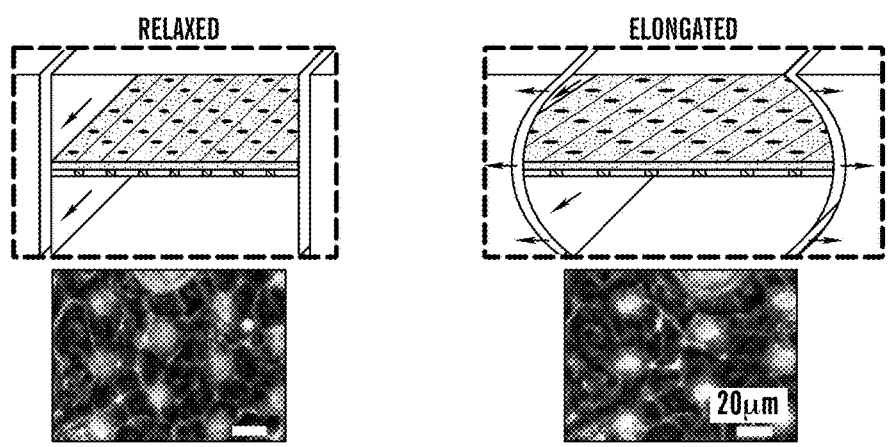
Figure 11E:
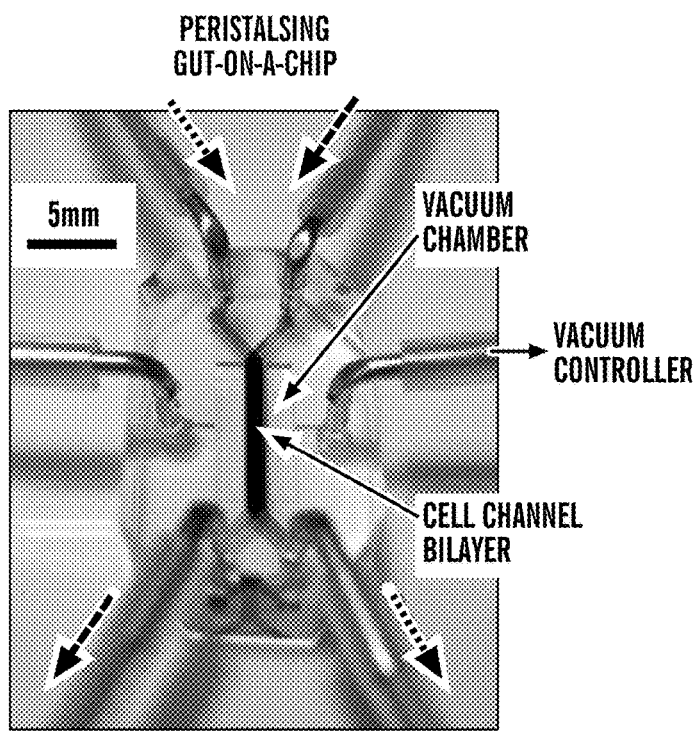
Figure 11F:
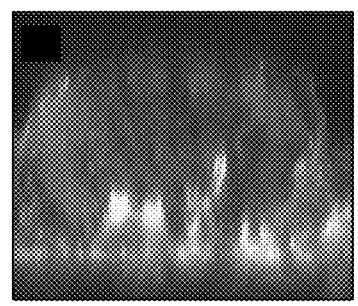

Gut Chips: In some embodiments, the gut chips, e.g., as shown in FIG. 11, can be developed and/or modified, e.g., from the basic Lung Chip multichannel design described herein (e.g., as shown in FIG. 2) as well as in Huh D. et al., 2010 and/or in the International Application No. WO 2010/009307, the contents of which are incorporated herein by reference in their entireties. In some embodiments, a gut chip can utilize a porous membrane (e.g., PDMS membrane) coated with ECM (e.g., Collagen I+Matrigel) upon one side of which human intestinal epithelial cells are cultured under flow conditions to produce a physiological shear stress (~0.02 dyne/cm$^2$) while simultaneously exerting cyclic mechanical strain (10% elongation, 0.15 Hz). Gut-specific microvascular endothelial cells can be seeded and cultured on another side of the porous membrane to form a Microvascular Channel as described above. For example, human gut cells (e.g., CaCo2 cells) cultured under these conditions can differentiate by changing their entire transcriptome (measured, e.g., using gene microarrays) and form 3D villus structures, e.g., to match the height of the microfluidic Interstitial Channel (FIG. 11F). In addition, the physiologically relevant conditions recreated in the Gut Chip can enable one to culture living gut bacteria (*Lactobacillus*) directly on top of the living human villus gut epithelium, and hence, permit interrogating the influence of gut microbiome on drug absorption and metabolism using the gut chips.

In some embodiments, the gut chips described herein can comprise any components of the device or can be the device described in the International Appl. No. WO 2012/118799, the content of which is incorporated herein by reference in its entirety.

Kidney Chips: Without limitations, in some embodiments, the kidney chips can be developed and/or modified, e.g., from the basic Lung Chip multichannel design described herein (e.g., as shown in FIG. 2) as well as in Huh D. et al., 2010 and/or in the International Application No. WO 2010/009307, the contents of which are incorporated herein by reference in their entireties. In some embodiments, the kidney chips can utilize a porous membrane (e.g., a PDMS membrane) coated with ECM (e.g., type IV collagen) upon one side of which primary human proximal tubular epithelial cells (e.g., obtained from Biopredic or from a specific subject) are cultured under flow conditions to produce a physiological shear stress (~0.02 dyne/cm$^2$). Kidney-specific microvascular endothelial cells can be cultured on another side of the porous membrane to form a Microvascular Channel as described above. Using such kidney chips, the in vivo nephrotoxicity observed with an active agent, e.g., cisplatin and its inhibition by cimetidine, can be recapitulated and clinically relevant endpoints or biomarkers, such as KIM-1, can be measured.

In some embodiments, the kidney chips described herein can comprise components of the device, or can be the device described in U.S. Provisional Application No.: U.S. 61/449,925, the content of which is incorporated herein by reference in its entirety.

Skin Chips: Without limitations, in some embodiments, the skin chips can be developed and/or modified, e.g., from the basic Lung Chip multichannel design described herein (e.g., as shown in FIG. 2) as well as in Huh D. et al., 2010 and/or in the International Application No. WO 2010/009307, the contents of which are incorporated herein by reference in their entireties. In some embodiments, human foreskin fibroblasts can be plated in a collagen gel on one side of the membrane, and human dermal endothelial cells on the other side of the membrane; human keratinocytes from foreskin can then be plated on top of the collagen gel layer.

In some embodiments, the cells seeded in the skin chips can be further induced to differentiate into a stratified epithelium with basal, spinous and cornified layers, e.g., by passing air through the "Interstitial Channel" in a similar fashion as operated in the lung chip, and creating an air-liquid interface.

Figure 12:
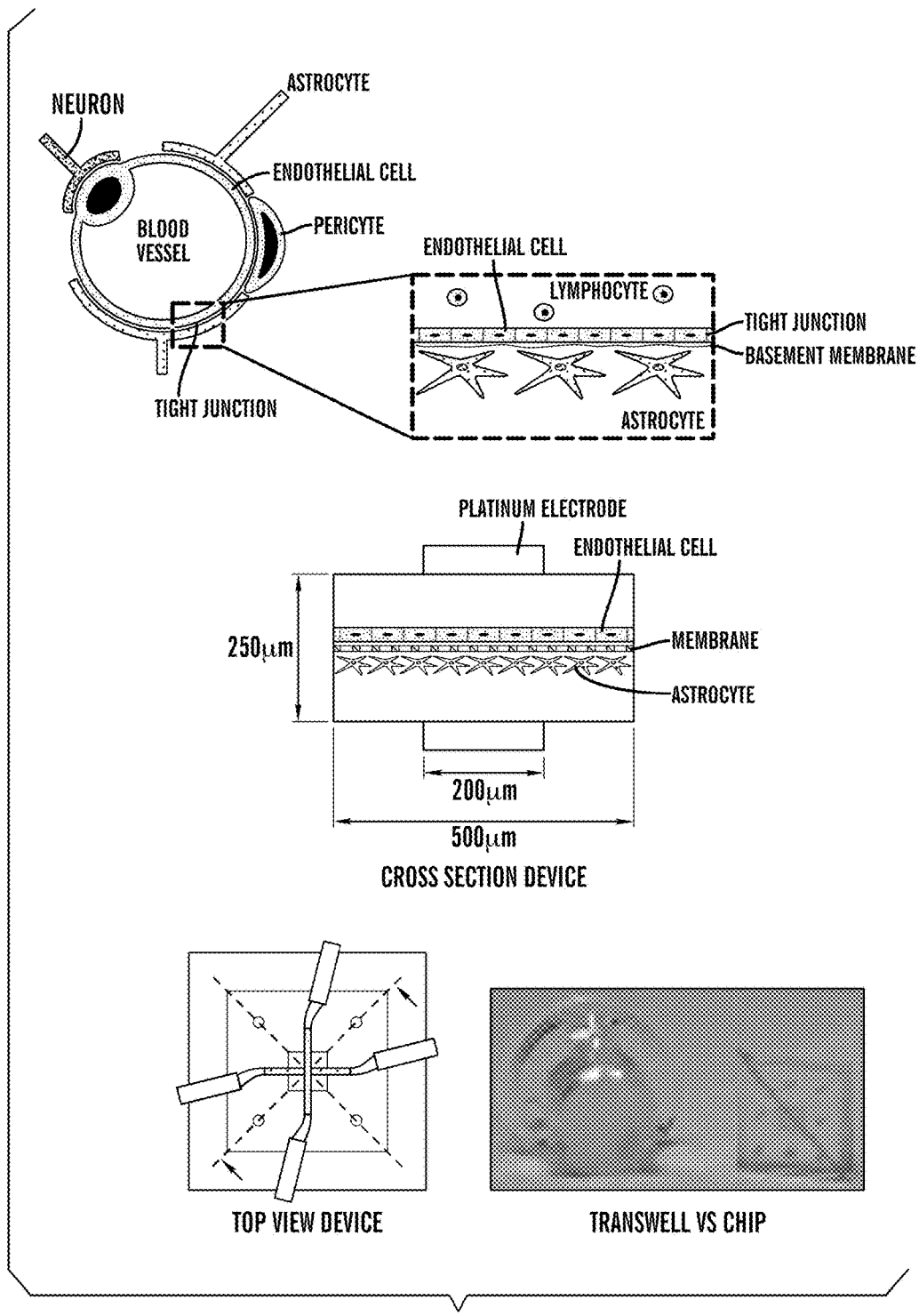
FIG. 12 is a schematic diagram showing architecture of human blood-brain-barrier and an organ chip that mimics the blood-brain-barrier. In one embodiment, the normal architecture of the human blood brain barrier (top panel) is mimicked by culturing human endothelium on one side of a porous membrane and human astrocytes on the other side within a microfluidic channel with platinum electrodes embedded therein (bottom panel).

Brain chips: Without limitations, in some embodiments, the brain chips can be developed and/or modified, e.g., from the basic Lung Chip multichannel design described herein (e.g., as shown in FIG. 2) as well as in Huh D. et al., 2010 and/or in the International Application No. WO 2010/009307, the contents of which are incorporated herein by reference in their entireties. For example, a brain chip can be constructed by first creating a Blood-Brain Barrier (BBB) construct in which astrocytes (e.g., human astrocytes) are cultured on one side of a porous ECM-coated membrane and endothelial cells (e.g., human endothelial cells) on the other side of the porous membrane. In some embodiments, electrodes (e.g., platinum electrodes) are embedded inside the channels, e.g., as shown in the bottom panel of FIG. 12. The inventors have demonstrated generation of an effective permeability barrier, as measured by transepithelial resistance using this approach (FIG. 12).

In alternative embodiments, the brain chips can be developed and/or modified, e.g., based on the design of any embodiments of Heart Chips (e.g., as shown FIG. 8) described herein as well as in Grosberg A. et al. 2011 and in the International Application Nos. WO 2008/045506, WO 2010/011407 and WO2010/042856, the contents of which are incorporated herein by reference in their entireties. Such brain chips can be constructed, e.g., by placing the BBB construct (as described above) in at least one set of channels and then linking the outflow of its Interstitial Channel to a second electrophysiological chamber (as described in the section of Heart Chips) where human brain neuronal networks can be cultured to measure effects on nerve cell toxicity and electrical signaling. Without limitations, the brain chips described herein can be used for various applications, e.g., discovery of methods to deliver an active agent across a BBB, or as a Traumatic Brain Injury (TBI) model to develop new therapies.

Skeletal Muscle Chips: Without limitations, in some embodiments, the skeletal muscle chips can be developed and/or modified, e.g., based on the design of any embodiments of Heart Chips (e.g., as shown FIG. 8) described herein as well as in Grosberg A. et al. 2011 and in the International Application Nos. WO 2008/045506, WO 2010/011407 and WO2010/042856, the contents of which are incorporated herein by reference in their entireties.

Skeletal Muscle Chips are described, for example, in U.S. Provisional Patent Application Ser. No. 61/569,028, filed on Dec. 9, 2011, U.S. Provisional Patent Application Ser. No. 61/697,121, filed on Sep. 5, 2012, and PCT patent application titled "Muscle Chips and Methods of Use Thereof," filed on Dec. 10, 2012 and which claims priority to the US provisional application nos. 61/569,028, filed on Dec. 9, 2011, U.S. Provisional Patent Application Ser. No. 61/697, 121, the entire contents of all of which are incorporated herein by reference in their entireties.

In some embodiments, the skeletal muscle chip can be a heart chip adapted to culture mature skeletal muscle myoblasts or myotubes (e.g., human skeletal muscle myoblasts or myotubes), optionally with neurons, on 2D substrates (e.g., PDMS substrates) or micromolded alginate substrates. These tissue constructs can then be integrated into both a "muscular thin film" (MTF) chamber for contractility measurements and a low volume electrophysiological readout chamber, similar to the operation of the heart chips described herein.

In some embodiments, the skeletal muscle chip can further comprise additional cell types, e.g., adipocytes (e.g., human adipocytes) can be added to the skeletal muscle chip as a heterogeneous co-culture cell layer, or be seeded on a separate side of the membrane to recapitulate two tissue interfaces, e.g., to create disease models within the device. For example, in one embodiment, the adipocyte can be cultured on opposite side of porous membrane that myoblast/neurons are cultured. The adipocytes can be healthy or diseased, depending on the purpose of the application. Healthy human adipocytes can be obtained from a commercial source or isolated from a healthy tissue of a subject. Alternatively, commercially-available healthy primary pre-adipocytes (e.g., Lonza; PT-5022) can be differentiated into adipocytes, e.g., by using known differentiation medium. In some embodiments, diabetic (Type I and II) human adipocytes can be used in the skeletal muscle chip. For example, commercially-available primary (from patients with diabetes) preadipocytes (e.g., Lonza; PT-5023—Type I and PT-5024 Type II) can be differentiated into adipocytes by using known differentiation medium.

To create an in vitro skeletal muscle system in a microfluidic device, in some embodiments, aligned monolayers of muscle cells (e.g., human myoblasts) can be cultured on microcontact printed polymer substrates or membranes (e.g., microcontact printed PDMS substrates, microcontact printed polyurethane membranes and/or micromolded alginate substrates). The human myoblasts or satellite cells (healthy or diseased) can be isolated from a tissue of a subject, and/or obtained from a commercial source, e.g., (healthy; Lonza, XM13A1 and XM15B1).

Figure 13:
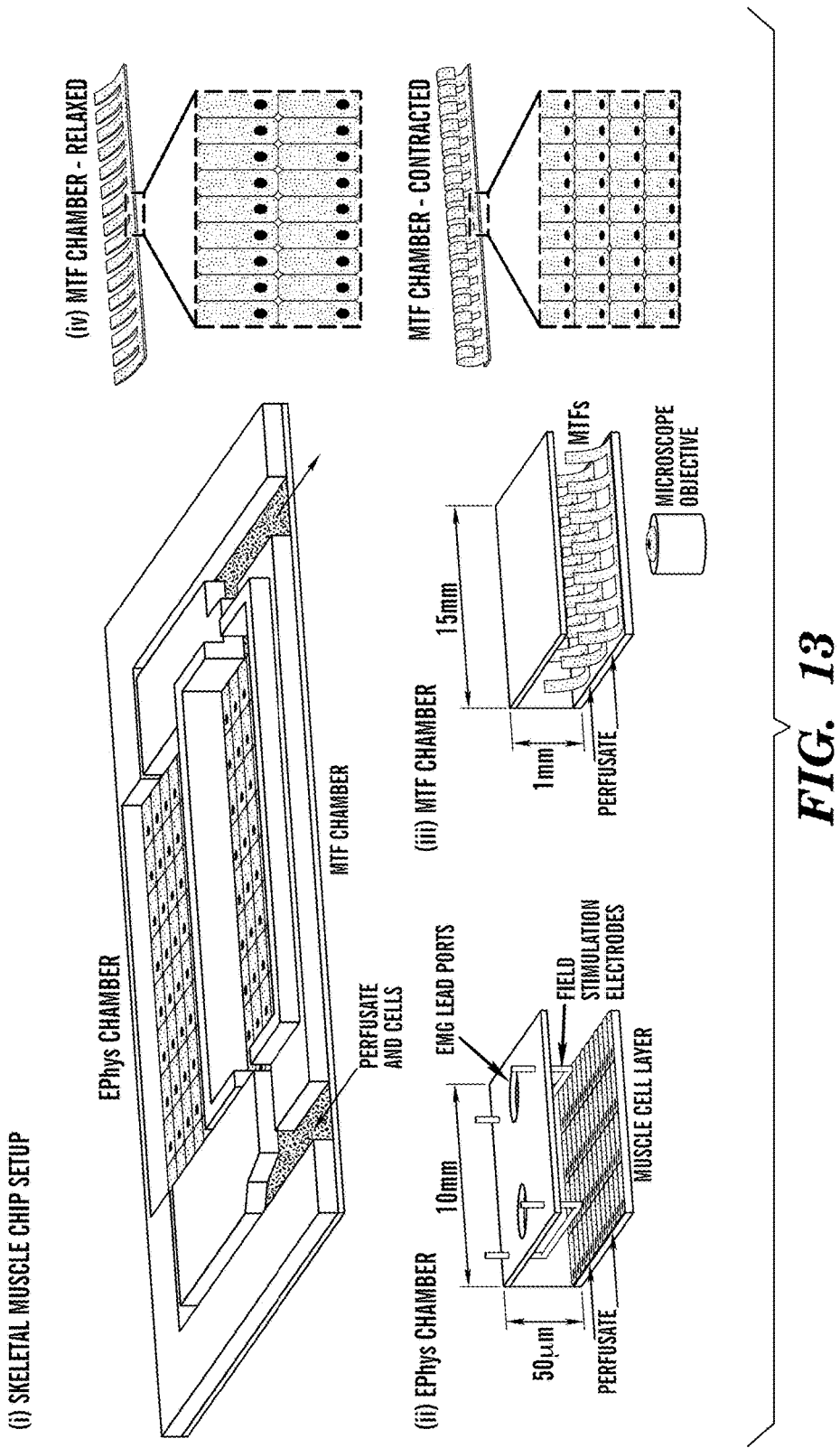
FIG. 13 is a schematic diagram showing exemplary features of a skeletal muscle chip according to one embodiment described herein. (i) depicts a dual-chamber system with a single medium stream that feeds 2 chambers: an electrophysiological (EPhys) chamber and an MTF chamber; (ii) shows that the EPhys chamber can allow EMG recordings on a monolayer of skeletal muscle in a low volume chamber with micro-electrodes embedded in the bottom of the chamber; (iii) shows that a larger chamber situated next to the EPhys chamber can allow high throughput contractility measurements using an array of muscular thin films (MTFs); (iv) shows that the MTF chamber consists of an anisotropic layer of skeletal myocytes cultured on laser-cut horizontal MTFs whose radius of curvature can be measured optically.
Figure 14:
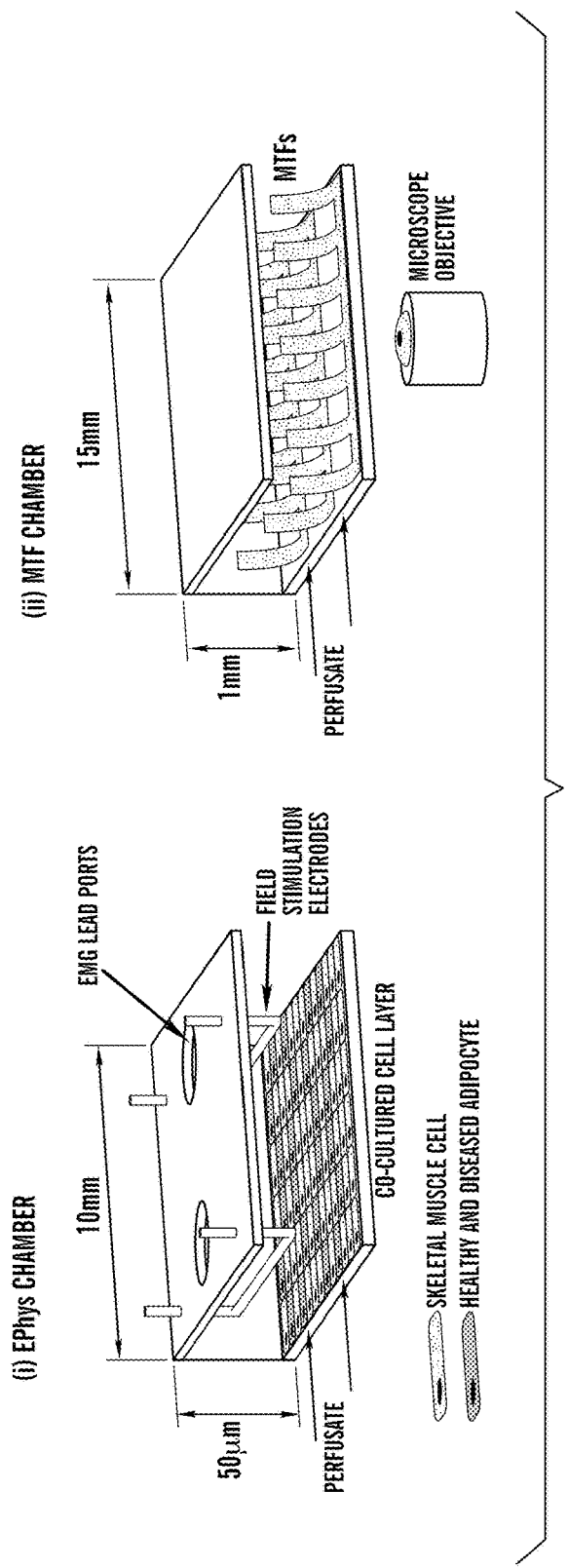
FIG. 14 is a schematic representation of functional readouts from a co-culture of skeletal muscle and adipocyte layers, for example, using the skeletal muscle chip shown in FIG. 13. (i) shows an electrophysiological (EPhys) chamber, which allows EMG recordings on a monolayer of a co-culture of adipose and skeletal muscle. (ii) shows a MTF chamber with an array of muscular thin films (MTFs) built from a heterogeneous co-culture of skeletal muscle and adipose tissue.

In some embodiments, the skeletal muscle chip can comprise at least one or more MTF chamber (FIGS. 13-14), e.g., at least two or more MTF chambers. To create a MTF chamber, in one embodiment, a laser engraving process can be utilized to cut PDMS thin films of skeletal muscle cells (e.g., myoblasts and/or myotubes) cultured as above; followed by microcontact-printing ECM proteins and enclosing the assembly in a microfluidic chamber. To operate the MTF chamber, muscle cells can be cultured on the thin films and the contractile stresses can be assessed by optically monitoring the extent of curvature of the muscular thin films. In some embodiments where the muscle cells and adipose cells are co-cultured in the MTF chamber (e.g., as shown in FIG. 14 (ii)), contractility readout from skeletal muscle-adipocyte can be measured.

In some embodiments, the MTF chambers can be micromolded with grooves (e.g., on an alginate substrate) to create 3D cues, e.g., to help maintain mature contracting muscle in culture (FIGS. 15A-15C).

In some embodiments, the skeletal muscle chip can further comprise an Electrophysiological (EPhys) chamber, the design and operation of which can be similar to the ones employed in the heart chips described herein, except that, e.g., the Ephys chamber is cultured with skeletal muscle chips in the skeletal muscle chips. By way of example only, to fabricate the EPhys chamber, anisotropic muscle cell monolayer can be cultured in a low volume chamber. Then, the muscle cells can be electrically field stimulated using the electrodes on the top, and action potentials can be recorded using the microelectrode array on the bottom. In some embodiments where the muscle cells and adipose cells are co-culture in the EPhys chamber, the EMG can be measured, e.g., as shown in FIG. 14 (i).

Prediction/determination and validation of pharmacological effects: The skeletal muscle chips described herein can be used to determine pharmacological effects on skeletal muscle-specific cells cultured therein. For example, the skeletal muscle-specific cells can be exposed to an active agent by adding the active agent in a culture medium flowing through the Interstitial Channels and/or Microvascular Channels. In some embodiments where the skeletal muscle chip comprises an Electrophysiological Chamber, electrophysiological information can be collected within the chip, which can be in turn modeled with a user-defined algorithm to estimate an ECG. The ECG can then be correlated with reference data (e.g., current in vitro and outputs, or control outputs, e.g., outputs of cells not exposed to the active agent). In one embodiment, the radius of curvature of the contracting MTFs within the chip can be modeled to estimate the stresses exerted by the cells. The MTF contractility measurements can then be correlated with reference data (e.g., current in vitro and clinical outputs, or control outputs, e.g., outputs of cells not exposed to the active agent).

For validation, in one embodiment, statin-induced skeletal muscle myopathy can be replicated. Additionally or alternatively, cerivastatin, which was voluntarily pulled from market in 2001 due to side effects which included rhabdomyolysis and mypothay, can be introduced into the skeletal muscle chips. Skeletal muscle damage markers such as creatine kinase and slow and fast-twitch troponin I (ssTn1, fsTn1) can also be measured (e.g., by in situ immunostaining for the specific marker in the cells, and/or collecting the cells to prepare cell lysates for quantitative measurements of the marker level), in order to validate the ability of the system to replicate injury induced by a known agent (e.g., statin-induced skeletal muscle myopathy). Additionally, since muscle weakness is also a generalized complaint of patients undergoing statin treatment, skeletal muscle contractility measurements can also validate statin-induced in vitro muscle weakness.

In some embodiments, the skeletal muscle chips can be used as diseased models. For example, diabetic muscle microenvironment can be created in some embodiments of the skeletal muscle chips described herein, e.g., by co-culturing type I and type II preadipocytes with the skeletal muscle cells. Type I diabetic mimic chip can be used to evaluate insulin replacement therapies while Type II diabetic mimic chip can be used to determine effectiveness of metformin-induced metabolic benefits.

Further, an exemplary diabetic muscle environment (Type I and II) can be created for pharmaceutical development testing. In some embodiments of Type 2 diabetes model, adipocytes from type 2 diabetic patients (Lonza) and conditioned skeletal muscle can be employed. Metformin, a first line drug used to treat type II diabetes can then be introduced. Muscle contractility can be measured to determine effectiveness of metformin-induced metabolic benefits. In some embodiments of Type 1 diabetes model, Type 1 diabetic adipocytes along with conditioned muscle tissue in zero insulin media can be exposed to commercially-used insulin replacement therapies such as Detemir or Glargine. Improvements in contractility can then be verified due to the increased insulin.

Lung Airway Smooth Muscle Chips: Without limitations, in some embodiments, the lung airway smooth muscle chips can be developed and/or modified, e.g., based on the design of any embodiments of Heart Chips (e.g., as shown FIG. 8) described herein as well as in Grosberg A. et al. 2011 and in the International Application Nos. WO 2008/045506, WO 2010/011407 and WO2010/042856, the contents of which are incorporated herein by reference in their entireties.

In some embodiments, the lung airway smooth muscle chip can be a hybrid bronchial smooth muscle and columnar epithelium organ system, which can be used, e.g., to test bronchial spasms in response to drugs and/or toxins. For example, as shown in FIG. 16B (ii), this hybrid chip can be installed inside a two-chamber microfluidic device that contains a top layer of epithelial cells (e.g., human epithelial cells) adhered to a porous membrane and exposed to air flow and a bottom layer containing flexible muscular thin films, each comprising a monolayer (e.g., a confluent monolayer) of bronchial smooth muscle situated on top of a thin polymer substrate (e.g., a PDMS substrate), which are incubated within a liquid medium. The porous membrane separating the top and bottom layers of the chamber can act as a barrier between the two cell types and allows for chemical exchange.

The material for the membrane that separates airway smooth muscle from the epithelium within the hybrid organ system (e.g., lung airway smooth muscle chips) can be selected for at least one of the following properties, but not limited to: the material is (i) biocompatible, (ii) complies with IS 10993-5 (in vitro cytotoxicity tests for medical devices), (iii) has low absorption of hydrophobic dye/drug and other chemical compounds, (iv) is cell adhesive, (v) is optically clear, is highly flexible, moldable, bondable, (vi) has low autofluorescence, (vii) does not swell in water, or (viii) has any combinations of the aforementioned properties. In one embodiment, the membrane material can include Clear flex 50 polyurethane.

In some embodiments, fabrication of an airway chip can involve micro-contact printing to fabricate engineered smooth muscle tissue and/or (e.g., human) columnar epithelium with well-defined cellular organization and tissue geometry. Bronchial smooth muscle cells (e.g., healthy or diseased cells) can be obtained isolated from a tissue of a subject (e.g., a human), and/or obtained from a commercial source (e.g., healthy: Lonza, CC2576; diseased (COPD); Lonza, 00195274; diseased (asthmatic): Lonza, 00194850).

Human primary bronchial epithelial cells (e.g., healthy or diseased cells) can be isolated from a tissue or obtained from a commercial source (e.g., healthy: ATCC; PCS-300-010, PCS-310-010, Lonza: CC-2540, CC-2547; diseased: Lonza; 00195275, 00194911)

In some embodiments, a lung airway smooth muscle chip ("airway chip") can comprise a MTF chamber. To create a MTF chamber, in one embodiment, a laser engraving process can be utilized to cut PDMS thin films of muscle cells, e.g., bronchial smooth muscle cells (the thin films can be produced in a similar fashion as thin films of cardiomyocytes described above); followed by microcontact-printing ECM proteins and enclosing the assembly in a microfluidic chamber. To operate the MTF chamber, the muscle cells, e.g., bronchial smooth muscle cells, can be cultured on the thin films and the contractile stresses can be assessed by optically monitoring, e.g., the extent of curvature of the muscular thin films. In some embodiments, approximately 0.25 million muscle cells or more can be seeded in each MTF chamber. An alternative strategy for measuring muscle contraction is to grow muscle cells on a wrinkling substrate, e.g., a PDMS membrane, such that as the muscle cells contract, the substrate deforms. In this embodiment, the wrinkling substrate can further comprise a plurality of holes (e.g., a swiss cheese-like PDMS membrane) to facilitate optical detection of the substrate deformation due to muscle cell contraction. For example, the holes within the substrate can remain as a circle when the muscle cells are relaxed, but the circle becomes deformed, e.g., becoming an oval, or an ellipse, due to muscle cell contraction, e.g., as shown in FIGS. 18A-18B.

Figure 17A:
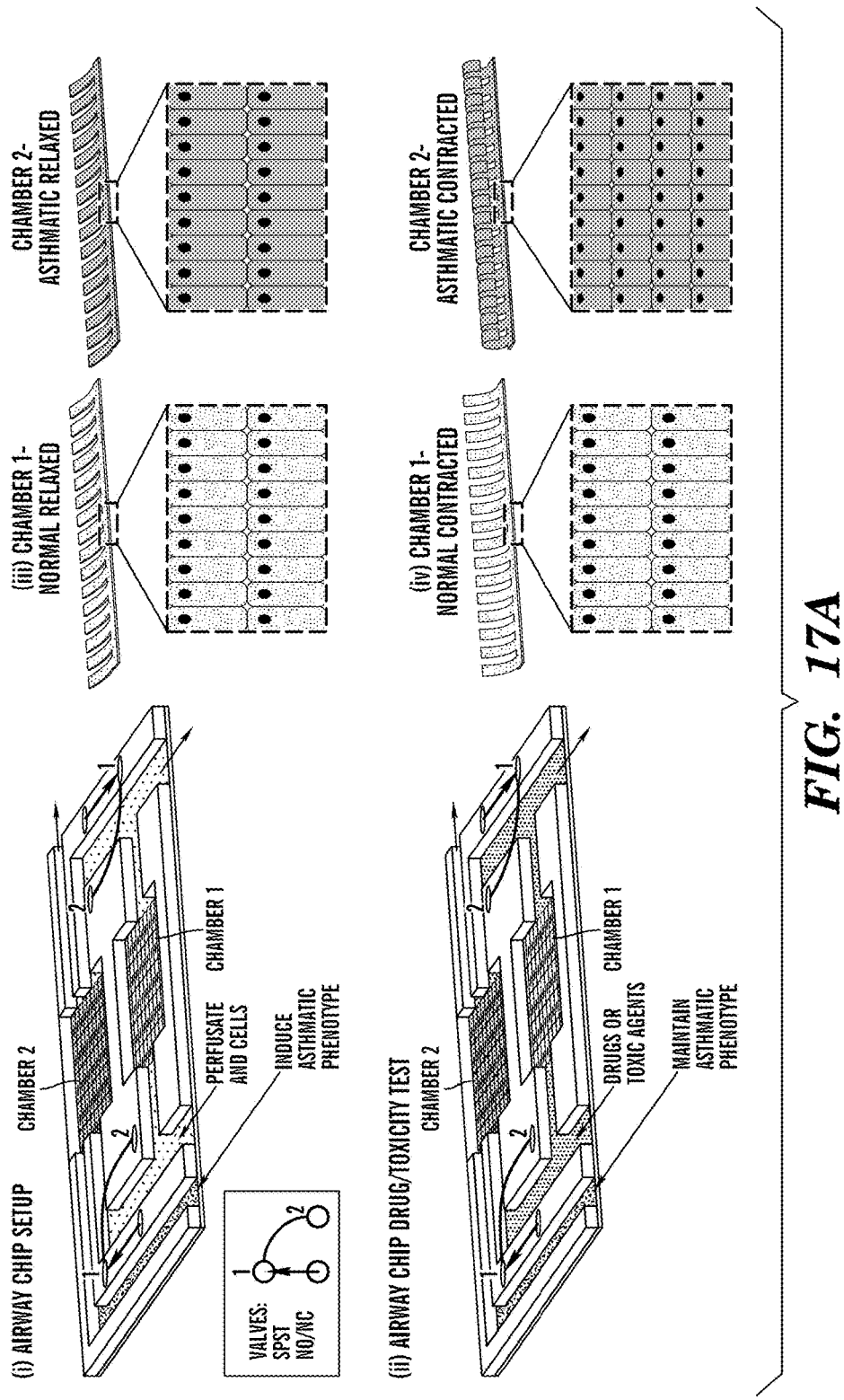
FIGS. 17A-17B are schematic representation showing exemplary features of an airway chip with two chambers in accordance with one embodiment described herein.
Figure 17B:
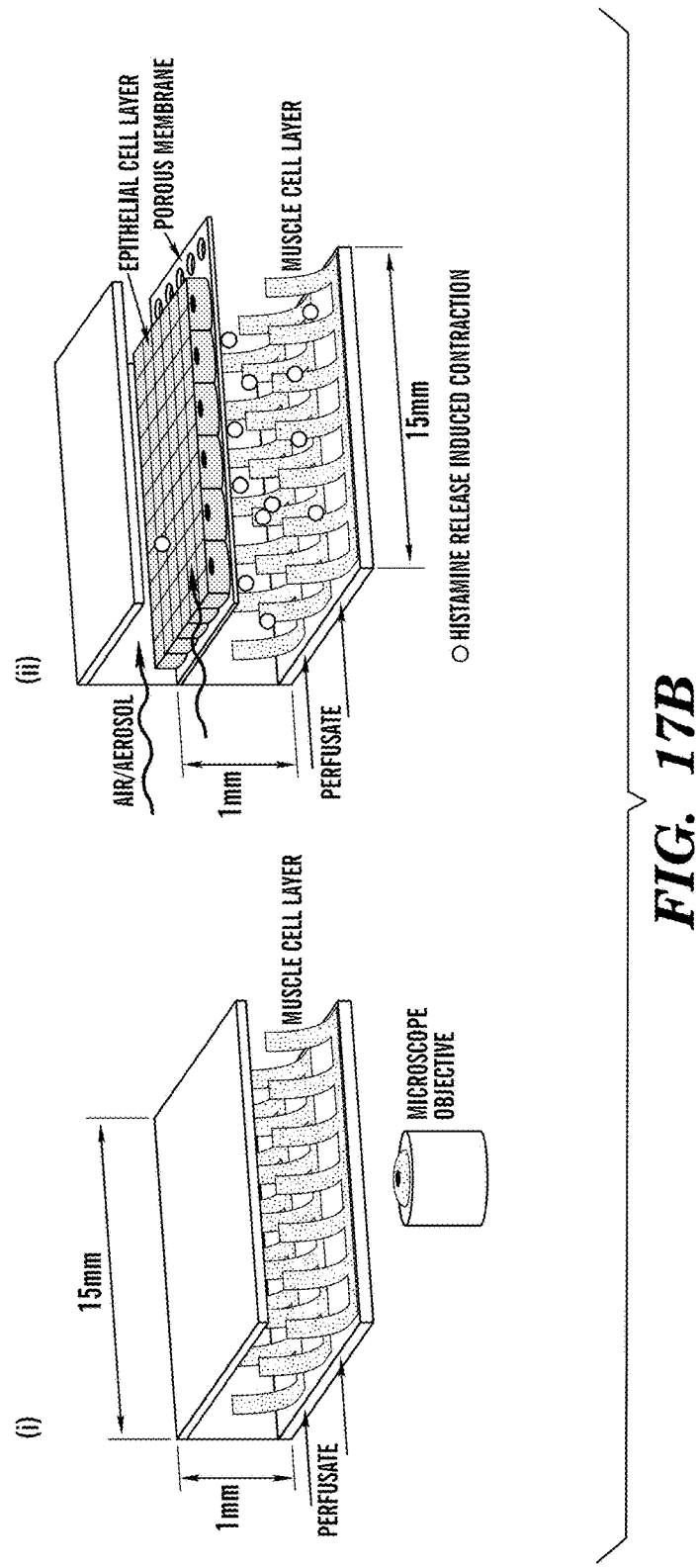

In some embodiments, a two-chamber system can also be engineered for dual outputs (e.g., as shown in FIGS. 17A-17B). For example, normal bronchial epithelial cells can be cultured in one chamber while diseased bronchial epithelial cells (e.g., with asthma phenotype) can be cultured in another chamber, e.g., for comparison of cell behavior, and/or cell response to an active agent. In some embodiments, the cells can be chemically induced to become diseased cells inside a microfluidic device, e.g., by flowing an inducing agent through a separate channel to the cells.

In some embodiments, epithelial cells can be cultured on the chip membrane. In some embodiments, the epithelial cells can remain viable for at least about 3 weeks or longer (e.g., at least about 4 weeks, at least about 5 weeks, at least about 6 weeks or longer) inside the organ chip. For example, the epithelial cells can be cultured on, e.g., 20×4 lined substrates, and the structural and functional response of cells can be characterized by quantifying cytoskeletal alignment and/or effects on gene expression and/or protein translation.

In some embodiments, smooth muscles cells can be cultured on a substrate (e.g., a deformable substrate). In some embodiments, the smooth muscle cells can remain viable for at least 3 weeks or longer (e.g., at least about 4 weeks, at least about 5 weeks, at least about 6 weeks or longer) inside the airway chip. For example, the smooth muscle cells can be cultured on, e.g., 20×4 lined substrates, and the structural and functional response of cells (e.g., cells on a deformable substrate exhibiting morphological changes, e.g., contraction of such PDMS muscular thin film substrate as in FIGS. 16A-16B and FIG. 17A-17B and/or deformation of perforated holes in a membrane as in FIGS. 18A-18B), can be characterized by quantifying cytoskeletal alignment and/or effects on gene expression and/or protein translation.

To characterize cellular response to mechanical stimuli, the bronchial smooth muscle tissue can be monitored for contraction in response to an active agent, e.g., drug or toxic agents (e.g., without limitations, IL-13, acetylcholine). The contractility can be measured for grading the response of the different tissue types to the drugs.

In some embodiments, the lung airway smooth muscle chips can comprise other "helper" cells. To characterize the cellular response to different demographical conditions, e.g., addition of "helper" cells, cells can be co-cultured conditions with other "helper" cell types and/or different cell densities and their effects on gene expression and protein translation can be evaluated using any known methods in the art.

Prediction/determination and validation of pharmacological effects: The airway chips described herein can be used to determine pharmacological effects on airway-specific cells cultured therein. For example, the airway-specific cells can be exposed to an active agent by adding the active agent in a culture medium flowing through the channels. In one embodiment, the radius of curvature of the contracting MTFs within the chip can be modeled to estimate the stresses exerted by the cells. In another embodiment, the eccentricity of the holes within a deformable membrane can be evaluated to determine the state of the cellular contraction (e.g., relaxation vs. contraction state). The contractility measurements (e.g., from contraction of MTFs) can then be correlated with reference data (e.g., current in vitro and clinical outputs, or control outputs, e.g., outputs of cells not exposed to the active agent).

Local airway smooth muscle construct can be characterized for any pharmacological mediators of interest, e.g., but not limited to, Fexofenadine, Denufosol, Terfenadine, Isoproterenol, Amiodarone, and Xigris. Characterization of airway smooth muscle absorption can include, e.g., but not limited to, establishment of absorptive rate constant ($k_a$); establishment of bioavailability (F): Determined by $F = AUC_{INH}/AUC_{IV}$ and determination of onset of action.

The in vitro microphysiological system (e.g., including two or more organ chips) can also be characterized for any pharmacological mediators of interest, e.g., but not limited to, Fexofenadine, Denufosol, Terfenadine, Isoproterenol, Amiodarone, and Xigris. Exemplary characterization include, without limitations, establishment of duration of therapeutic effect; establishment of apparent volume of distribution ($V_d$), via microfluidic channels within the system; establishment of Tmax, time to maximal media concentration, per given dose, inhaled; establishment of Cmax, maximal media concentration, per given dose, inhaled; establishment of terminal half-life, per given dose, inhaled; and/or establishment of efficacy of biotransformation as result of first bypass effect at liver chip.

Performance of airway smooth muscle, local and systemic, within an organ chip or an integrated system, can be corrected to correspond to established pharmacokinetic and pharmacodynamics values for various categories of drugs and toxins.

Disease models: In some embodiments, the lung airway smooth muscle chip can be used as a disease model. The asthmatic phenotype can present as exaggerated bronchial muscle spasms, which can be reflected by changes in contractility. As a control, the effect of substances with known toxicity in humans (e.g., local anesthetics such as procaine, chloroprocaine, and tetracaine) can be introduced to induce bronchial smooth muscle spasms and provide a calibration to existing patient response from the clinic [Ref. 14].

A disease model can be developed, e.g., by integration of diseased cells or by chemical stimulation of a diseased phenotype (e.g., asthmatic phenotype can be induced, e.g., by introducing IL-13 to the culture medium [Ref. 11]), and/or by alteration of temperature and/or media composition [Ref. 12]. Optionally, mechanical strain, electrophysiology, and/or markers for cell injury between asthmatic phenotypes generated by integration of cells from diseased tissues and those induced by allergens or toxins can be compared and contrasted, e.g., to determine which is a better representation of a diseased model.

Figure 19A:
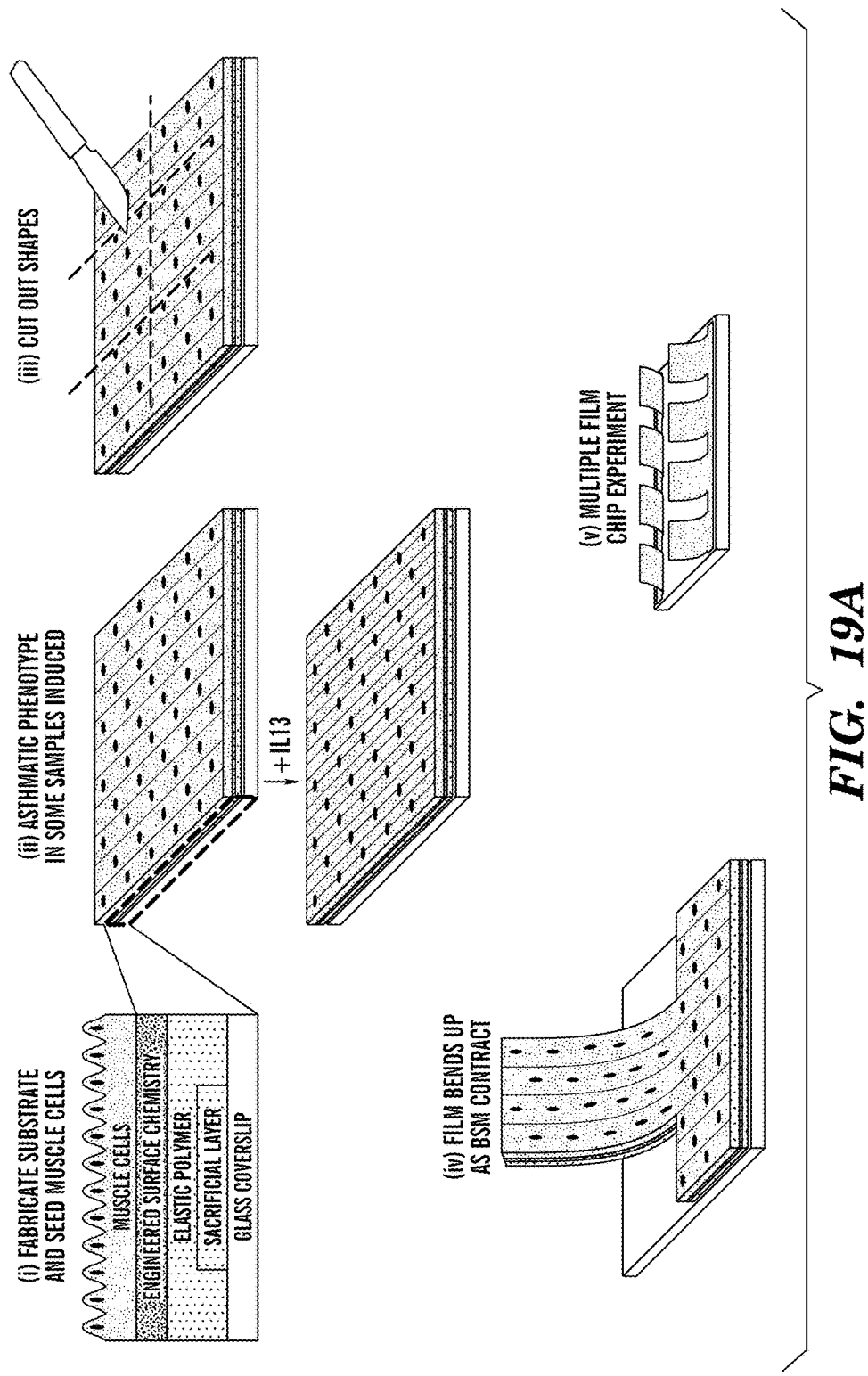
FIGS. 19A-19B shows an exemplary setup of a multiple film chip experiment and collected data from a human asthma (e.g., a chemically-induced human asthma) induced on one embodiment of an organ chip.

By way of example only, to integrate the asthmatic muscle phenotype into the microfluidic device, the asthmatic or chronic obstructive pulmonary disease (COPD) human primary smooth muscle cells (from either commercially available cell lines or samples from asthmatic patients) can be cultured within one of the chambers in the airway chip, e.g., on a deformable substrate, using micro-contact printing to align cells into anisotropic tissues, e.g., as shown in FIG. 19A. Contraction in smooth muscle cell layer can be monitored optically as described above. In the same channel, the micronenvironment conditions, e.g., the levels of oxygen within the medium, cellular ATP, apoptosis, and/or intracellular calcium can be also monitored.

Figure 19B:
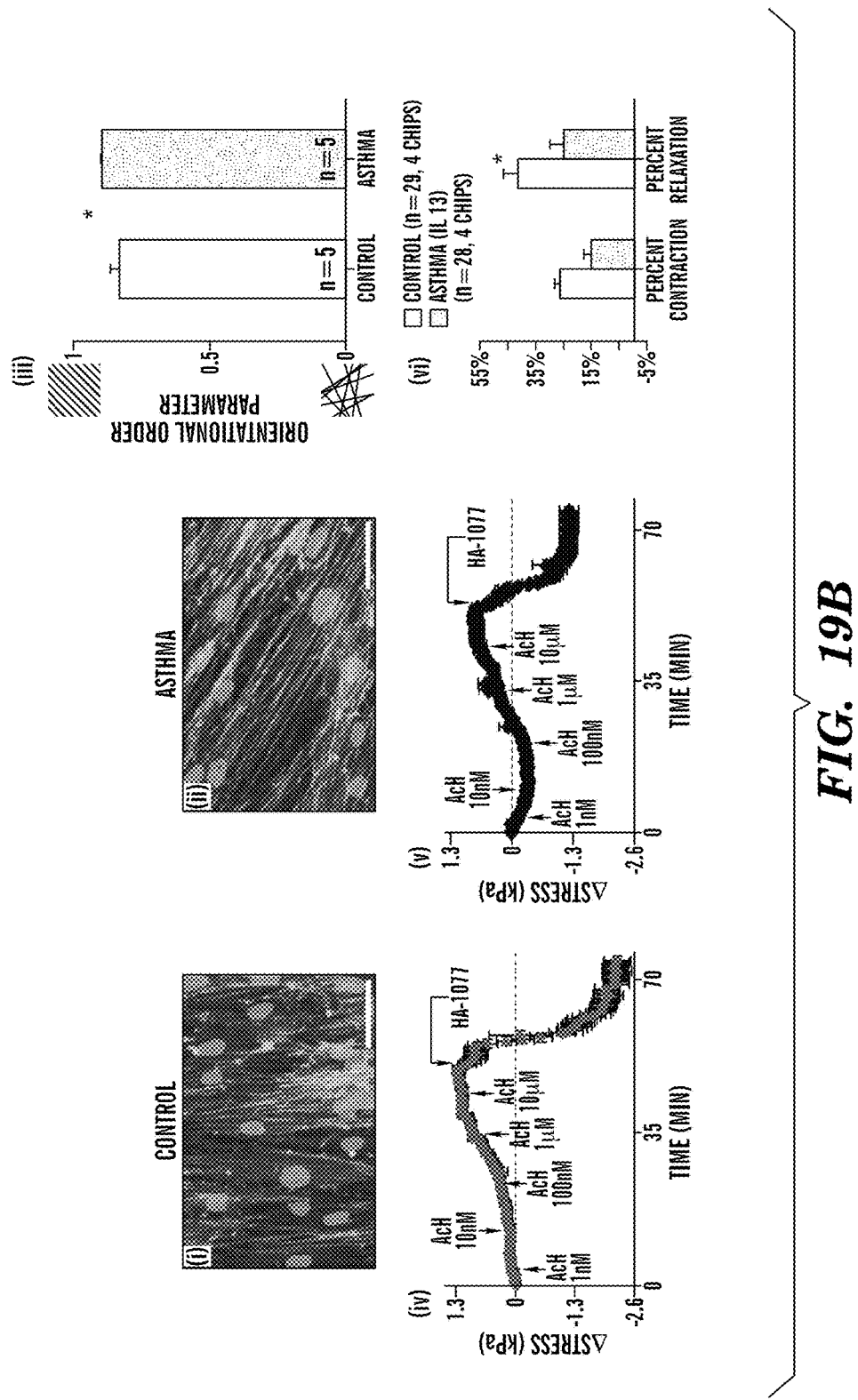

Alternatively, the asthmatic phenotype can be induced by introduction of allergens/drug compounds that drive bronchial spasms associated with asthmatic attacks. For example, toxic agents (e.g., acetylcholine, IL-13, Foradil, Serevent, Advair, Symbicort) can be perfused into the culture medium containing the muscle cell monolayer (FIG. 19B). Alteration in smooth muscle contraction in response to allergens or toxic agents can be monitored optically. In the same channel, the levels of oxygen within the medium, cellular ATP, apoptosis, and/or intracellular calcium can be also monitored.

In some embodiments where the upper channel containing an epithelium (e.g., in a hybrid system as shown in FIG. 16 (ii)), the levels of mucus granules and/or spherules and/or presence of inflammation factors (e.g., but not limited to, IL-3, IL-4, IL-5, IL-13) can be monitored.

The asthmatic phenotype can be induced by introduction of allergens/drug compounds through the air, allergens (e.g. oil fly ash, dust mites, smoke) can be perfused into the aerosol routes within the upper channel of the microfluidic device containing the epithelium (see, e.g., FIG. 16B(ii)). Alterations in smooth muscle contraction in response to allergens or toxic agents can be monitored optically. In the same channel, microenvironment conditions, e.g., but not limited to, the levels of oxygen within the medium, cellular ATP, apoptosis, and/or intracellular calcium can be monitored. In the upper channel containing the epithelium, the levels of mucus granules and/or spherules and/or presence of inflammation factors (e.g., but not limited to, IL-3, IL-4, IL-5, IL-13) can be monitored.

A diseased epithelial cell monolayer can be also integrated within the asthmatic microfluidic device, e.g., a co-culture of the asthmatic or COPD human primary smooth muscle cells (from either commercially available cell lines or samples from asthmatic patients) with the diseased human primary bronchial epithelial cells. By way of example only, the diseased epithelial cell monolayer can be cultured on the membrane (e.g., polyurethane membrane) and the diseased smooth muscle cells on the deformable substrate, using micro-contact printing to align cells into anisotropic tissue in a hybrid system described herein (e.g., as shown in FIG. 16B (ii)). Contraction in smooth muscle cell layer can be monitored optically. In the same channel, microenvironment conditions, e.g., but not limited to, the levels of oxygen (e.g., reduction in oxygen levels) within the medium, cellular ATP, apoptosis, and/or intracellular calcium can be monitored. In the upper channel containing the epithelium, the levels of mucus granules and/or spherules and/or presence of inflammation factors (e.g., but not limited to, IL-3, IL-4, IL-5, IL-13) can be monitored. Further, the hyperplasia and hypertrophy of the columnar epithelial cells (hallmarks of obstructive pulmonary disease) can be assessed optically, e.g., by microscopy.

Asthma is a prevalent disease affecting ~8% percent of the population, and it is in part due to maladaptive remodeling of bronchial smooth muscle. Airborne toxins and air pollution can affect the bronchial smooth muscle, but they are difficult to detect and to predict their effects on the tissue health (and reflect a large scale problem in developing countries). There are currently no commercially available instruments to test cytotoxicity and allergic responses and associated inflammation in vitro, despite the existence of human bronchial smooth muscle cell lines. Beyond the difference in species responses to toxic or therapeutic agents, animal models do not necessarily provide human relevance, predictability, and lower failure rates in the drug pipe-line.

Bronchial smooth muscle spasms can be a response to allergens and/or toxins. This response can be amplified if the muscle undergoes a maladaptive remodeling prior to the introduction of the toxic agent (such as in asthmatic patients). Therefore, an in vitro organ chip system (e.g., a hybrid chip of bronchial smooth muscle tissue and epithelial cell monolayer as described herein) to test for bronchial smooth muscle spasms can provide a tool for various applications, including, but not limited to: testing drugs for curing or exacerbating asthma; testing toxins (including air-borne toxins) in the field; predicting the allergic response of different patient populations. Further, the hybrid chips can be combined with a microfluidic device containing bronchial epithelial and/or pulmonary mast cells, which are important to exacerbation and inflammation response. In other embodiments, the hybrid chips described herein can comprise bronchial epithelial and/or pulmonary mast cells within the same device. In some embodiments where epithelial and mast cells are co-cultured, the epithelial and mast cells can produce inflammation factors (e.g., but not limited to, IL-3, IL-4, IL-5 IL-13) that would cause the spasms in the bronchial smooth muscle, and the levels of these inflammation factors can be measured to evaluate the degree of spasms.

An exemplary protocol of fabricating a lung smooth muscle chip and using the same for evaluating cell response to a drug is shown below: (Any modifications to the protocol within one of skill in the art are also within the scope of the inventions.)

Figure 16A:
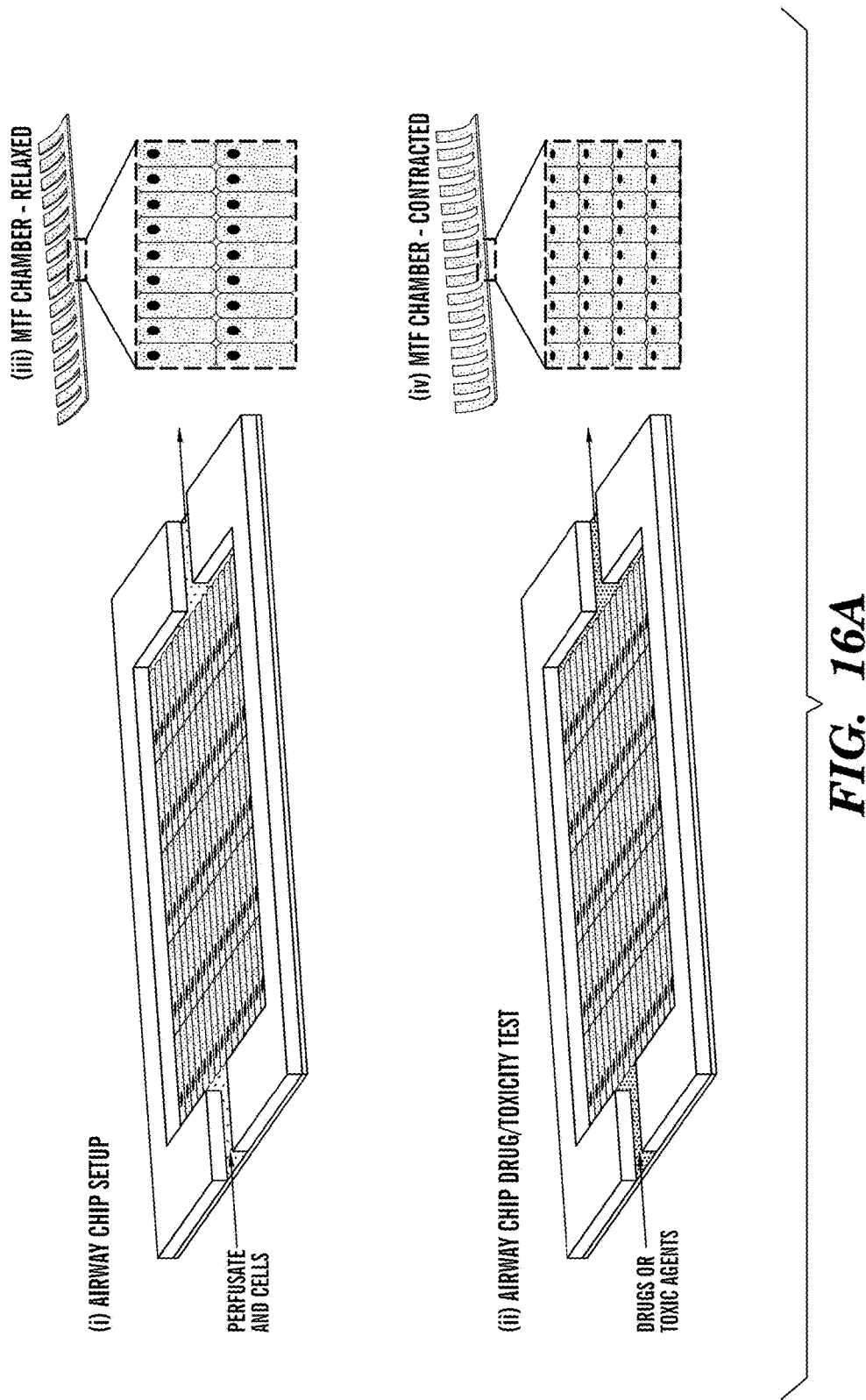
FIGS. 16A-16B is a set of schematic representation showing an airway chip according to one embodiment described herein.
Figure 16B:
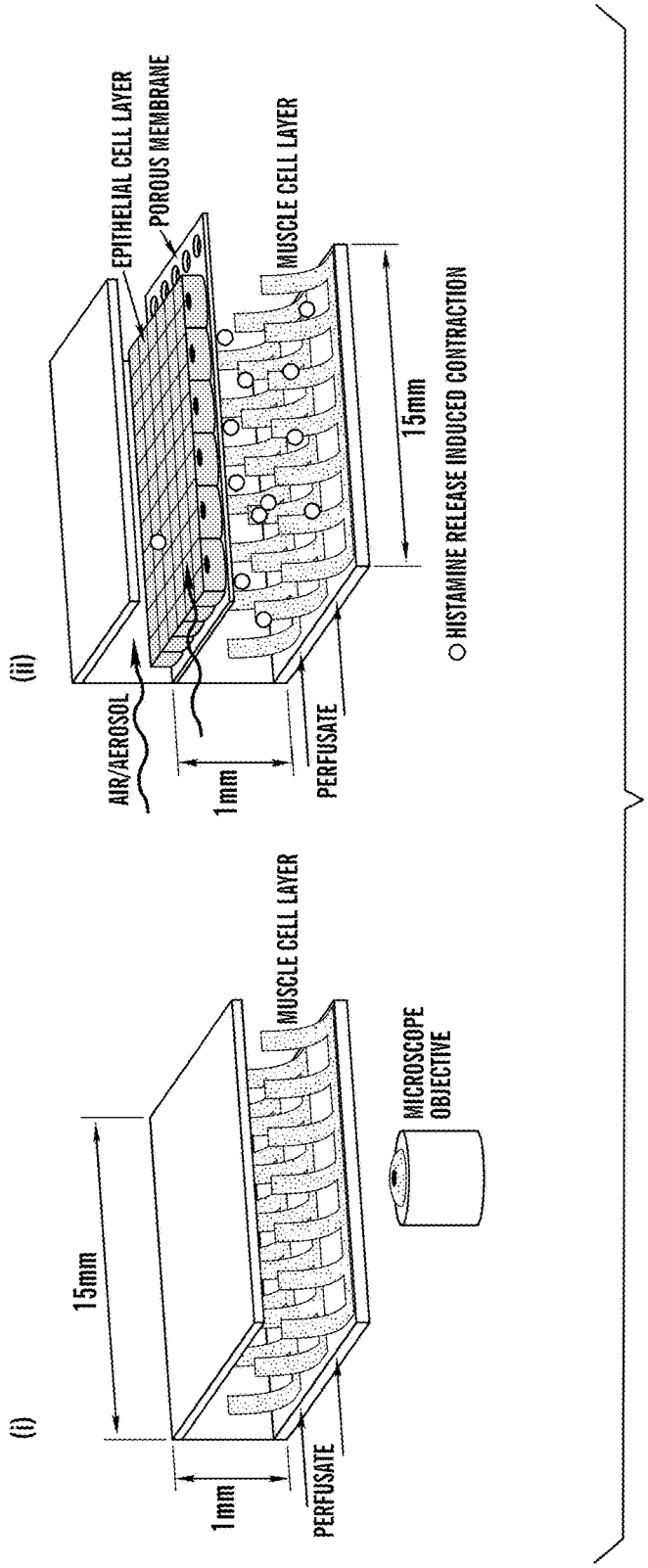

Create a chip with a desirable number of chambers, e.g., one or more chambers (FIG. 16A(i)-(ii));

Control cell shape and tissue alignment within the chambers to recapitulate the native microenvironments. This can be achieved, e.g., by either patterning of ECM, microgrooves, stretching of the membrane, or other similar techniques as described herein;

Seed cells and supply media through micro-fluidic channels (FIG. 16A(i)). The bronchial smooth muscle cells (e.g., human cells) can be obtained from commercially available cell-lines [Ref. 10] and/or primary cells from a subject, e.g., human healthy or asthmatic patients;

The organ chip can also allow for co-culture with other cell types:
  Bronchial epithelial cells can be cultured within the same chamber separated by a membrane (e.g., a transwell membrane), and exposed to exacerbating pollutants, such as oil fly ash (available commercially), dust mites, or smoke;
  The bronchial smooth muscle cells can be combined with pulmonary mast cells either upstream in the microfluidic device or co-cultured within a transwell chamber;

Induce an asthmatic phenotype chemically (e.g., IL-13 during culture [Ref. 11]), by temperature control, and/or alteration of media composition [Ref. 12] in some of the chambers (FIG. 17A(i), chamber 2). Additionally or alternatively, the asthmatic phenotype can be incorporated into the chip by samples derived from asthmatic patients If desired, add a therapeutic drug to the asthmatic chamber Introduce a drug to induce a normal smooth muscle contractile response, and/or a toxic agent to test for bronchial spasms (e.g., acetylcholine)

Contraction of the muscle can be detected using multiple approaches, or any approaches known in the art. Approaches 2 and 3 (below) can be used to mimic the function of the bronchial muscle where the cells close-off micro-holes the same way as they close-off the bronchia (Without construed to be limiting, various approaches described below to measure cell contraction can also be integrated into any organ chips described herein):

1. By making the chamber substrates out of PDMS muscular thin films, it can be used to optically track the bending of each film as a measure of contractility (e.g., FIGS. 16A-16B)

2. Alternatively, a substrate can be created with micro-holes, which are small enough to be impermeable to the cells. These holes can provide the material with greater flexibility, and their shape can be used as an indicator of the amount of contraction by reading out their shape based on the transmitted light (FIGS. 18A-18B);

3. Rows of oval micro-holes can be created with varying eccentricity, such that conduction is possible through the wires in the material if the holes are completely closed. The row of micro-holes with minimal eccentricity that still conducts can be used to provide the readout of the degree of contraction of the tissue; and/or 4. Materials that are capable of varying color with different degrees of stress can also be used;

The output readout of the contractility and proliferation of the bronchial smooth muscle can then be related to lung capacity curves (rate of inhale/exhale) through the modeling:
1. Average material properties of the endothelial layer can be estimated from histological data;
2. Stiffness of the muscle layer can be calculated from the in vitro experimental data (from chip); and/or
3. These can be used to calculate the diameter of the bronchia tube, which can then be used to calculate the airflow/resistance—clinical outputs In some embodiments, the chip's function can be calibrated by introducing a substance with known allergenicity, such as procaine, chloroprocaine, and tetracaine, which have been used in humans as local anesthetics and have been shown to be a plausible allergen that can induce a bronchial smooth muscle spasm [4]. This calibration can also be compared to known patient responses, which can provide the necessary data to predict human response based on the data retrieved from the chip.

For a more recent drug, Raplon (Rapacuronium, Organon) is an anesthetic that was approved in the USA in 1999 and withdrawn by the FDA two years later due to a high risk of fatal bronchial muscle spasm [Ref. 14]. Additionally, drugs such as Novartis AG's Foradil, GlaxoSmithKline's Serevent and Advair, and AstraZeneca's Symbicort, while approved to treat asthma, can themselves cause asthma attacks [Ref. 13]. The chip design described herein can allow for in vitro cultures to run for long periods of time to test such effects, prior to clinical trials.

In some embodiments, the lung airway smooth muscle chips can be connected to at least one lung chip to function as an integral organ chip. In some embodiments, the design of the lung airway smooth muscle can be incorporated into the lung chip design.

In some embodiments, the airway chip can be integrated into the system with other organ chips, which can then be used to evaluate drugs that are effective at treating bronchial smooth muscle tissues, but might be toxic to other organ systems (e.g., Ventolin). Alternatively, such integrated system can also allow for testing of drugs commonly used to affect the function of other organs (e.g., beta blockers that reduce cardiac contractility), but can adversely affect airway resistance in asthmatics.

Drugs can be administered via both intravenous (e.g., via culture medium) and aerosol routes, exhibiting the versatility of the chip design.

The airway muscle chips, alone or in combinations with other organ chips, can be used in various applications. Non-limiting examples of applications are shown below:
Provide an in vitro platform for bronchial smooth muscle spasm testing;
Provide a platform to test the contractility of human bronchial smooth muscle tissue;
Primary cells isolated from different population of patients can be used with this platform to study the effectiveness of drugs for different subsets of the population;
Provide key endpoints—translating chip outputs to clinical diagnostic tools:
The chip readout of the contractility and proliferation of the bronchial smooth muscle can be related to lung capacity curves (rate of inhale/exhale) and compared to the output of pulmonary function tests in the clinic;
The secretion of mucus granules and spherules in the epithelium can be monitored optically as a means to test for mucous secretion that is a hallmark of bronchitis and other obstructive pulmonary diseases; and/or
Patients with advanced chronic obstructive pulmonary disease like chronic bronchitis often exhibit bluish tinted skin, resulting from hypoxia and fluid retention. Thus, the media can be tested for low oxygen levels and arterial blood gas (measuring ability to oxygenate blood at alveoli) "downstream" of obstructed airways.

Testis chips: Without limitations, in some embodiments, the Testis Chip can be developed and/or modified, e.g., from the basic Lung Chip multichannel design described herein (e.g., as shown in FIG. 2) as well as in Huh D. et al., 2010 and/or in the International Application No. WO 2010/009307, the contents of which are incorporated herein by reference in their entireties. In some embodiments, the testis chips can employ (e.g., human) Sertoli and Leydig cells being cultured on one side of the porous ECM-coated membrane and endothelium on the other side of the coated membrane. This Testis chip design can maintain enhanced differentiated testicular functions when the two parenchymal cell types are combined in this manner (Ref. 4).

Figure 20:
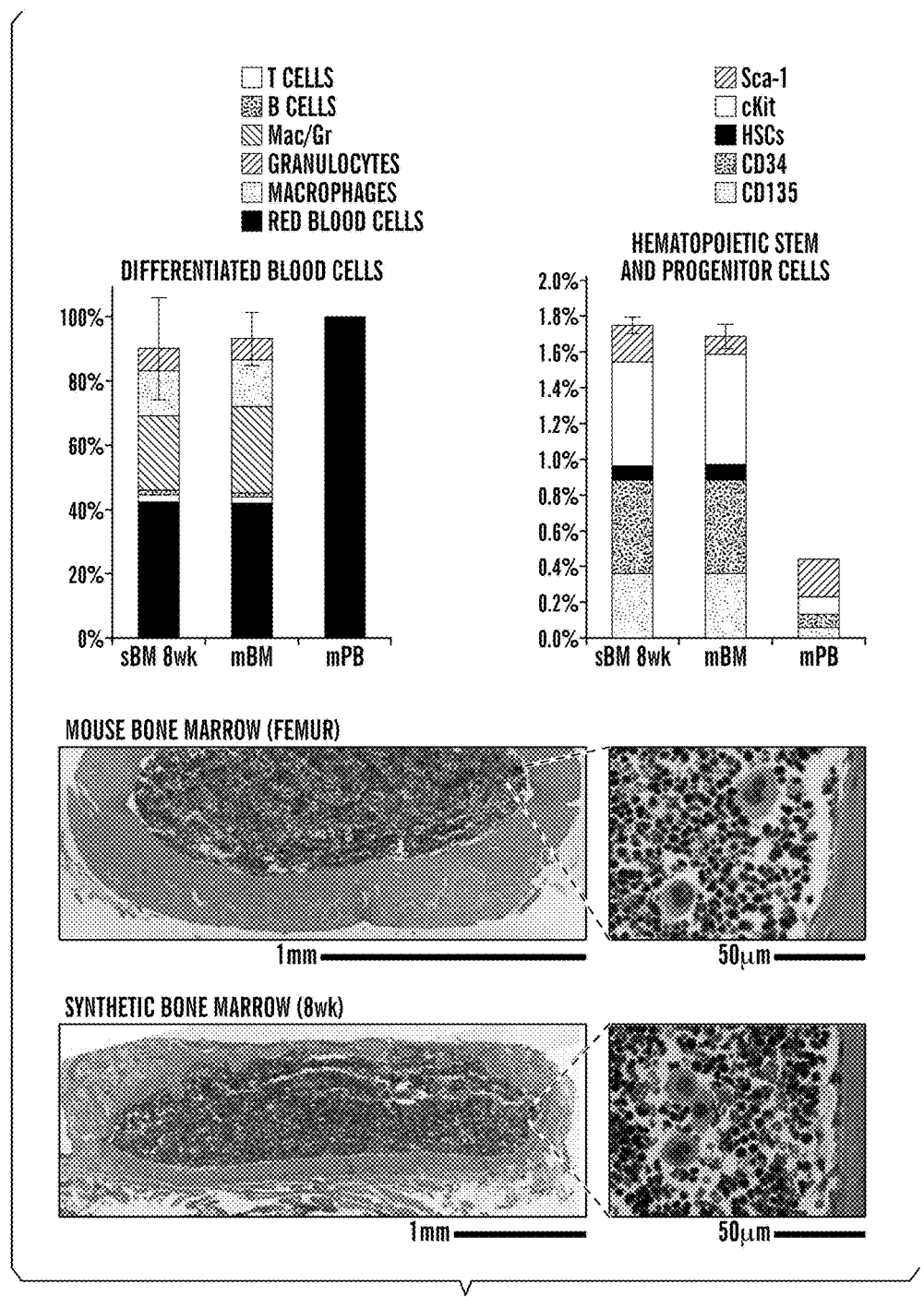
FIG. 20 is a set of data showing that a synthetic bone marrow (sBM) can fully recapitulate natural mouse bone marrow (mBM) but not peripheral blood (mPB) 8 weeks after implanting an organ chip with differentiated blood cells (DMPs) or hematopoietic stem and progenitor stem cells (BMPs) subcutaneously. Similar functionality can be maintained in vitro by culturing in a microfluidic device the sBM explant.

Bone Marrow Chips: To construct a Bone Marrow chip, fully functional bone containing a central marrow can be formed in vivo first by implanting demineralized bone powder and BMPs 2/4 subcutaneously above a muscle layer within a polymer mold (e.g., PDMS mold and culturing it for about 4-8 weeks in vivo. Additional details of the bone marrow chips and methods of making the same can be found in the International Appl. No. PCT/US12/40188, the content of which is incorporated herein by reference in its entirety. The bones that form in these implanted devices can take the shape (e.g., cylindrical shape) of the flexible mold, and contain a fully developed bone marrow with normal morphology and cellular composition (hematopoietic stem cells, progenitor cells, various differentiated blood cell types), when compared to normal mouse bone marrow versus peripheral blood (FIG. 20). The formed marrow can be maintained by placing the formed implant within microfluidic channels, as evidenced by cells isolated from this marrow after 4 days in culture being able to regenerate a functional marrow and reconstitute whole blood formation in gamma-irradiated mice.

Alternatively, simultaneously reconstituting the mouse's injured marrow and forming new marrow in the microfluidic implants can be carried out by irradiating immuno-compromised mice, implanting the demineralized bone powder with BMPs subcutaneously, and then injecting human bone marrow. Once removed and maintained in microfluidic systems, the human marrow can then be used to generate all types of blood cells, which can circulate throughout the entire linked organ chip circuit, e.g., an in vitro microphysiological system, e.g., for studies on inflammation and its relation to drug toxicity.

Without limitations, additional organ chips corresponding to other organs, e.g., spleen chips for filtration of fluid, e.g., blood, as described into the International Appl. No. WO 2012/135834, the content of which is incorporated here by reference in its entirety, can also be integrated into an in vitro microphysiological system described herein.

Exemplary Applications of Organ Chips and/or In Vitro Microphysiological Systems Described Herein At least one or more organ chips can be used for any applications that involve cells. In some embodiments, the organ chips and/or in vitro microphysiological systems can be used as cell culture devices. Compared to 2-D tissue culture flasks, the organ chips and/or in vitro microphysiological systems described herein can provide organ-specific cells a more physiological condition for their growth, and/or maintenance of their differentiated states. For example, lung cells in vivo are generally exposed to a mechanical stimulation, e.g., during breathing. To mimic the breathing action in vitro, organ chips such as lung chips can be used to culture lungs cells as described above. In some embodiments, the cells can be cultured and remain viable (e.g., capable of proliferation) for at least about 3 weeks, at least about 4 weeks, at least about 5 weeks, at least about 6 weeks, at least about 9 weeks, at least about 12 weeks or longer inside the organ chips described herein.

In some embodiments, the organ chips and/or in vitro microphysiological systems can be used for drug screening, PD/PK studies and/or toxicity assays. For example, an active agent can be delivered to target cells cultured in organ chips, e.g., by introducing the active agent into the organ chips as an aerosol and/or as a mixture with the culture medium flowing through the Interstitial Channels and/or Microvascular Channels of the organs chips described herein. Examples of active agents to be delivered to target cells can include, but are not limited to, cells including, e.g., but not limited to, bacteria and/or virus, proteins, peptides, antigens, antibodies or portions thereof, enzymes, nucleic acids, siRNA, shRNA, aptamers, small molecules, antibiotics, drugs or therapeutic agents, molecular toxins, nanomaterials or particulates, aerosols, environmental contaminants or pollutants (e.g., but not limited to, microorganisms, organic/inorganic contaminants present in food and/or water, and/or air pollutants), and any combinations thereof. Exemplary characterization that can be performed with the organ chips and/or in vitro microphysiological systems described herein can include, without limitations, establishment of duration of therapeutic effect; establishment of apparent volume of distribution (Vd), via microfluidic channels within the system; establishment of Tmax, time to maximal media concentration, per given dose; establishment of Cmax, maximal media concentration, per given dose; establishment of terminal half-life, per given dose; and/or establishment of efficacy of biotransformation as result of first bypass effect at the organ chip.

Examples of drugs can include, but are limited to, pharmacologically active drugs and genetically active molecules. Compounds of interest include chemotherapeutic agents, anti-inflammatory agents, hormones or hormone antagonists, ion channel modifiers, and neuroactive agents. Exemplary of pharmaceutical agents suitable for this invention are those described in "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming Organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Additional candidate compounds or drugs can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, naturally or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification to produce structural analogs.

By way of example only, the cells within the organ chips and/or in vitro microphysiological systems can be exposed to a drug by flowing a fluid containing the drug through a channel of an organ chip or an integrated system of different organ chips, such that the fluid is in contact with the cells. In some embodiments, the cells within the organ chips and/or in vitro microphysiological systems can be exposed to an aerosol by flowing a gaseous fluid containing the aerosolized microdroplets of a drug through a channel of an organ chip or an integrated system of different organ chips such that the gaseous fluid is in contact with the cells. Cell response in one or more organ chips can then be measured after or monitored over a period of time. Examples of cell response can include, but are not limited to, viability, proliferation, respiration, metabolism, movement of the cells (e.g., migration, contractile motions), differential expression of biomarkers, and/or production and/or release of certain molecules by the cells. Any methods known in the art can be utilized for detecting or measuring a cell response, e.g., immunostaining, microscopy, immunoassays, PCR, and/or ECG measurements.

In some embodiments where the cells are collected from a subject, a treatment regimen (e.g., a therapeutic agent and/or dosage that works best, among others, for the subject) can be selected and/or optimized by culturing the subject-specific cells in the organ chips and/or in vitro microphysiological systems described herein, exposing the cells to different therapeutic agents and/or dosages, and monitoring the cellular response to various combinations.

In some embodiments, the cells can be observed by microscopy for morphological changes. In some embodiments, the contractile motion of the cells can be measured by ECG measurements. In some embodiments, the cells can be stained for a target protein, e.g., a biomarker, and then observed under a microscope. In some embodiments, the cells can be collected from the organ chips for further analysis, such as RNA, DNA and/or protein analysis. In some embodiments, the culture medium conditioned by the cells can be collected for further analysis, such as RNA, DNA and/or protein analysis. One of skill in the art can readily perform various assays for detecting or measuring different kinds of cell responses.

In some embodiments, the organ chips (e.g., gut chips) and/or in vitro microphysiological systems described herein can be used for studying the role of gut flora (e.g., microorganisms that live in the digestive tracts of animals) and other bacteria within a body of an animal that can have a symbiotic relationship with the host. Various factors other than infections, such as aging, geographical transplant, changes in diet, and/or various therapeutic regimens such as antibiotics can alter the gut flora demographics and the physiology of the host. See, e.g., Maynard C L et al. "Reciprocal interactions of the intestinal microbiota and immune system." Nature. 2012 Sep. 13; 489(7415):231-41; Tremaroli V. and Bäckhed F. "Functional interactions between the gut microbiota and host metabolism." Nature. 2012 Sep. 13; 489(7415):242-9; Lozupone C A et al. "Diversity, stability and resilience of the human gut microbiota" Nature. 2012 Sep. 13; 489(7415):220-30; and Ottman N et al. "The function of our microbiota: who is out there and what do they do?" Front Cell Infect Microbiol. 2012; 2:104. Epub 2012 Aug. 9, for information on gut microbiome and human health/disease. For example, *C. difficile* is a serious cause of antibiotic-associated diarrhea (AAD) and can lead to pseudomembranous colitis, a severe inflammation of the colon, often resulting from eradication of the normal gut flora by antibiotics. Accordingly, in some embodiments, "cassettes" of gut bacteria colonies can be co-cultured with gut cells and/or intestine cells in appropriate organ chips, e.g., gut chips, for example, to model gut flora in a host, and/or to study the effects of different factors on the gut flora demographics and/or physiology of the host cells. In some embodiments, these gut chips can be connected to other organ chips to form in vitro microphysiological systems that can be desirable when considering the mind body axis and the coupling of the enteric and central nervous system. These systems can be also used to study, e.g., but not limited to, digestion, and mental illness.

In some embodiments, methods to study microbial growth, adhesion to host-related surfaces and/or the host-microbiota interactions, e.g., as described in the U.S. Pat. App. No. US 2012/0058551, the content of which is incorporated herein by reference, can be integrated or utilized together with the organ chips and/or in vitro microphysiological system described herein to study the role of gut flora within a body of an animal.

In some embodiments, the organ chips and/or in vitro microphysiological systems described herein can be used to study and/or model parasitic infections, for example, but not limited to, co-culture of intestinal worms, rabies, toxoplasma, and any combinations thereof.

Kits

Another aspect provided herein relates to kits comprising one or a plurality of organ chips, for example, 1, 2, 3, 4, 5, 6, 7, 8, 9, 10, or more organ chips. In some embodiments, the organ chips in the kit can be all the same, i.e., corresponding to the same organ. In some embodiments, at least some of the organ chips in the kit can represent a different organ. In some embodiments, the organ chips in the kit can be pre-assembled together, or fluidically connected together by a user, to form an integrated microphysiological system. For example, a kit directed to a circulatory system can comprise at least one heart chip and at least one bone-marrow chip. Another kit directed to a gastrointestinal system can comprise at least one liver chip and one gut chip. Depending on the microphysiological system of interest, the kits can comprise a plurality of the organ chips that are involved in the microphysiological system.

In some embodiments, each organ chips can be individually packaged, e.g., for sterility. In some embodiments, the kits can further comprise an appropriate culture medium. In some embodiments, the kit can further comprise at least one vial of cells, e.g., vascular endothelial cells and/or organ-specific parenchymal cells. In some embodiments, the kits can further comprise an instruction manual, e.g., instructions on connecting various organ chips together to form an integrated network, cell culture methods, and approaches of measuring various cellular responses.

Fabrications of the Organ Chips Described Herein

The methods used in fabrication of any embodiments of the organ chip described herein can vary with the materials used, and include soft lithography methods, microassembly, bulk micromachining methods, surface micro-machining methods, standard lithographic methods, wet etching, reactive ion etching, plasma etching, stereolithography and laser chemical three-dimensional writing methods, solid-object printing, machining, modular assembly methods, replica molding methods, injection molding methods, hot molding methods, laser ablation methods, combinations of methods, and other methods known in the art. A variety of exemplary fabrication methods are described in Fiorini and Chiu, 2005, "Disposable microfluidic devices: fabrication, function, and application" Biotechniques 38:429-446; Beebe et al., 2000, "Microfluidic tectonics: a comprehensive construction platform for microfluidic systems." Proc. Natl. Acad. Sci. USA 97:13488-13493; Rossier et al., 2002, "Plasma etched polymer microelectrochemical systems" Lab Chip 2:145-150; Becker et al., 2002, "Polymer microfluidic devices" Talanta 56:267-287; Becker et al., 2000, "Polymer microfabrication methods for microfluidic analytical applications" Electrophoresis 21:12-26; U.S. Pat. No. 6,767,706 B2, e.g., Section 6.8 "Microfabrication of a Silicon Device"; McDonald et al., 2002, "Poly(dimethylsiloxane) as a material for fabricating microfluidic devices" Accounts of Chemical Research 35: 491-499. Piccin et al., 2007, "Polyurethane from biosource as a new material for fabrication of microfluidic devices by rapid prototyping" Journal of Chromatography A 1173: 151-158. Each of these references is incorporated herein by reference.

In some embodiments, an organ chip described herein can be formed by replica molding, for example, in which a replica comprising at least biocompatible polymer (e.g., PDMS polymer) conforms to the shape of a master or a mold and replicates the features of the master or the mold. In some embodiments, the replica can be further sealed to a surface to enclose at least one channel.

In some embodiments, an organ chip described herein can be formed by machining or micromachining. The term "micromachining" as used herein can encompass bulk micromachining or surface micromachining as recognized in the art. In one embodiment, bulk micromachining defines microstructures such as channels by selectively etching inside a substrate or a body.

In some embodiments, an organ chip described herein can be formed by solid-object printing. In some embodiments, the solid-object printing can take a three-dimensional (3D) computer-aided design file to make a series of cross-sectional slices. Each slice can then be printed on top of one another to create the 3D solid object.

Embodiments of the various aspects described herein can be illustrated by the following numbered paragraphs.

1. An in vitro microphysiological system comprising:
   a. at least two different organ chips, wherein said at least different two organ chips are selected from either one or both of the following:
      (i) a first organ chip comprising: a body comprising a central channel therein, and an least partially porous and at least partially flexible first membrane positioned within the central channel and along a plane, wherein the first membrane is configured to separate the central channel to form two sub-channels, wherein one side of the first membrane is seeded with vascular endothelial cells, and the other side of the first membrane is seeded with at least one type of organ-specific parenchymal cells;

(ii) a second organ chip comprising: a body comprising a first chamber enclosing a plurality of muscular thin films adapted to measure contraction of muscle cells, and a second chamber comprising a layer of muscle cells on the bottom surface of the second chamber, wherein the bottom surface is embedded with an array of microelectrodes for recording of action potentials, and wherein the top surface of the second chamber is placed with at least a pair of electrodes for providing electric field stimulation to the muscle cells; or (iii) a combination of the first organ chip and the second organ chip; and b. at least one connecting means between said at least two different organ chips.

2. The system of paragraph 1, wherein the system comprises at least three organ chips.

3. The system of paragraph 1 or 2, wherein the connecting means comprises a tubing that fluidically connects an outlet of one of the organ chips to an inlet of another organ chip.

4. The system of any of paragraphs 1-3, wherein the first organ chip is selected from the group consisting of a lung chip, a liver chip, a gut chip, a kidney chip, a skin chip, a brain chip, a testis chip, and any combinations thereof.

5. The system of any of paragraphs 1-3, wherein the second organ chip is selected from the group consisting of a heart chip, a skeletal muscle chip, a lung airway smooth muscle chip, a brain chip, and any combinations thereof.

6. The system of any of paragraphs 1-5, further comprising a bone marrow chip fluidically connected to said at least two different organ chips.

7. The system of any of paragraphs 1-6, further comprising a spleen chip fluidically connected to said at least two different organ chips.

8. The system of any of paragraphs 1-7, wherein the first organ chip further comprises at least a channel wall positioned adjacent to the two sub-channels, wherein the first membrane is mounted to the channel wall; and an operating channel adjacent to the two sub-channels on an opposing side of the channel wall, wherein a pressure differential applied between the operating channel and the two sub-channels causes the channel wall to flex in a desired direction to expand or contract along the plane within the two sub-channels.

9. The system of any of paragraphs 1-8, wherein the second organ chip further comprises an at least partially porous second membrane positioned within the first chamber to form a top chamber and a bottom chamber, wherein the bottom chamber comprises the plurality of muscular thin films on its bottom surface, and wherein the surface of the second membrane in contact with the top chamber is seeded with a layer of epithelial cells.

10. The system of any of paragraphs 1-9, wherein when the system comprises a circulatory system, said at least two different organ chips comprise a heart chip and a bone marrow chip.

11. The system of any of paragraphs 1-10, wherein when the system comprises a respiratory system, said at least two different organ chips comprise a lung chip and an airway smooth muscle chip.

12. The system of any of paragraphs 1-11, wherein when the system comprises an excretory system, said at least two different organ chips comprise a lung chip, a gut chip, and a kidney chip.

13. The system of any of paragraphs 1-12, wherein when the system comprises a nervous system, said at least two different organ chips comprise a brain chip and a chip with neuronal networks.

14. The system of any of paragraphs 1-13, wherein when the system comprises a gastrointestinal system, said at least two different organ chips comprise a liver chip, and a gut chip.

15. The system of any of paragraphs 1-14, wherein the system is adapted to determine at least one pharmacokinetic and/or pharmacodynamics parameter of an active agent.

16. The system of paragraph 15, wherein the active agent is selected from the group consisting of cells, proteins, peptides, antigens, antibodies or portions thereof, antibody-like molecules, enzymes, nucleic acids, siRNA, shRNA, aptamers, small molecules, antibiotics, therapeutic agents, molecular toxins, nanomaterials, particulates, aerosols, environmental contaminants or pollutants, and any combinations thereof.

17. The system of any of paragraphs 1-16, wherein said at least two different organ chips are connected in parallel.

18. The system of any of paragraphs 1-17, wherein said at least two different organ chips are connected in series.

19. The system of any of paragraphs 1-18, further comprising a housing enclosing said at least two different organ chips.

20. The system of any of paragraphs 1-19, wherein said at least two different organ chips comprise at least two said first organ chips.

21. The system of any of paragraphs 1-20, wherein said at least two different organ chips comprise at least two said second organ chips.

22. A kit comprising:
   a. at least one in vitro microphysiological system of any of paragraphs 1-21; and
   b. at least one agent.

23. The kit of paragraph 22, wherein said at least one agent comprises a culture medium, an agent for calibration and/or validation of the system, or a combination thereof.

24. The kit of any of paragraphs 22-23, further comprising at least one vial of vascular endothelial cells.

25. The kit of any of paragraphs 22-24, further comprising at least one vial of organ-specific parenchymal cells.

26. The kit of any of paragraphs 22-25, wherein the organ chips involved in the microphysiological system are each individually packaged.

27. A method comprising:
   a. contacting either one or both of the organ-specific parenchymal cells and the muscle cells cultured in said at least two different organ chips of the in vitro microphysiological system of any of paragraphs 1-21 with at least one active agent for a period of time;
   b. measuring a response of the cells cultured in said at least two different organ chips of the in vitro microphysiological system to determine the effect of the at least one active agent on at least two organs.

28. The method of paragraph 27, wherein the cells are contacted with said at least one active agent by flowing the active agent through the channel or chamber where the cells are cultured.

29. The method of paragraph 28, wherein the active agent is added to a liquid flowing through the channel or the chamber.

30. The method of paragraph 29, wherein the liquid comprises cell culture medium, blood, or a combination thereof.

31. The method of paragraph 28, wherein the active agent is in a form of an aerosol flowing through the channel or the chamber.
32. The method of any of paragraphs 27-31, wherein the response of the cells is selected from the group consisting of viability, proliferation, respiration, metabolism, cell migration, cell contractility, differential expression of cell biomarkers, production and/or release of biomolecules, action potentials, and any combinations thereof.
33. The method of any of paragraphs 27-32, wherein the organ-specific parenchymal cells, the muscle cells, or both are collected from a subject.
34. The method of any of paragraphs 27-32, wherein the organ-specific parenchymal cells, the muscle cells, or both are differentiated from stems cells collected from a subject.
35. The method of paragraph 33 or 34, further comprising comparing the responses of the cells to that of control cells not contacted with said at least one active agent.
36. The method of any of paragraphs 27-35, wherein the active agent is selected from the group consisting of cells, proteins, peptides, antigens, antibodies or portions thereof, antibody-like molecules, enzymes, nucleic acids, siRNA, shRNA, aptamers, small molecules, antibiotics, therapeutic agents, molecular toxins, nanomaterials, particulates, aerosols, environmental contaminants or pollutants, and any combinations thereof.
37. The method of paragraph 36, wherein when said at least active agent comprises a therapeutic agent, the method further comprises selecting a treatment regimen comprising the therapeutic agent.
38. The method of paragraph 37, further comprising administering the therapeutic agent to the subject.
39. The method of any of paragraphs 33-38, wherein the subject is a human subject.
40. The method of any of paragraphs 27-39, further comprising growing the cells for at least about 3 weeks.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. A subject can be male or female. Preferably, the subject is a mammal. The mammal can be a human, non-human primate, mouse, rat, dog, cat, horse, or cow, but are not limited to these examples. Mammals other than humans can be advantageously used as subjects that represent animal models of a disease or disorder.

As used herein, the term "fluid" refers to any flowable material or medium, e.g., but not limited to, liquid, gas, suspension, aerosols, cell culture medium, and/or biological fluid). In some embodiments, the fluid can comprise one or more target species, e.g., but not limited to cells, and/or active agents described herein. Without wishing to be bound by theory, the fluid can be liquid (e.g., aqueous or non-aqueous), supercritical fluid, gases, solutions, and suspensions.

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments;

vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from a composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals, anti-inflammatory agents, vaccines, and any combinations thereof.

As used herein, the term "molecular toxin" refers to a compound produced by an organism which causes or initiates the development of a noxious, poisonous or deleterious effect in a host presented with the toxin. Such deleterious conditions may include fever, nausea, diarrhea, weight loss, neurologic disorders, renal disorders, hemorrhage, and the like. Toxins include, but are not limited to, bacterial toxins, such as cholera toxin, heat-liable and heat-stable toxins of *E. coli*, toxins A and B of *Clostridium difficile*, aerolysins, and hemolysins; toxins produced by protozoa, such as *Giardia*; toxins produced by fungi. Molecular toxins can also include exotoxins, i.e., toxins secreted by an organism as an extracellular product, and enterotoxins, i.e., toxins present in the gut of an organism.

As used herein, the term "cells" refers to biological cells selected from the group consisting of living or dead cells (prokaryotic and eukaryotic, including mammalian), viruses, bacteria, fungi, yeast, protozoan, microbes, and parasites. The biological cells can be a normal cell or a diseased cell. Mammalian cells include, without limitation; primate, human and a cell from any animal of interest, including without limitation; mouse, hamster, rabbit, dog, cat, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells, progenitor cells, immune cells, blood cells, and any combinations thereof. The cells can be derived from a wide variety of tissue types without limitation such as; hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, and fetus. Stem cells, embryonic stem (ES) cells, ES-derived cells and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy and/or affected with a disease. While cells can be obtained from a fluid sample, e.g., a blood sample, cells can also be obtained, as a non-limiting example, by biopsy or other surgical means know to those skilled in the art.

Exemplary fungi and yeast include, but are not limited to, *Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii* (or *Pneumocystis carinii*), *Stachybotrys chartarum*, and any combination thereof.

Exemplary bacteria include, but are not limited to: anthrax, *campylobacter*, cholera, diphtheria, enterotoxigenic *E. coli, giardia*, gonococcus, *Helicobacter pylori, Hemophilus* influenza B, *Hemophilus* influenza non-typable, meningococcus, pertussis, pneumococcus, *salmonella, shigella, Streptococcus* B, group A *Streptococcus*, tetanus, *Vibrio cholerae, yersinia, Staphylococcus, Pseudomonas* species, Clostridia species, *Myocobacterium tuberculosis, Mycobacterium leprae, Listeria monocytogenes, Salmonella typhi, Shigella dysenteriae, Yersinia pestis, Brucella* species, *Legionella pneumophila*, Rickettsiae, *Chlamydia, Clostridium perfringens, Clostridium botulinum, Staphylococcus aureus, Treponema pallidum, Haemophilus influenzae, Treponema pallidum, Klebsiella pneumoniae, Pseudomonas aeruginosa, Cryptosporidium parvum, Streptococcus pneumoniae, Bordetella pertussis, Neisseria meningitides*, and any combination thereof.

Exemplary parasites include, but are not limited to: *Entamoeba histolytica; Plasmodium* species, *Leishmania* species, Toxoplasmosis, Helminths, and any combination thereof. Other examples of parasites can include, but are not limited to, intestinal worms, rabies, toxoplasma, and any combinations thereof.

Exemplary viruses include, but are not limited to, HIV-1, HIV-2, hepatitis viruses (including hepatitis B and C), Ebola virus, West Nile virus, and herpes virus such as HSV-2, adenovirus, dengue serotypes 1 to 4, ebola, enterovirus, herpes simplex virus 1 or 2, influenza, Japanese equine encephalitis, Norwalk, papilloma virus, parvovirus B19, rubella, rubeola, vaccinia, varicella, Cytomegalovirus, Epstein-Barr virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, poliovirus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Human T-cell Leukemia virus type-1, Hantavirus, Rubella virus, Simian Immunodeficiency viruses, and any combination thereof.

As used herein, the term "environmental contaminants or pollutants" refers to microorganisms, molecules, and/or substances originated from an environmental source, e.g., air, food, and/or water, that can adversely affect at least one physiological function of a subject in a temporary or permanent manner, and/or can be fatal when they are ingested or inhaled by the subject. Exemplary environmental contaminants or pollutants can include, but are not limited to microorganisms (e.g., *Cryptosporidium, Giardia lamblia*, bacteria, *Legionella*, Coliforms, viruses, fungi, molds, spores), bromates, chlorites, haloactic acids, trihalomethanes, chloramines, chlorine, chlorine dioxide, antimony, arsenic, mercury (inorganic), nitrates, nitrites, selenium, thallium, Acrylamide, Alachlor, Atrazine, Benzene, Benzo (a)pyrene (PAHs), Carbofuran, Carbon, etrachloride, Chlordane, Chlorobenzene, 2,4-D, Dalapon, 1,2-Dibromo-3-chloropropane (DBCP), o-Dichlorobenzene, p-Dichlorobenzene, 1,2-Dichloroethane, 1,1-Dichloroethylene, cis-1,2-Dichloroethylene, trans-1,2-Dichloroethylene, Dichloromethane, 1,2-Dichloropropane, Di(2-ethylhexyl) adipate, Di(2-ethylhexyl) phthalate, Dinoseb, Dioxin (2,3,7,8-TCDD), Diquat, Endothall, Endrin, Epichlorohydrin, Ethylbenzene, Ethylene dibromide, Glyphosate, Heptachlor, Heptachlor epoxide, Hexachlorobenzene, Hexachlorocyclopentadiene, Lead, Lindane, Methoxychlor, Oxamyl (Vydate), Polychlorinated, biphenyls (PCBs), Pentachlorophenol, Picloram, Simazine, Styrene, Tetrachloroethylene, Toluene, Toxaphene, 2,4,5-TP (Silvex), 1,2,4-Trichlorobenzene, 1,1,1-Trichloroethane, 1,1,2-Trichloroethane, Trichloroethylene, Vinyl chloride, and Xylenes, smog, carbon monoxide, sulfur dioxide, and any combinations thereof.

By the term "nanomaterials" is generally meant structures having at least one dimension in nanometer range. Examples of nanomaterials that can be exposed to cells can include, but are not limited to, single or multi-walled nanotubes, nanowires, nanodots, quantum dots, nanorods, nanocrystals, nanotetrapods, nanotripods, nanobipods, nanoparticles, nanosaws, nanosprings, nanoribbons, nanocapsules, branched nanomaterials, and any combinations thereof. The nanomaterials can be made of or comprise, e.g., carbon, metal or alloy, metal oxide, polymer, or any synthetic materials. In some embodiments, the nanomaterials can comprise an active agent described herein, e.g., active agent-loaded nanoparticles.

As used herein, the term "particulates" refers to fine particles, powder, flakes, etc., that exist in a relatively small form. In some embodiments, the particulates are small enough to be inhaled by a subject. In some embodiments, the particulates can be produced as a by-product of a chemical reaction, e.g., burning a fuel. In some embodiments, the particulates can be produced by, for example, grinding, shredding, fragmenting, pulverizing, atomizing, or otherwise subdividing a larger form of the material into a relatively small form. Examples of particulates can include, but are not limited to, soot, dust, smoke, aerosols, and any combinations thereof.

As used herein, the term "aerosols" refers to gaseous suspensions or solutions of dispersed solid or liquid particles, e.g., but not limited to, sprays, colloids, mists and respirable aerosols. The aerosols can be in suspension, solution or dry powder form. An aerosol can comprise an active agent described herein, e.g., cells (including, e.g., but not limited to, bacteria and/or virus), proteins, peptides, antigens, antibodies or portions thereof, enzymes, nucleic acids, siRNA, shRNA, aptamers, small molecules, antibiotics, therapeutic agents, molecular toxins, nanomaterials, particulates, environmental contaminants or pollutants (e.g., but not limited to, microorganisms, organic/inorganic contaminants present in food and/or water, and/or air pollutants). As used herein, the term "respirable aerosol" refers to an aerosol having a component that can be delivered to the lungs of a subject, and/or be deposited on the surfaces of a subject's nasal passages and/or adsorbed onto the tissue of the nasal passages.

As used herein, the term "treating" refers to therapeutic treatment wherein the purpose is to prevent or slow the development of the disease or disorder. Treatment is generally "effective" if one or more symptoms or clinical markers are reduced. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a disease or disorder, as well as those likely to develop a disease or disorder.

REFERENCES

1. Huh D, Matthews B D, Mammoto A, Montoya-Zavala M, Hsin H Y, and Ingber D E. Reconstituting organ-level lung function on a chip. Science 2010, 328: 1662.
2. Grosberg A, Alford P W, McCain M L, Parker K K. Ensembles of engineered cardiac tissues for physiological and pharmacological study: Heart on a chip. Lab on a Chip 2011, 11: 4165.
3. Edward L, LeCluyse, Alexandre E, Hamilton G A, Viollon-Abadie C, Coon D J, Jolley S, and Richert L. Isolation and Culture of Primary Human Hepatocytes, In: Helgarson C, ed., Basic Cell Culture Protocols: Methods in Molecular Biology—Third Edition, Humana Press, 2004.
4. Darby S, Moore M, Wikswo J P, Reiserer R, Friedlander T, Schaffer D K, Seale K T. A Metering Rotary Nanopump for Microfluidic Systems, Lab on a Chip 2010, 10: 3218.
5. Velkovsky M, Snider R, Cliffel D E, Wikswo J P. Modeling the Measurements of Cellular Fluxes in Microbioreactor Devices Using Thin Enzyme Electrodes, Journal of Mathematical Chemistry 2011, 49: 251.
6. Eklund S E, Taylor D, Kozlov E, Prokop A, Cliffel D E. A Microphysiometer for Simultaneous Measurement of Changes in Extracellular Glucose, Lactate, Oxygen, and Acidification Rate, Anal. Chem. 2004, 76: 519.
7. Force T, Krause D S, & Van Etten R A (2007) Molecular mechanisms of cardiotoxicity of tyrosine kinase inhibition. Nature reviews. Cancer 7(5):332.
8. Zhu W, et al. (2008) Acute doxorubicin cardiotoxicity is associated with p53-induced inhibition of the mammalian target of rapamycin pathway. Circulation:CIRCULATIONAHA. 108.799700.
9. Finlayson K, Turnbull L, January C T, Sharkey J, & Kelly J S (2001) [3H] Dofetilide binding to HERG transfected membranes: a potential high throughput preclinical screen. European journal of pharmacology 430(1):147-148.
10. https://shop.lonza.com/shop/prd/human-bronchial-smooth-muscle-cells/lonza_b2b/7.0-7_2_86_69_76_10_13/2/DF3699C5729946F18852001A4B525E10/
11. Chiba et al., 2009
12. Zhou et al., Human Bronchial Smooth Muscle Cell Lines Show a Hypertrophic Phenotype Typical of Severe Asthma, AMERICAN JOURNAL OF RESPIRATORY AND CRITICAL CARE MEDICINE, VOL 169 2004
13. http://www.fda.gov/NewsEvents/Newsroom/PressAnnouncements/ucm200931.htm
14. http://www.homesteadschools.com/dental/courses/LocalAnesthesia/part2.htm All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method comprising:
   (a) contacting muscle cells, organ-specific parenchymal cells that are a different cell type from the muscle cells, or a combination thereof, with at least one active agent for a period of time,
     wherein the organ-specific parenchymal cells and the muscle cells are cultured independently in at least two different organ chips, wherein said at least two different organ chips are each independently configured according to either a first organ chip or a second organ chip, and are coupled by at least one connecting means between said at least two different organ chips,
     wherein at least a first type of the organ-specific parenchymal cells are cultured on a first side of an at least partially porous first membrane disposed in a body of the first organ chip, the first organ chip comprising: the body comprising a central channel therein, and the first membrane positioned within the central channel and along a plane, wherein the first membrane is configured to separate the central channel to form two sub-channels, and a second side of the first membrane is seeded with vascular endothelial cells, and
     wherein the muscle cells are cultured in the second organ chip comprising: a body comprising a chamber enclosing a plurality of muscular thin films that include the muscle cells adhered to a biopolymer substrate, the muscular thin films configured such that contraction of the adhered muscle cells causes the muscular thin films to bend, wherein the first chamber is configured to measure contraction of the adhered muscle cells; and
   (b) measuring a response of the cells cultured in said at least two different organ chips to determine the effect of the at least one active agent on at least two organs, the measuring including measuring a response by the contraction of the adhered muscle cells.

2. The method of claim 1, wherein the cells are contacted with said at least one active agent by flowing the active agent in a liquid through the channel or chamber where the cells are cultured.

3. The method of claim 2, wherein the active agent is added to a liquid flowing through the channel or the chamber.

4. The method of claim 3, wherein the liquid comprises cell culture medium, blood, or a combination thereof.

5. The method of claim 2, wherein the active agent is in a form of an aerosol flowing through the channel or the chamber.

6. The method of claim 1, wherein the response of the cells is selected from the group consisting of viability, proliferation, respiration, metabolism, cell migration, cell contractility, differential expression of cell biomarkers, production and/or release of biomolecules, action potentials, and any combinations thereof.

7. The method of claim 1, wherein the organ-specific parenchymal cells, the muscle cells, or both are collected from a subject or differentiated from stem cells collected from the subject.

* * * * *

UNITED STATES PATENT AND TRADEMARK OFFICE
CERTIFICATE OF CORRECTION

PATENT NO.        : 10,087,422 B2
APPLICATION NO.   : 14/363105
DATED             : October 2, 2018
INVENTOR(S)       : Donald E. Ingber et al.

Page 1 of 1

It is certified that error appears in the above-identified patent and that said Letters Patent is hereby corrected as shown below:

In the Specification

At Column 1, Lines 15-19:
"This invention was made with government support under U01 NS073474-01 from the National Institutes of Health and Food and Drug Administration, and W911NF-12-2-0036 from the Defense Advanced Research Projects Agency. The government has certain rights in the invention."

Should be replaced with:
--This invention was made with government support under W911NF-12-2-0036 awarded by U.S. Army Research Office (ARO) and under NS073474 awarded by National Institutes of Health (NIH). The government has certain rights in this invention.--

Signed and Sealed this
Twenty-first Day of October, 2025

John A. Squires
*Director of the United States Patent and Trademark Office*